United States Patent
Kaplan et al.

(10) Patent No.: US 10,864,299 B2
(45) Date of Patent: Dec. 15, 2020

(54) ARTIFICIAL SILK BASED INNERVATED CORNEA

(71) Applicant: Trustees of Tufts College, Medford, MA (US)

(72) Inventors: David L. Kaplan, Concord, MA (US); Siran Wang, Medford, MA (US); Rachel Gomes, Medford, MA (US); Chiara Ghezzi, Medford, MA (US); Dana Cairns, Medford, MA (US)

(73) Assignee: TRUSTEES OF TUFTS COLLEGE, Medford, MA (US)

( * ) Notice: Subject to any disclaimer, the term of this patent is extended or adjusted under 35 U.S.C. 154(b) by 0 days.

(21) Appl. No.: 16/096,851

(22) PCT Filed: Apr. 27, 2017

(86) PCT No.: PCT/US2017/029812
§ 371 (c)(1),
(2) Date: Oct. 26, 2018

(87) PCT Pub. No.: WO2017/189832
PCT Pub. Date: Nov. 2, 2017

(65) Prior Publication Data
US 2019/0133752 A1 May 9, 2019

Related U.S. Application Data

(60) Provisional application No. 62/329,645, filed on Apr. 29, 2016.

(51) Int. Cl.
| | | |
|---|---|---|
| A61L 27/36 | (2006.01) | |
| A61L 27/38 | (2006.01) | |
| A61L 27/56 | (2006.01) | |
| C12N 5/071 | (2010.01) | |
| C12N 5/079 | (2010.01) | |
| C12N 5/0793 | (2010.01) | |

(52) U.S. Cl.
CPC ......... *A61L 27/3604* (2013.01); *A61L 27/383* (2013.01); *A61L 27/3813* (2013.01); *A61L 27/3891* (2013.01); *A61L 27/56* (2013.01); *C12N 5/0619* (2013.01); *C12N 5/0621* (2013.01); *C12N 5/0697* (2013.01); *A61L 2430/16* (2013.01); *C12N 2500/38* (2013.01); *C12N 2501/11* (2013.01); *C12N 2501/115* (2013.01); *C12N 2501/117* (2013.01); *C12N 2501/12* (2013.01); *C12N 2501/13* (2013.01); *C12N 2501/15* (2013.01); *C12N 2502/081* (2013.01); *C12N 2502/083* (2013.01); *C12N 2502/085* (2013.01); *C12N 2513/00* (2013.01); *C12N 2533/30* (2013.01); *C12N 2533/54* (2013.01); *C12N 2533/90* (2013.01); *C12N 2535/00* (2013.01); *C12N 2535/10* (2013.01)

(58) Field of Classification Search
CPC ............... A61L 27/3604; A61L 27/383; A61L 27/3813; C12N 5/0698; C12N 5/0619
See application file for complete search history.

(56) References Cited

U.S. PATENT DOCUMENTS

| | | |
|---|---|---|
| 4,806,355 A | 2/1989 | Goosen |
| 5,015,476 A | 5/1991 | Cochrum |
| 5,093,489 A | 3/1992 | Diamantoglou |
| 5,263,992 A | 11/1993 | Guire |
| 5,270,419 A | 12/1993 | Domb |
| 5,576,881 A | 11/1996 | Doerr |
| 5,902,800 A | 5/1999 | Green |
| 6,127,143 A | 10/2000 | Gunasekaran |
| 6,245,537 B1 | 6/2001 | Williams |
| 6,267,776 B1 | 7/2001 | O'Connell |
| 6,310,188 B1 | 10/2001 | Mukherjee |
| 6,325,810 B1 | 12/2001 | Hamilton |
| 6,337,198 B1 | 1/2002 | Levene |
| 6,372,244 B1 | 4/2002 | Antanavich |
| 6,379,690 B2 | 4/2002 | Blanchard |
| 6,387,413 B1 | 5/2002 | Miyata |
| 6,395,734 B1 | 5/2002 | Tang |
| 7,635,755 B2 | 12/2009 | Kaplan |
| 8,178,656 B2 | 5/2012 | Kaplan |
| 2003/0096409 A1* | 5/2003 | Yasumoto ........... A61L 27/3804 435/371 |

(Continued)

FOREIGN PATENT DOCUMENTS

| | | |
|---|---|---|
| WO | 2008150861 | 12/2008 |
| WO | 2011005381 | 1/2011 |

OTHER PUBLICATIONS

Li et al., "Silk fibroin-based scaffolds for tissue engineering", Frontiers of Materials Science, Sep. 2013, vol. 7, Issue 3, pp. 237-247 (Year: 2013).*
Park et al, International Journal of Biological Macromolecules, 2016, vol. 93, pp. 1567-1574. (Year: 2016).*
Wang et al, Journal Biomedical Materials Research, p. A, (May 25, 2015), vol. 103A, pp. 3339-3348. (Year: 2015).*
Muller L, et al. Corneal nerves: Structure, contents and function. Exp Eye Res 2003; 76:521-542.
Nishida T, et al. Differential contributions of impaired corneal sensitivity and reduced tear secretion to corneal epithelial disorders. Jpn J Ophthalmol 2012; 56:20-25.
Ofri, R., Intraocular pressure and glaucoma. Veterinary Clinics of North America: Exotic Animal Practice, 2002. 5(2): pp. 391-406.

(Continued)

*Primary Examiner* — Allison M Fox
(74) *Attorney, Agent, or Firm* — Quarles & Brady, LLP

(57) ABSTRACT

In some embodiments, the present invention provides tissue compositions including a first silk scaffold comprising a plurality of epithelial cells, a second silk scaffold comprising a plurality of stromal cells, and a plurality of neurons. In some embodiments, provided compositions can function as physiologically relevant corneal model systems for, inter alia, testing of therapeutics for corneal disease and/or injury and production of functional corneal tissue (e.g., for transplant, etc). The present invention also provides methods for making and using provided compositions.

16 Claims, 26 Drawing Sheets

(56) References Cited

U.S. PATENT DOCUMENTS

| | | | |
|---|---|---|---|
| 2010/0178304 A1 | 7/2010 | Wang | |
| 2010/0191328 A1* | 7/2010 | Kaplan | A61L 27/3604 |
| | | | 623/5.11 |
| 2011/0171239 A1 | 7/2011 | Kaplan | |
| 2014/0370094 A1 | 12/2014 | Wray | |

OTHER PUBLICATIONS

Okada, Y., et al, Neurotrophic keratopathy; its pathophysiology and treatment. Histology and histopathology, 2010. 25(4): p. 771.
Orssengo, G.J. et al, Determination of the true intraocular pressure and modulus of elasticity of the human cornea in vivo. Bulletin of mathematical biology, 1999. 61(3): pp. 551-572.
Orwin, E. et al. "Bioreactor design for cornea tissue engineering: Material—cell interactions." Acta biomaterialia 3, No. 6 (2007): 1041-1049.
Pascolini, D. et al, Global estimates of visual impairment: 2010. British Journal of Ophthalmology, 2011: p. bjophthalmol-2011-300539.
Reichl, S., et al. "Human corneal equivalent as cell culture model for in vitro drug permeation studies." British journal of ophthalmology 88.4 (2004): 560-565.
Rockwood, D.N., et al, Materials fabrication from Bombyx mori silk fibroin. Nature protocols, 2011. 6(10): pp. 1612-1631.
Roeder, B.A., et al, Tensile mechanical properties of three-dimensional type I collagen extracellular matrices with iaried microstructure. Journal of biomechanical engineering, 2002. 124(2): pp. 214-222.
Sajanti J, et al. Increase of collagen synthesis and deposition in the arachnoid and the dura following subarachnoid hemorrhage in the rat. Biochim Biophys Acta 1999; 1454:209-216.
Semeraro, F., et al, Neurotrophic keratitis. 3. Ophthalmologica, 2014. 231(4): pp. 191-197.
Shaheen, B.S., et al, Corneal nerves in health and disease. Survey of ophthalmology, 2014.59(3): pp. 263-285.
Suuronen, E.J., et al, Functional innervation in tissue engineered models for in vitro study and testing purposes. Toxicological Sciences, 2004. 82(2): pp. 525-533.
Suuronen, E.J., et al, Innervated human corneal equivalents as in vitro models for nerve-target cell interactions. The FASEB journal, 2004. 18(1): pp. 170-172.
Tang-Schomer, M.D., et al, Bioengineered functional brainlike cortical tissue. Proceedings of the National Academy of Sciences, 2014. 111(38): pp. 13811-13816.
Tegtmeyer, S., et al, Reconstruction of an in vitro cornea and its use for drug permeation studies from different formulations containing pilocarpine hydrochloride. European journal of pharmaceutics and biopharmaceutics, 2001. 51(2): pp. 119-125.
Tucker K, et al. Neurotrophins are required for nerve growth during development. Nat Neurosci 2001;4:29-37.
Vitale P, et al. Mechanisms of transcriptional activation of the col6a1 gene during Schwann cell differentiation. Mech Dev 2001;102:145-156.
Wang X, et al. Sonication-induced gelation of silk fibroin for cell encapsulation. Biomaterials 2008; 29:1054-1064.
Wang, S., et al. "In vitro 3D corneal tissue model with epithelium, stroma, and innervation." Biomaterials 112 (2017): 1-9.
Whitcher, J.P., et al, Corneal blindness: a global perspective. Bulletin of the World Health Organization, 2001. 79(3): pp. 214-221.
Wilkins A, et al. Oligodendrocytes promote neuronal survival and axonal length by distinct intracellular mechanisms: A novel role for oligodendrocytederived glial cell line-derived neurotrophic factor. J Neurosci 2003; 23:4967-4974.
Willits R, et al. Effect of collagen gel stiffness on neurite extension. J Biomater Sci Polym Ed 2004; 15:1521-1531.
Wu J, et al. Bioengineering organized, multilamellar human corneal stromal tissue by growth factor supplementation on highly aligned synthetic substrates. Tissue Eng Part A 2013; 19:2063-2075.
Wu, J., et al, Corneal stromal bioequivalents secreted on patterned silk substrates. Biomaterials, 2014. 35(12): pp. 3744-3755.
Wu, J., et al, Corneal stromal stem cells versus corneal fibroblasts in generating structurally appropriate corneal stromal tissue. Experimental eye research, 2014. 120: pp. 71-81.
Yao, D., et al, Salt-leached silk scaffolds with tunable mechanical properties. Biomacromolecules, 2012. 13(11): pp. 3723-3729.
Yoon K, et al. Application of umbilical cord serum eyedrops for the treatment of neurotrophic keratitis. Ophthalmology 2007; 114:1637-1642.
You, L., et al, Glial Cell—Derived Neurotrophic Factor (GDNF)—Induced Migration and Signal Transduction in Corneal Epithelial Cells. Investigative ophthalmology & visual science, 2001. 42(11): pp. 2496-2504.
You, L., et al, Neurotrophic factors in the human cornea. Investigative Ophthalmology and Visual Science, 2000. 41(3): pp. 692-702.
Zeng, Y., et al, A comparison of biomechanical properties between human and porcine cornea. Journal of biomechanics, 2001. 34(4): pp. 533-537.
Acharya, C., et al. "Performance evaluation of a silk protein-based matrix for the enzymatic conversion of tyrosine to L-DOPA." Biotechnology Journal: Healthcare Nutrition Technology 3.2 (2008): 226-233.
Al-Aqaba, M.A., et al, Architecture and distribution of human corneal nerves. British Journal of Ophthalmology, 2010. 94(6): pp. 784-789.
Amsden, J.J., et al, Rapid nanoimprinting of silk fibroin films for biophotonic applications. Advanced Materials, 2010. 22(15): pp. 1746-1749.
Bae J, et al. Bone marrow-derived mesenchymal stem cells promote neuronal networks with functional synaptic transmission after transplantation into mice with neurodegeneration. Stem cells (Dayton, Ohio). 2007; 25:1307-1316.
Bayraktar, O, et al. "Silk fibroin as a novel coating material for controlled release of theophylline." European Journal of Pharmaceutics and Biopharmaceutics 60.3 (2005): 373-381.
Blanco-Mezquita, T., et al, Nerve Growth Factor Promotes Corneal Epithelial Migration by Enhancing Expression of Matrix Metalloprotease-9NGF Promotes Epithelial Migration. Investigative ophthalmology & visual science, 2013. 54(6): pp. 3880-3890.
Bryce, G. et al, Culture of isolated embryonic chick dorsal root ganglia at an airliquid interface: A simple method for studying the mechanism and control of neurite outgrowth. Journal of neuroscience methods, 1993. 48(1): pp. 89-97.
Hang, J.-E., et al, Air-interface condition promotes the formation of tight corneal epithelial cell layers for drug transport studies. Pharmaceutical research, 2000. 17(6): pp. 670-676.
Hen, C.-C., et al, A sensory neuron-specific, proton gated ion channel. Proceedings of the National Academy of Sciences, 1998. 95(17): pp. 10240- 10245.
Chernousov MA, et al. Schwann cell type V collagen inhibits axonal outgrowth and promotes Schwann cell migration via distinct adhesive activities of the collagen and noncollagen domains. J Neurosci 2001; 21:6125-6135.
Coulombre, A.J. et al, The role of intraocular pressure in the development of the chick eye: IV. Corneal curvature. AMA archives of ophthalmology, 1958. 59(4): pp. 502-506.
Daud M, et al. An aligned 3D neuronal-glial co-culture model for peripheral nerve studies. Biomaterials 2012; 33:5901-5913.
Delmonte, D.W. et al, Anatomy and physiology of the cornea. Journal of Cataract & Refractive Surgery, 2011. 37(3): pp. 588-598.
Demura, M. et al. "Immobilization of glucose oxidase with Bombyx mori silk fibroin by only stretching treatment and its application to glucose sensor." Biotechnology and bioengineering 33.5 (1989): 598-603.
Du Y, et al. Multipotent stem cells in human corneal stroma. Stem cells (Dayton, Ohio) 2005; 23:1266-1275.
Du, Y., et al, Secretion and organization of a cornea-like tissue in vitro by stem cells from human corneal stroma. Investigative ophthalmology & visual science, 2007. 48(11): pp. 5038- 5045.

(56) References Cited

OTHER PUBLICATIONS

Egholm, M, et al. "Peptide nucleic acids (Pna). Oligonucleotide analogs with an achiral peptide backbone." Journal of the American Chemical Society 114.5 (1992): 1895-1897.
Egholm, M., et al. "Pna hybridizes to complementary oligonucleotides obeying the Watson—Crick hydrogen-bonding rules." Nature 365.6446 (1993): 566-568.
Elsheikh, A., et al, Assessment of corneal biomechanical properties and their variation with age. Current eye research, 2007.32(1): pp. 11-19.
Fagerholm P, et al. Stable corneal regeneration four years after implantation of a cell-free recombinant human collagen scaffold. Biomaterials 2014; 35:2420-2427.
Fan C, et al. Effect of type-2 astrocytes on the viability of dorsal root ganglion neurons and length of neuronal processes. Neural Regen Res 2014; 9:119-128.
Foster T, et al. Platelet-rich plasma: from basic science to clinical applications. Am J Sports Med 2009; 37:2259-2272.
Gil E, et al. Helicoidal multi-lamellar features of RGD-functionalized silk Biomaterials for corneal tissue engineering. Biomaterials 2010; 31:8953-8963.
Gil E, et al. Response of human corneal fibroblasts on silk film surface patterns. Macromol Biosci 2010; 10:664-673.
Gingras, M., et al, In vitro development of a tissue-engineered model of peripheral nerve regeneration to study neurite growth. The FASEB journal, 2003. 17(14): pp. 2124-2126.
He, J., et al, Mapping the entire human corneal nerve architecture. Experimental eye research, 2010. 91(4): pp. 513-523.
Heigle T, et al. Aqueous tear production in patients with neurotrophic keratitis. Cornea 1996; 15:135-138.
Hicks C, et al. Keratoprostheses: Advancing toward a true artificial cornea. Sury Ophthalmol 1997; 42:175-189.
Hofmann, S., et al. "Silk fibroin as an organic polymer for controlled drug delivery." Journal of Controlled Release 111.1-2 (2006): 219-227.
Holly, F. et al, Tear physiology and dry eyes. Survey of ophthalmology, 1977. 22(2): pp. 69-87.
Hopkins A, et al. Silk hydrogels as soft substrates for neural tissue engineering. Adv Funct Mater 2013; 23:5140-5149.
Hu X, et al. Regulation of silk material structure by temperature-controlled water vapor annealing. Biomacromolecules 2011; 12:1686-1696.
Hubert T, et al. Collagens in the developing and diseased nervous system. Cell Mol Life Sci 2009; 66:1223-1238.
International Searching Authority, International Search Report and Written Opinion for Application PCT/US2017/029812, dated Jul. 21, 2017, 9 pages.
Jin, H.J., et al, Water- Stable Silk Films with Reduced R-Sheet Content. Advanced Functional Materials, 2005. 15(8): pp. 1241-1247.
Kaselis A, et al. DRG axon elongation and growth cone collapse rate induced by Sema3A are differently dependent on NGF concentration. Cell Mol Neurobiol 2014; 34:289-296.
Kowtharapu B, et al. Corneal epithelial and neuronal interactions: Role in wound healing. Exp Eye Res 2014; 125:53-61.
Lambiase, A., et al, Corneal changes in neurosurgically induced neurotrophic keratitis. JAMA ophthalmology, 2013. 131(12): p. 1547-1553.
Leclere, P.G., et al, Impaired axonal regeneration by isolectin B4-binding dorsal root ganglion neurons in vitro. The Journal of neuroscience, 2007. 27(5): pp. 1190-1199.
Letsinger, et al. "Nucleotide chemistry. XVI. Phosporamidate analogs of oligonucleotides." The Journal of organic chemistry 35.11 (1970): 3800-3803.
Lindsay R. Nerve growth factors (NGF, BDNF) enhance axonal regeneration but are not required for survival of adult sensory neurons. J Neurosci 1988; 8:2394-2405.
Lu, Q., et al. "Water-insoluble silk films with silk I structure." Acta biomaterialia 6.4 (2010): 1380-1387.
Lu, S., et al. "Stabilization of enzymes in silk films." Biomacromolecules 10.5 (2009): 1032-1042.
Madduri, S., et al, Synergistic effect of GDNF and NGF on axonal branching and elongation in vitro. Neuroscience research, 2009. 65(1): pp. 88-97.
Marfurt, C.F., et al, Anatomy of the human corneal innervation. Experimental eye research, 2010. 90(4): pp. 478-492.
McMenamin, P.G., et al, Cornea: anatomy, physiology and healing. Excimer lasers in Ophthalmology. London: Martin Dunitz, 1997: pp. 41-63.
Meier, C. et al. "Peptide Nucleic Acids (PNAs)—Unusual Properties of Nonionic Oligonucleotide Analogues." Angewandte Chemie International Edition in English 31.8 (1992): 1008-1010.
Meijering E, et al. Design and validation of a tool for neurite tracing and analysis in fluorescence microscopy images. Cytometry A 2004; 58:167-176.
Miyairi, S. et al. "Properties of 13-Glucosidase Immobilized in Serichin Membrane." Journal of fermentation technolog 56.4 (1978): 303-308.
Moore K, et al. Immobilized concentration gradients of neurotrophic factors guide neurite outgrowth of primary neurons in macroporous scaffolds. Tissue Eng 2006; 12:267-278.

* cited by examiner

ARTIFICIAL SILK BASED INNERVATED CORNEA

CROSS-REFERENCE TO RELATED APPLICATIONS

This application represents the national stage entry of PCT/US2017/029812, filed Apr. 27, 2017, which claims benefit of U.S. Provisional Patent Application 62/329,645 filed Apr. 29, 2016. The contents of this application are hereby incorporated by reference as set forth in their entirety herein.

GOVERNMENT LICENSE RIGHTS

This invention was made with government support under grants EB002520 and EY020856 awarded by the National Institutes of Health. The government has certain rights in the invention.

BACKGROUND

The cornea is the outermost layer of the human eye and is an important part of the ocular light path. The cornea has three distinct layers: the epithelium, stroma, and endothelium. The external epithelial layer has 3-5 layers of epithelial cells and protects the inner structures. The middle stromal layers are composed of aligned corneal stromal cells guided by parallel collagen lamellae. The innermost layer of the cornea is the endothelial layer. Current tissue models fail to incorporate each of these distinct anatomical layers and are not able to realize disease conditions of corneal tissue. Corneal opacity is one of the principal causes of bilateral blindness, affecting 7 million people around the world. Among them, 2.85 million people have diminished or an absence of sensation due to corneal nerve dysfunction or degeneration. Every year 46,000 patients receive corneal transplantation surgery.

SUMMARY

The present invention provides, among other things, new and unexpectedly powerful corneal tissue model systems and methods for making and using them. The interactions between corneal nerve, epithelium, and stroma are essential for maintaining a healthy cornea. Thus, corneal tissue models that more fully mimic the anatomy, mechanical properties and cellular components of corneal tissue would provide useful systems to study cellular interactions, diseases and provide options for drug screening. As provided herein, exemplary corneal tissue models were constructed to include the stroma, epithelium, and innervation. For some of the specific non-limiting examples herein, thin silk film stacks served as the scaffolding to support the corneal epithelium and stromal layers while a surrounding silk porous sponge supported neuronal growth. The neurons innervated the stroma and epithelium layers and improved function and viability of these two layers. The unique air-liquid interface environment of the corneal tissue was also mimicked in certain provided in vitro compositions, resulting in a positive impact on epithelium maturity. The inclusion of three cell types and co-cultures at an air-liquid interface advances the field of in vitro corneal tissue engineering to permit the study of innervation and corneal tissue development beyond that achievable using prior systems and methods.

In some embodiments, the present invention provides tissue compositions including a first silk scaffold comprising a plurality of epithelial cells, a second silk scaffold comprising a plurality of stromal cells, and a plurality of neurons. In some embodiments, provided compositions can function as physiologically relevant corneal model systems for, inter alia, testing of therapeutics for corneal disease and/or injury and production of functional corneal tissue (e.g., for transplant, etc).

In accordance with various embodiments, the present invention also provides methods of making a tissue composition including the steps of providing a first silk scaffold comprising a plurality of epithelial cells, associating a second silk scaffold comprising a plurality of stromal cells with the first silk scaffold to form a silk scaffold stack, and introducing a plurality of nerve cells to the silk scaffold stack to form a tissue composition, wherein at least some of the plurality of neurons innervate at least one of: a portion of the epithelial cells, and a portion of the stromal cells.

In accordance with a variety of embodiments, provided compositions may be in any application-appropriate configuration. For example, in some embodiments, the plurality of nerve cells are present in a third silk scaffold. In some embodiments, the third silk scaffold at least partially surrounds the first and second silk scaffolds. In some embodiments, the third silk scaffold may be or comprise a silk sponge.

In accordance with various embodiments, some provided methods and compositions include one or more porous components. For example, in some embodiments, one or more of the silk scaffolds is porous. In some embodiments, one or more silk scaffold has a porosity of at least 10% (e.g., at least 20%, 30%, 40%, 50%, 60%, 70% 80%, 90% or more). Without wishing to be held to a particular theory, it is contemplated that the presence of particular levels of porosity may be advantageous in facilitating cellular ingrowth, nutrient diffusion, and/or waste removal.

In contrast to many previously known corneal model systems, certain provided methods and compositions allow for functional innervation by a plurality of nerve cells of at least some of the epithelial and/or stromal cells present in a composition. This is important because it is well established that functional innervation is critical for corneal health. What was not well established prior to the present invention was how to accomplish such innervation in the context of an in vitro system. Accordingly provided methods and compositions include a plurality of nerve cells. In some embodiments, the nerve cells are human nerve cells. In some embodiments, the nerve cells are afferent (e.g., sensory) nerve cells. In some embodiments, the nerve cells innervate at least a portion of the epithelial cells and/or at least a portion of the stromal cells.

In accordance with various embodiments, any corneally relevant epithelial cell may be included in certain provided methods and compositions. In some embodiments, the epithelial cells are selected from the group consisting of stem cells, basal cells, wing cells, limbal epithelial cells, goblet cells, and squamous cells.

In accordance with various embodiments, any corneally relevant stromal cell may be included in certain provided methods and compositions. In some embodiments, the stromal cells comprise keratocytes and/or corneal stromal fibroblast cells.

One of the advantages of several embodiments of the present invention is the ability to use various growth factors to encourage cellular migration, differentiation and/or growth within and between portions of the composition. In some embodiments, at least one growth factor is added to at least one silk scaffold. In some embodiments, at least one growth factor is added to each silk scaffold. In some embodiments, the at least one growth factor is added prior to the addition of cells to the silk scaffold. In some embodiments, the at least one growth factor is substantially coated on coated on the at least one silk scaffold. In some embodiments, nerve growth factor is added to the first silk scaffold. In some embodiments, at least two growth factors (e.g., 3, 4, 5, 6, 7, 8, 9, 10 or more) are added to at least one silk scaffold. In some embodiments, at least one growth factor is added in a discrete pattern (see, for example FIG. 1).

In accordance with various embodiments, one or more silk scaffolds may be in any of a variety of forms. By way of non-limiting example, in some embodiments, at least one silk scaffold is selected from a silk film, a silk sponge, silk hydrogel and a silk-collagen mix hydrogel.

In accordance with various embodiments, some provided methods and compositions include exposing provided compositions to elevated pressure (e.g., pressure above 0 mmHg). The use of elevated pressures, in various embodiments, is contemplated to approximate intraocular pressure (IOP) that is present in vivo. In some embodiments, the composition is maintained under elevated pressure for a period of time. In some embodiments, the elevated pressure is between about 10-30 mmHg. In some embodiments, the elevated pressure is between about 15-20 mmHg.

In accordance with various embodiments, the addition of a tear-like fluid can enhance the physiological relevance of certain provided methods and compositions. As such, in some embodiments, provided method and compositions include one or more tear-like fluids. In some embodiments, the tear-like fluid is or comprises an aqueous solution including at least one lipid, at least one antibiotic, and at least one neurotrophic peptide. In some embodiments, the aqueous solution is or comprises saline. In some embodiments, the tear-like fluid is applied dropwise. In some embodiments, the tear-like fluid is applied as a mist or spray.

As is described herein, some provided methods and compositions include an air-liquid interface. While it is known that an air-liquid interface is important to maintain corneal epithelial function, previously known corneal models have not been able to implement an air-liquid interface (also referred to herein as an ALIC) in a satisfactory manner. In some embodiments, at least some of the epithelial cells are exposed to an air-liquid interface. Without wishing to be held to a particular theory, it is contemplated that exposure of provided compositions to simulated IOP and/or tear-like fluids in combination with an air-liquid interface provides significant advantages over previously known model systems.

In some embodiments, the present invention also provides compositions including a first silk film comprising a plurality of epithelial cells and at least one growth factor selected from the group consisting of nerve growth factor, glial cell-derived neurotrophic factor, and brain derived neurotrophic factor, a second silk film comprising a plurality of stromal cells, and a silk sponge comprising a plurality of human nerve cells, wherein the silk sponge surrounds the first and second silk films, and wherein the composition is subject to an elevated pressure between about 10-30 mmHg.

Any citations to publications, patents, or patent applications herein are incorporated by reference in their entirety. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWING

The Figures described below, that together make up the Drawing, are for illustration purposes only, not for limitation.

DEFINITIONS

Figure 1:
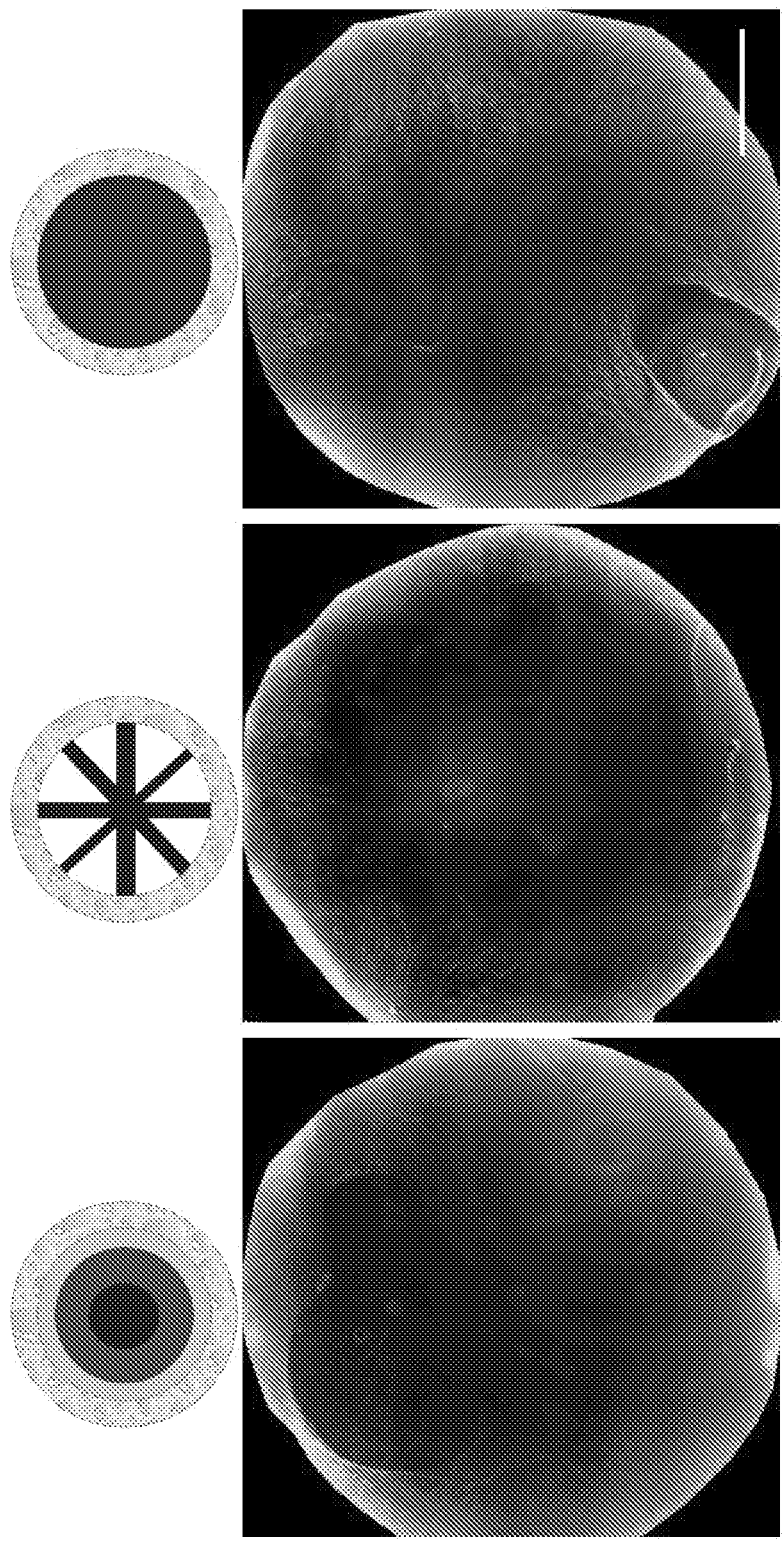
FIG. 1. Immunohistochemistry staining of axonal guidance generated by multi-circular (left), radial (middle) and uniform (right) stamped patterns. βIII tubulin was stained green. The uniform stamped patterns provided the strongest guidance and led to denser and longer innervation compared to the other two patterns. Images collected from n>3 from three independent experiments.

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) all numerical ranges provided herein are understood to include all possible incremental sub-ranges within the outer boundaries of the range. Thus, a range of 30 to 90 units discloses, for example, 35 to 50 units, 45 to 85 units, and 40 to 80 units, etc. In addition, endpoints of any ranges are included. Unless otherwise defined, percentages are wt/wt %.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

A: The singular terms "a," "an," and "the" include plural referents unless context clearly indicates otherwise. Similarly, the word "or" is intended to include "and" unless the context clearly indicates otherwise.

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Agent: In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety.

Comprises: Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Comprising: As used herein the term "comprising" or "comprises" is used in reference to compositions, methods, and respective component(s) thereof, that are useful to an embodiment, yet open to the inclusion of unspecified elements, whether useful or not.

Maintain: As used herein, the terms "maintaining," "maintain," and "maintenance," when referring to compositions or active agents mean keeping, sustaining, or retaining the bioactivity of at least one active agent in a provided composition, when the active agent is subjected to certain conditions. In some embodiments, one or more active agents distributed in a provided composition retains at least about 30% of its original bioactivity, including at least about 40%, at least about 50%, at least about 60%, at least about 70%, at least about 80%, at least about 90% of its original bioactivity or higher.

Nucleic acid: As used herein, the term "nucleic acid" or "oligonucleotide" or grammatical equivalents herein means at least two nucleotides, including analogs or derivatives thereof, which are covalently linked together. Exemplary nucleic acids include, but are not limited to, polynucleotides, oligonucleotides, genes, genes including control and termination regions, self-replicating systems such as viral or plasmid DNA, genomic DNA, cDNA, mRNA, pre-mRNA, single-stranded and double-stranded siRNAs and other RNA interference reagents (RNAi agents or iRNA agents), shRNA (short hairpin RNAs), antisense oligonucleotides, aptamers, ribozymes, microRNAs (miRNAs), pre-miRNA, and modified RNAs (e.g., locked nucleic acid). The nucleic acids can be single stranded or double stranded. The nucleic acid can be DNA, RNA or a hybrid, where the nucleic acid contains any combination of deoxyribo- and ribo-nucleotides, and any combination of uracil, adenine, thymine, cytosine and guanine. The nucleic acids can comprise one or more backbone modifications, e.g., phosphoramide (Beaucage et al., Tetrahedron 49(10):1925 (1993) and references therein; Letsinger, J. Org. Chem. 35:3800 (1970)), phosphorothioate, phosphorodithioate, O-methylphophoroamidite linkages (see Eckstein, Oligonucleotides and Analogues: A Practical Approach, Oxford University Press), or peptide nucleic acid linkages (see Egholm, J. Am. Chem. Soc. 114:1895 (1992); Meier et al., Chem. Int. Ed. Engl. 31:1008 (1992); and Nielsen, Nature, 365:566 (1993), content of all of which is herein incorporated by reference. The nucleic acids can also include modifications to nucleobase and/or sugar moietites of nucleotides. Exemplary sugar modifications at the sugar moiety include replacement of 2'-OH with halogens (e.g., fluoro), O-methyl, O-methoxyethyl, NH2, SH and S-methyl.

Solution: The term "solution" broadly refers to a homogeneous mixture composed of one phase. Typically, a solution comprises a solute or solutes dissolved in a solvent or solvents. It is characterized in that the properties of the mixture (such as concentration, temperature, and density) can be uniformly distributed through the volume. In the context of the present application, therefore, a "silk fibroin solution" refers to silk fibroin protein in a soluble form, dissolved in a solvent, such as water. In some embodiments, silk fibroin solutions may be prepared from a solid-state silk fibroin material (i.e., silk matrices), such as silk films and other scaffolds. Typically, a solid-state silk fibroin material is reconstituted with an aqueous solution, such as water and a buffer, into a silk fibroin solution. It should be noted that liquid mixtures that are not homogeneous, e.g., colloids, suspensions, emulsions, are not considered solutions. To give but one example, silk fibroin microspheres or particles suspended in a solution do not themselves constitute a silk fibroin solution.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

DETAILED DESCRIPTION OF CERTAIN EMBODIMENTS

The present invention provides, inter alia, new methods and systems for modeling a human cornea including complex multicellular compositions with previously unattained levels of functional innervation. Provided herein are non-limiting examples of provided compositions and systems as well as methods for making and using those compositions and systems.

The Cornea

The cornea is the transparent outermost part of the human eye, and accounts for approximately two-thirds of the eye's optical power. Typically, the human cornea has a thickness between 0.5-0.6 mm the center, and 0.6-0.8 mm around the periphery with a diameter of generally about 11-12 mm. The cornea has three distinct layers, the epithelium, stroma and endothelium. The corneal epithelium is the outermost layer of the cornea and contributes approximately 10% of the total corneal thickness. The epithelial layer comprises a superficial layer formed with flattened apical cells, 4-5 layers of stratified non-keratinized epithelial cells, and a basal layer. In vivo, these cell layers are held together by tight junctions and serve as a barrier against fluid loss and pathogen penetration. The corneal epithelial cell surface contains microvilli that secrete a polysaccharide-protein mixture, adhering and stabilizing the tear film, while the basal cells secrete basal lamina attaching epithelium to stroma.

In between the native corneal epithelium and stroma is an acellular layer composed with collagen, laminin, nidogen and perlecan, named the Bowman's layer. In vivo, this layer mainly serves to protect the stroma. In some embodiments, provided compositions may further include a silk scaffold which approximates this acellular layer, for example, by comprising silk fibroin, and any combination of collagen, laminin, nidogen and/or perlecan. However, in some provided compositions, this layer is not necessarily acellular as it can serve to support epithelial growth and/or nerve guidance within and through the layer(s).

Typically, the corneal stroma accounts for 85-90% of the corneal thickness and consists of regularly arranged collagen fibers along with sparsely distributed interconnected keratocytes. These cells produce collagen and proteoglycans that comprise the corneal extracellular matrix. Corneal ECM is known to be especially rich in collagens. Collagen types I, V and VI compose the majority of corneal stroma. The cornea also contains proteoglycans including decorin, lumican, mimecan, keratocan, and keratin sulfate. These proteoglycans participate in, inter alia, the control of inter-fibrillar spacing and in lamellar adhesion. The stromal collagen fibrils are organized into lamellae which form approximately 300 layers in central cornea and 500 close to limbus. The anterior stromal lamellae interweave through layers, directly insert into Bowman's layer, and contribute to corneal curvature. Posterior stroma lamellae are wider, thicker, more ordered and more hydrated than in the anterior stroma. In the posterior lamellae, keratocytes are arranged parallel to the plane of corneal curvature. Proteoglycan and keratoepithelin are expressed between the collagen fibrils to bind collagen lamellae together.

The endothelial layer typically consists of a monolayer of cells that lines the posterior corneal surface which contain 3500 cells/mm². In the adult, endothelial cells are not known to proliferate under normal circumstances and mainly serve as an active pump that moves ions and draws water osmotically from stroma into aqueous humour. This pumping mechanism maintains the transparency of cornea and allows nutrients to permeate from the aqueous humour into the stroma.

In addition, the cornea is the most peripherally innervated surface in the human body. Neuronal innervation is known to be closely related to the health or disease state of the corneal epithelium and stroma. In vivo, innervation is distributed throughout the epithelium and stroma layers but is absent in the endothelial layer. Stromal nerve trunks with a density of 33-71/mm$^2$ arise from the limbal plexus and enter the peripheral corneal stroma radially. In the stroma, nerves are organized parallel to the collagen lamellae and branch into smaller fascicles as they proceed toward the superficial stroma. The nerve fibers then penetrate the epithelium layer with a density of approximately 600 terminals/mm$^2$. The nerves interact physically and chemically with corneal tissue, providing sensing and releasing trophic factors including neurotransmitters and neuropeptides to maintain homeostasis. During corneal development, nerve growth is modulated by many growth factors. Brain derived nerve growth factor (BDNF), nerve growth factor (NGF), glial cell derived neurotrophic factor (GDNF), and neurotrophic (NT-3) are expressed in the corneal epithelium and stroma. Among these growth factors, NGF is critical for corneal nerve survival, axonal branching, elongation, sprouting and regeneration. The lack of these trophic factors can lead to neurotrophic keratopathy.

Despite the importance of corneal innervation, the role of the neurons in the healthy and diseased cornea are not fully understood. This is partially due to the limitations with rabbit, mice, pig and human in vivo models, including the complexity of the in vivo environments, differences between human and animal corneal tissues, and the challenges with studying human embryo cornea. Accordingly, one of the advantages of some embodiments is that provided compositions overcome some or all of these previously insurmountable limitations.

In vitro corneal tissue models have unique advantages for studying cellular interactions including the ability to simplify the complex in vivo environment, utilize human cells, be cost effective when compared with animal and human studies, and be designed for high throughput analysis. Provided in vitro tissue models of human corneal innervation can also support studies of corneal nerve functions. Previously known corneal tissue in vitro models mainly focus on corneal epithelium and stromal cells and use collagen as substrates. Among the few co-culture studies that used corneal cells and neurons, layers of collagen hydrogel were used to resemble the lamellar structure of cornea but failed to recapitulate the alignment of the stromal cells and the multi-layer features of the epithelial cells. Further, the native density of nerve endings and branches has also not been achieved through previously known in vitro cultures. Collagen as the substrate also poses significant limitations due to low stiffness leading to mismatched mechanical properties and contraction in long-term culture, thus precluding extended maintenance of such substrates.

Silk Fibroin

In contrast to previously known corneal model systems, provided compositions and systems use silk as a component of provided substrates. Silk is a biodegradable protein material with highly tunable mechanical properties that can be cast into optically clear films. Silk films, physically cross-linked through water vapor annealing, are able to provide elastic moduli of 67.7 kPa that matches the stiffness of the cornea, which is ~70 kPa. Silk films with surface patterns and functionalized with RGD can support the alignment and growth of human corneal stromal cells (hCSCs). Typically, these films also do not contract and slowly degrade in vitro, and are thus able to provide support for sustained in vitro tissue models. Silk can also be formed into sponges which can support neuron growth and the formation of neuronal connections.

As provided herein, some embodiments of the compositions and systems exemplified below illustrate the generation of three dimensional silk protein based co-culture systems including the corneal stromal layer, epithelial layer, and DRG neurons, allowing for further understanding of the interactions between corneal innervation and corneal tissues. In some embodiments, design of certain scaffolds closely mimicked native corneal anatomy, with silk film stacks for corneal epithelial and stromal cell growth surrounded by a silk sponge seeded with DRG simulating limbus tissue. In some embodiments, guidance for neuronal extensions (e.g., between and through various layers) was generated by the addition of NGF in the epithelial layer scaffold. Further, in some embodiments, an air-liquid interface may be designed for a bioreactor support system to house the corneal tissues and to better mimic the native cornea environment. As shown in the provided examples, in some embodiments, provided corneal tissue systems are able to support dense innervation in the epithelium and stroma regions.

In accordance with several embodiments, provided compositions (and silk scaffolds therein) include degummed silk, or silk fibroin. As used herein, the term "fibroin" includes, but is not limited to, silkworm fibroin and insect or spider silk protein. In some embodiments, fibroin is obtained from a solution containing a dissolved silkworm silk or spider silk. In some embodiments silkworm silk protein is obtained, for example, from *Bombyx mori*, and spider silk is obtained from *Nephila clavipes*. In some embodiments, silk proteins suitable for use in the present invention may be obtained from a solution containing a genetically engineered silk, such as from bacteria, yeast, mammalian cells, transgenic animals or transgenic plants. See, for example, WO 97/08315 and U.S. Pat. No. 5,245,012. In some embodiments, provided silk scaffolds and compositions include no sericin, or substantially no sericin.

In accordance with various embodiments, silk scaffolds may be made from silk solutions (e.g., aqueous silk solutions). Silk fibroin solutions used in methods and compositions described herein may be obtained from a solution containing a dissolved silkworm silk, such as, for example, from *Bombyx mori*. Alternatively, a silk fibroin solution is obtained from a solution containing a dissolved spider silk, such as, for example, from *Nephila clavipes*. Silk fibroin solutions can also be obtained from a solution containing a genetically engineered silk. Genetically engineered silk can, for example, comprise a therapeutic agent, e.g., a fusion protein with a cytokine, an enzyme, or any number of hormones or peptide-based drugs, antimicrobials and related substrates.

Provided compositions described herein, and methods of making and/or using them may be performed in the absence of any organic solvent. Thus, in some embodiments, provided compositions and methods are particularly amenable to the incorporation of labile molecules, such as bioactive agents or therapeutics, and can, in certain embodiments, be used to produce controlled release biomaterials, for example, between silk scaffolds or other components of provided compositions. In some embodiments, such methods are performed in water only, or substantially in water only.

A silk fibroin solution can be prepared by any conventional method known to one skilled in the art. According to various embodiments, the solution is an aqueous solution. By way of non-limiting example, B. mori cocoons are boiled for about 30 minutes in an aqueous solution. In some embodiments, the aqueous solution is about 0.02M $Na_2CO_3$, and cocoons are rinsed, for example, with water to extract the sericin proteins and the extracted silk is then dissolved in an aqueous salt solution. Exemplary salts useful for this purpose include, but are not limited to, lithium bromide, lithium thiocyanate, calcium nitrate, and/or other chemicals capable of solubilizing silk. In some embodiments, extracted silk is dissolved in about 9-12 M LiBr solution, and the salt is consequently removed using, for example, dialysis.

In some embodiments, silk compositions (e.g., solutions, scaffolds, etc) comprising low molecular weight silk fragments may be used. Native silk fibroin has a molecular weight of approximately 300-350 kDa, but it is known that reducing fibroin into smaller fragment can provide advantages in some application, for example, in stabilizing certain material (e.g., blood, certain active agents, etc) and also with regard to solubility and resolubility. As used herein, the term "low molecular weight silk" means silk fragments of less than 200 kDa. In some embodiments, a low molecular weight silk fibroin composition comprises a population of silk fibroin fragments having a range of molecular weights, characterized in that: no more than 15% of total number of the silk fibroin fragments in the population has a molecular weight exceeding 200 kDa, and at least 50% of the total number of the silk fibroin fragments in the population has a molecular weight within a specified range, wherein the specified range is between about 3.5 kDa and about 120 kDa. In some embodiments, a low molecular weight silk composition comprises silk fibroin fragments of less than 120 kDa and substantially no fragments larger than that. In some embodiments, a low molecular weight silk composition comprises silk fibroin fragments of less than 100 kDa (e.g., 90 kDa, 85 kDa, 80 kDa, 75 kDa, 70 kDa, 65 kDa, 60 kDa, 55 kDa, 50 kDa, 45 kDa, 40 kDa, 35 kDa, 30 kDa, 25 kDa, 20 kDa, or less) and substantially no fragments larger than that. In some embodiments, a composition having substantially no fragments larger than a particular size includes no more than 5% wt (e.g., less than 1% or 0%) of fragments exceeding the designated size. For example, in some embodiments wherein a provided composition comprises low molecular weight silk having a molecular weight of less than 100 kDa and substantially no fragments larger than that, the composition would include no more than 5% wt of silk fibroin fragments having a molecular weight of greater than 100 kDa. In some embodiments, silk fibroin fragments having a molecular weight distribution with a specified range as described above can exhibit a continuous or discrete molecular weight distribution. As used herein, the term "continuous molecular weight distribution" refers to a distribution of molecular weight having any sub-ranges between a specified range. As used herein, the term "discrete molecular weight distribution" refers to a distribution of molecular weight having certain sub-ranges between the specified range. By way of example only, silk fibroin fragments having a discrete molecular weight distribution with the specified range between about 3.5 kDa and about 120 kDa, or between about 5 kDa and about 100 kDa, for example, can refer to a population of the silk fibroin fragments, in which some of the silk fibroin fragments have a molecular weight between about 3.5 kDa and 10 kDa, while at least some or the rest of the silk fibroin fragments have a molecular weight between about 80 kDa and about 100 kDa.

Accordingly, in some embodiments, at least about 50% or higher of the total number (or total moles) or total weight of silk fibroin fragments in the population having a molecular weight within the specific range between 3.5 kDa and 120 kDa, or between about 5 kDa and about 125 kDa can be characterized as a population of the silk fibroin fragments, in which at least about 50% of the total number (or total moles) or total weight of the silk fibroin fragments in the population having a molecular weight within the specific range is comprised by one or more (e.g., 1, 2, 3, 4, 5, 6, 7, 8, 9, 10) of the following sub-ranges (i)-(x), which include: (i) silk fibroin having a molecular weight distribution of 20 kDa to 30 kDa; (ii) silk fibroin having a molecular weight distribution of 30 kDa to 40 kDa; (iii) silk fibroin having a molecular weight distribution of 40 kDa to 50 kDa; (iv) silk fibroin having a molecular weight distribution of 50 kDa to 60 kDa; (v) silk fibroin having a molecular weight distribution of 60 kDa to 70 kDa; (vi) silk fibroin having a molecular weight distribution of 70 kDa to 80 kDa; (vii) silk fibroin having a molecular weight distribution of 80 kDa to 90 kDa; (viii) silk fibroin having a molecular weight distribution of 90 kDa to 100 kDa; (ix) silk fibroin having a molecular weight distribution of 40 kDa to 80 kDa; and (x) silk fibroin having a molecular weight distribution of 5 kDa to 80 kDa.

In some embodiments, the amount of silk fibroin fragments having a molecular weight sub-range (i) to (x) can vary from 0% to 100% of the total number (or total moles) or total weight of all of the silk fibroin fragments in the composition described herein, provided that the combined weight of the silk fibroin fragments having the molecular weight sub-ranges (i)-(x) makes up at least 50% or higher of the total number (or total moles) or total weight of all of the silk fibroin fragments in the composition. Accordingly, the low molecular weight silk fibroin compositions described herein can be configured to have any combinations of the silk fibroin fragments having the molecular weight sub-range (i) to (x). In some embodiments, the low molecular weight silk fibroin compositions can have silk fibroin fragments corresponding to one specific molecular weight sub-range defined herein. In other embodiments, the low molecular weight silk fibroin composition can have a mixture of silk fibroin fragments corresponding to two or more specific molecular weight sub-ranges defined herein.

In some embodiments, silk fibroin fragments can be derived by degumming silk cocoons at or close to (e.g., within 5% around) an atmospheric boiling temperature for at least about 60 minutes or longer, including, e.g., at least 70 minutes, at least 80 minutes, at least 90 minutes, at least 100 minutes, at least 110 minutes, at least about 120 minutes or longer (e.g., 180 minutes or longer). As used herein, the term "atmospheric boiling temperature" refers to a temperature at which a liquid boils under atmospheric pressure.

In some embodiments, low molecular weight silk fibroin fragments can be produced by degumming silk cocoons in an aqueous solution at about 90° C.-about 110° C. for at least 60 minutes or longer, including, e.g., at least 70 minutes or longer. In some embodiments, the silk fibroin fragments can be derived by degumming silk cocoons below an atmospheric boiling temperature for a longer period of time, e.g., more than 60 minutes or longer, e.g., longer than 70 minutes, longer than 80 minutes, longer than 90 minutes, longer than 100 minutes, longer than 110 minutes, longer than 120 minutes, longer than 130 minutes, longer than 140 minutes, longer than 150 minutes, or longer.

In some embodiments, a silk solution may then be concentrated using, for example, dialysis against a hygroscopic polymer, for example, PEG, a polyethylene oxide, amylose or sericin. In some embodiments, PEG is of a molecular weight of 8,000-10,000 g/mol and has a concentration of 25-50%. In some embodiments, any dialysis system can be used. In some embodiments, dialysis may be for a time period sufficient to result in a final concentration of aqueous silk solution between 10-30%, for example, dialysis for 2-12 hours.

In accordance with various embodiments, a silk solution or silk scaffold may comprise any of a variety of concentrations of silk fibroin. In some embodiments, a silk solution or silk scaffold may comprise 0.1 to 30% by weight silk fibroin. In some embodiments, a silk solution or silk scaffold may comprise between about 0.5% and 30% (e.g., 0.5% to 25%, 0.5% to 20%, 0.5% to 15%, 0.5% to 10%, 0.5% to 5%, 0.5% to 1.0%) by weight silk fibroin, inclusive. In some embodiments, a silk solution or silk scaffold may comprise at least 0.1% (e.g., at least 0.5%, 1%, 2%, 3%, 4%, 5%, 6%, 7%, 8%, 9%, 10%, 15%, 20%, 25%) by weight silk fibroin. In some embodiments, a silk solution or silk scaffold may comprise at most 30% (e.g., at most 25%, 20%, 15%, 14%, 13%, 12% 11%, 10%, 5%, 4%, 3%, 2%, 1%) by weight silk fibroin.

In some embodiments, biocompatible polymers can also be added to the silk solution or silk scaffold to generate composite matrices in the methods and processes of the present invention. Exemplary biocompatible polymers useful in the present invention include, for example, polyethylene oxide (PEO) (U.S. Pat. No. 6,302,848), polyethylene glycol (PEG) (U.S. Pat. No. 6,395,734), collagen (U.S. Pat. No. 6,127,143), fibronectin (U.S. Pat. No. 5,263,992), keratin (U.S. Pat. No. 6,379,690), polyaspartic acid (U.S. Pat. No. 5,015,476), polylysine (U.S. Pat. No. 4,806,355), alginate (U.S. Pat. No. 6,372,244), chitosan (U.S. Pat. No. 6,310,188), chitin (U.S. Pat. No. 5,093,489), hyaluronic acid (U.S. Pat. No. 387,413), pectin (U.S. Pat. No. 6,325,810), polycaprolactone (U.S. Pat. No. 6,337,198), polylactic acid (U.S. Pat. No. 6,267,776), polyglycolic acid (U.S. Pat. No. 5,576,881), polyhydroxyalkanoates (U.S. Pat. No. 6,245,537), dextrans (U.S. Pat. No. 5,902,800), and polyanhydrides (U.S. Pat. No. 5,270,419). In some embodiments, two or more biocompatible polymers can be used.

In some embodiments, a conformational change can be induced in the silk fibroin in a provided composition to control the solubility and/or physical or mechanical properties of a provided silk scaffold and/or composition. In some embodiments, the conformational change can induce the silk fibroin at least partially insoluble. Without wishing to be bound by a theory, in some embodiments, it is contemplated that the induced conformational change alters the crystallinity of the silk fibroin, e.g., Silk II beta-sheet crystallinity. The conformational change can be induced by any application-appropriate methods known in the art, including, but not limited to, alcohol immersion (e.g., ethanol, methanol), water annealing, shear stress, ultrasound (e.g., by sonication), pH reduction (e.g., pH titration and/or exposure to an electric field) and any combinations thereof. For example, the conformational change can be induced by one or more methods, including but not limited to, controlled slow drying (Lu et al., Biomacromolecules 2009, 10, 1032); water annealing (Jin et al., 15 Adv. Funct. Mats. 2005, 15, 1241; Hu et al., Biomacromolecules 2011, 12, 1686); stretching (Demura & Asakura, Biotech & Bioengin. 1989, 33, 598); compressing; solvent immersion, including methanol (Hofmann et al., J Control Release. 2006, 111, 219), ethanol (Miyairi et al., J. Fermen. Tech. 1978, 56, 303), glutaraldehyde (Acharya et al., Biotechnol J. 2008, 3, 226), and 1-ethyl-3-(3-dimethyl aminopropyl) carbodiimide (EDC) (Bayraktar et al., Eur J Pharm Biopharm. 2005, 60, 373); pH adjustment, e.g., pH titration and/or exposure to an electric field (see, e.g., U.S. Patent App. No. US2011/0171239); heat treatment; shear stress (see, e.g., International App. No.: WO 2011/005381), ultrasound, e.g., sonication (see, e.g., U.S. Patent Application Publication No. U.S. 2010/0178304 and International App. No. WO2008/150861); and any combinations thereof. Contents of all of the references listed above are incorporated herein by reference in their entireties.

In some embodiments, provided silk scaffolds or compositions can be treated by annealing. As used herein, the process of annealing involves inducing formation of beta-sheet secondary structure in the silk fibroin. This can be due to increased non-covalent interactions of silk fibroin. Such non-covalent interactions can include intra-molecular interactions, inter-molecular interactions, or both. Typically, non-covalent interactions are mediated by hydrogen bonds, which lead to increased beta sheet formation. Upon reaching a certain critical level of beta sheet secondary structure, silk fibroin is rendered insoluble, e.g., in an aqueous environment. This phenomenon is generally referred to as crystallinity and the status of such silk fibroin is referred to as Silk II. Thus, "annealing" involves a conformation change of silk fibroin to beta-sheet dominated (silk II) conformation, such that silk fibroin is crystallized and thus insoluble. Without wishing to be bound by a theory, it is believed that this conformational change is due to hydrogen-bonding and/or hydrophobic interactions mediated structural shift of silk fibroin to a higher beta sheet content.

In some embodiments, the conformation of silk fibroin can be altered by water annealing. There are a number of different methods for water annealing. One method of water annealing involves treating solidified but soluble forms of silk fibroin with water vapor. Without wishing to be bound by a theory, it is believed that water molecules act as a plasticizer, which allows chain mobility of fibroin molecules to promote the formation of hydrogen bonds, leading to increased beta sheet secondary structure. This process is also referred to as "water vapor annealing" herein.

Without wishing to be bound by a theory, it is believed that physical temperature-controlled water vapor annealing (TCWVA) provides a simple and effective method to obtain refined control of the molecular structure of silk biomaterials. The silk materials can be prepared with control of crystallinity, from a low beta-sheet content using conditions at 4° C. (a helix dominated silk I structure), to higher beta-sheet content of ~60% crystallinity at 100° C. ((3-sheet dominated silk II structure). This physical approach covers the range of structures previously reported to govern crystallization during the fabrication of silk materials, yet offers a simpler, green chemistry, approach with tight control of reproducibility. Water or water vapor annealing is described, for example, in PCT application no. PCT/US2004/011199, filed Apr. 12, 2004 and no. PCT/US2005/020844, filed Jun. 13, 2005; and Jin et al., Adv. Funct. Mats. 2005, 15: 1241 and Hu et al., Biomacromolecules, 2011, 12(5): 1686-1696, contents of all of which are incorporated herein by reference in their entireties.

Another way of annealing is by slow, controlled evaporation of water from silk fibroin in the silk material/matrix. Slow, controlled, drying is described in, for example, Lu et al., Acta. Biomater. 2010, 6(4): 1380-1387.

The annealing step can be performed within a water vapor environment, such as in a chamber filled with water vapor, for different periods of time. Without wishing to be bound by a theory, length of annealing effects the amount of beta-sheet crystallinity obtained in silk fibroin within the silk-based material. Accordingly, typical annealing time periods can range from seconds to days. In some embodiments, the annealing is for a period of seconds to hours. For example, annealing time can range from a few seconds (e.g., about 5, 10, 15, 20, 25, 30, 35, 40, 45, 50, 55, or 60 seconds) to about 2, 6, 12, 24, 36, or 48 hours.

The temperature of the water vapor used in the annealing process effects the amount of beta-sheet crystallinity obtained. See Hu et al., Biomacromolecules, 12: 1686-1696. Accordingly, the annealing can be performed at any desired temperature. For example, the annealing can be performed with a water vapor temperature from about 4° C. to about 120° C. Optimal water vapor to obtain a required amount of beta-sheet crystallinity in silk fibroin within the silk-based material can be calculated based on equation (I):

$$C=a(1-\exp(-kT)) \quad (I)$$

wherein C is beta-sheet crystallinity, a is 62.59, k is 0.028 and T is annealing temperature. See Hu et al., Biomacromolecules, 12: 1686-1696.

Without wishing to be bound by a theory, the pressure under which the annealing takes place can also influence the degree or amount of beta-sheet crystallinity. In some embodiments, the contacting can be performed in a vacuum environment.

Relative humidity under which the annealing takes place can also influence the degree or amount of beta-sheet crystallinity. Relative humidity under which the silk-based material is contacted with water or water vapor can range from about 5% to 100%. For example, relative humidity can be from about 5% to about 95%, from about 10% to about 90%, or from about 15% to about 85%. In some embodiments, relative humidity is 90% or higher.

After the treatment to induce the conformational change, silk fibroin can comprise a silk II beta-sheet crystallinity content of at least about 5%, at least about 10%, at least about 20%, at least about 30%, at least about 40%, at least about 50%, at least about 60%, at least about 70%, at least about 80%, at least about 90%, or at least about 95% but not 100% (i.e., all the silk is present in a silk II beta-sheet conformation). In some embodiments, the silk fibroin in silk-based material comprises beta-sheet crystallinity of at least 10%, e.g., 15%, 20%, 25%, 30%, 35%, 40%, 45%, 50%, 55%, 60%, 65%, 70%, 75%, 70%, 85%, 90%, 95% or more, but not 100% (i.e., not all the silk fibroin is in a beta-sheet conformation).

In some embodiments, the present invention provides tissue compositions including a first silk scaffold comprising a plurality of epithelial cells, a second silk scaffold comprising a plurality of stromal cells, and a plurality of neurons. In some embodiments, provided compositions can function as physiologically relevant corneal model systems for, inter alia, testing of therapeutics for corneal disease and/or injury and production of functional corneal tissue (e.g., for transplant, etc).

In accordance with a variety of embodiments, provided compositions may be in any application-appropriate configuration. For example, in some embodiments, the plurality of nerve cells are present in a third silk scaffold. In some embodiments, the third silk scaffold at least partially surrounds the first and second silk scaffolds. In some embodiments, the third silk scaffold may be or comprise a silk sponge.

Silk Scaffolds

Any of a variety of silk scaffolds are contemplated as useful in accordance with various embodiments. In some embodiments, a silk scaffold may be a three dimensional structure comprising silk fibroin and a plurality of pores. In some embodiments, silk scaffolds may be arranged as a plurality of layers. In some embodiments, a silk scaffold may include regions having different physical or mechanical properties, different active agent(s) therein, and/or different cell types therein/thereon.

In some embodiments, silk scaffolds are characterized as having interconnected pores, biocompatibility, and/or pore sizes large enough to allow for cell growth. In some embodiments, a silk scaffold will have a configuration and/or pore size sufficient to allow for, by way of non-limiting example, the extension of neurons, such as into or through a first silk scaffold and/or a second silk scaffold.

In accordance with various embodiments, one or more silk scaffolds may be in any of a variety of forms. By way of non-limiting example, in some embodiments, at least one silk scaffold is selected from a silk film, a silk sponge, silk hydrogel and a silk-collagen mix hydrogel. In some embodiments, a silk scaffold is a silk film. In some embodiments, a silk scaffold is a silk sponge.

Epithelial Cells

In accordance with various embodiments, any corneally relevant epithelial cell may be included in certain provided methods and compositions. In some embodiments, the epithelial cells are selected from the group consisting of stem cells, basal cells, wing cells, limbal epithelial cells, goblet cells, and squamous cells.

In some embodiments, epithelial cells are provided in one or more discrete layers (e.g., silk scaffolds). In some embodiments, epithelial cells are provided in a plurality of layers (e.g., 2, 3, 4, 5, 6, 7 or more layers/silk scaffolds).

In some embodiments, epithelial cells present in provided compositions exhibit one or more markers of lineage or function consistent with epithelial cells in vivo. In some embodiments, the one or more markers may include one or more of involucrin (IVL), connexin 37 (GJA4), and cytokeratin-3 (KRT3).

Stromal Cells

In accordance with various embodiments, any corneally relevant stromal cell may be included in certain provided methods and compositions. In some embodiments, the stromal cells comprise stem cells, keratocytes and/or corneal stromal fibroblast cells.

In some embodiments, stromal cells present in provided compositions exhibit one or more markers of lineage or function consistent with stromal cells in vivo. In some embodiments, the one or more markers may include one or more of keratocan (KERA), lumican (LUM), aldehyde dehydrogenase 3 family member A1 (ALDH3A1), pyruvate dehydrogenase kinase, isoenzyme 4 (PDK 4), keratin sulfate, collagen V, collagen VI, and smooth muscle actin (ACTA2).

Nerve Cells

In contrast to many previously known corneal model systems, certain provided methods and compositions allow for functional innervation by a plurality of nerve cells of at least some of the epithelial and/or stromal cells present in a composition. This is important because it is well established that functional innervation is critical for corneal health. What was not well established prior to the present invention was how to accomplish such innervation in the context of an in vitro system. Accordingly provided methods and compositions include a plurality of nerve cells. In some embodiments, the nerve cells are human nerve cells. In some embodiments, the nerve cells are stem cells and/or afferent (e.g., sensory) nerve cells. In some embodiments, the nerve cells innervate at least a portion of the epithelial cells and/or at least a portion of the stromal cells.

In some embodiments, provided compositions exhibit a degree of innervation that approximates that seen in a typical human cornea. In some embodiments, provided compositions exhibit a degree of innervation of approximately 300 termini/mm$^2$ in the epithelium±10%. In some embodiments, provided compositions exhibit a degree of innervation between 100 termini/mm$^2$ and 500 termini/mm$^2$, inclusive. In some embodiments, provided compositions exhibit a degree of innervation between 200 termini/mm$^2$ and 400 termini/mm$^2$, inclusive. In some embodiments, provided compositions exhibit a degree of innervation of at least 100 termini/mm$^2$. In some embodiments, provided compositions exhibit a degree of innervation of at most 500 termini/mm$^2$. In some embodiments, innervation is exhibited homogeneously or substantially homogeneously across or within a provided composition. In some embodiments, innervation is exhibited in one or more discrete portions of a provided composition.

In some embodiments, nerve cells present in provided compositions exhibit one or more markers of lineage or function consistent with nerve cells in vivo. In some embodiments, the one or more markers may include one or more of tachykinin 2 (Tac2), calcitonin gene related peptide receptor component gene (CRCP), brain-derived neurotrophic factor (BDNF), transient receptor potential vanilloid 1 (TRPV), neurotrophic receptor tyrosine kinase 1 (NTRK1), transient receptor potential cation channel subfamily member 8 (TRPM8), tachykinin 1 (TAC1), and sodium voltage gate gene (SCN).

Growth Factors

One of the advantages of several embodiments of the present invention is the ability to use various growth factors to encourage cellular migration, differentiation and/or growth within and between portions of the composition. In some embodiments, at least one growth factor is added to at least one silk scaffold. In some embodiments, at least one growth factor is added to each silk scaffold. In some embodiments, the at least one growth factor is added prior to the addition of cells to the silk scaffold. In some embodiments, the at least one growth factor is substantially coated on coated on the at least one silk scaffold. In some embodiments, nerve growth factor is added to the first silk scaffold. In some embodiments, at least two growth factors (e.g., 3, 4, 5, 6, 7, 8, 9, 10 or more) are added to at least one silk scaffold. In some embodiments, at least one growth factor is added in a discrete pattern (see, for example FIG. 1).

Addition of at least one growth factor to provided compositions may occur in any application-appropriate manner. For example, in some embodiments, one or more growth factors may be deposited on the surface of a silk scaffold or composition (e.g., via printing or other direct deposition). In some embodiments, at least one growth factor may be added to an aqueous solution (e.g., growth or differentiation media) surrounding some or all of a provided silk scaffold or composition.

Any application appropriate growth factor may be used in accordance with various embodiments. In some embodiments, at least one growth factor will be included that is important for corneal development and/or function. In some embodiments, at least one of nerve growth factor (NGF), glial cell-derived neurotrophic factor (GDNF), brain derived neurotrophic factor (BDNF), keratinocyte growth factor (KGF), hepatic growth factor (HGF), neurotrophin-3 (NT-3), and epithelium growth factor (EGF) will be added to provided silk scaffolds or compositions.

Any appropriate amount of growth factors may be added to various embodiments, or portions thereof. In some embodiments, a growth factor may be added to or present in a particular silk scaffold or composition at a concentration between 1 and 1,000 ng/mL. In some embodiments, a growth factor may be added to or present in a particular silk scaffold or composition at a concentration between about 10 and 1,000 ng/mL (e.g., between about 50 and 1,000 ng/mL, 100 and 1,000 ng/mL, 10 and 900 ng/mL, 10 and 800 ng/mL, 10 and 700 ng/mL, 10 and 600 ng/mL, 10 and 500 ng/mL, 10 and 400 ng/mL, 10 and 300 ng/mL, 10 and 200 ng/mL, 10 and 100 ng/mL, 100 and 900 ng/mL, 100 and 800 ng/mL, 100 and 700 ng/mL, 100 and 600 ng/mL, 100 and 500 ng/mL, 100 and 400 ng/mL, 100 and 300 ng/mL, 100 and 200 ng/mL, inclusive).

Dynamic Culture Conditions

In addition to other advantages of the present invention, in some embodiments, provided methods and compositions include the use of dynamic culture conditions to better approximate in vivo conditions. Herein, dynamic culture conditions refers to conditions that approximate one or more of the dynamics of nutrient transfer, intraocular pressure, and tear flow all of which are known to contribute to healthy cornea development and function, but were not implemented in satisfactory ways prior to the present invention. As described above, the cornea is a transparent, avascularized tissue normally located at air-liquid interface. As such, oxygen and nutrients must diffuse into cornea via the aqueous humour and tear fluids as opposed to be carried to the tissue via one or more blood vessels. Additionally, corneal nerves secrete neurotrophic factors that contribute to cytokine dynamics that are important for healthy corneal development and function.

Intraocular Pressure (IOP)

In accordance with various embodiments, some provided methods and compositions include exposing provided compositions to elevated pressure (e.g., pressure above 0 mmHg). The use of elevated pressures, in various embodiments, is contemplated to approximate intraocular pressure (IOP) that is present in vivo. For example, in a healthy human being, IOP is maintained at around 10-20 mmHg. Variations of IOP may be caused by, among other things, one or more of heart rate, blood pressure, and respiration. In some embodiments, the composition is maintained under elevated pressure for a period of time. In some embodiments, the elevated pressure is between about 10-30 mmHg. In some embodiments, the elevated pressure is between about 15-20 mmHg. In some embodiments, the elevated pressure is greater than 0 mmHg. In some embodiments, the elevated pressure is less than 30 mmHg. In some embodiments, the elevated pressure is between 0-30 mmHg. In some embodiments, provided compositions are maintained under elevated pressure continuously. In some embodiments, provided compositions are exposed to elevated pressures cyclically or intermittently.

In some embodiments, provided compositions may be used to approximate a diseased or injured cornea. For example, in some embodiments, provided compositions may be maintained at IOP's of greater than 20 mmHg, which is typically considered a hypertensive pressure, as is observed in glaucoma patients.

Tear-Like Fluids

It is known that the surface of the cornea is immersed in a tear film, which serves as both a protective layer and a source of nutrients to the corneal epithelium. The tear film is composed of lipid, aqueous, and mucin layers. Typically, lipids in tear solution are thought to prevent evaporation of tears/drying of the cornea. Additionally, in vivo, an aqueous layer is secreted by the lacrimal gland, containing water and proteins. The mucins secreted by conjunctival goblet cells and epithelial cells provide lubrication as well as prevention of contamination. In general, in humans, the tear fluid is spread across the ocular surface by eye blinking with an average rate of once every 4.5 to 5.5 seconds.

Accordingly, and in accordance with various embodiments, the addition of a tear-like fluid can enhance the physiological relevance of certain provided methods and compositions. As such, in some embodiments, provided method and compositions include one or more tear-like fluids. In some embodiments, a tear-like fluid is or comprises at least one of a lipid (e.g., phosphatidylcholine and/or phosphatidylethanolamine), aqueous layer comprising water and at least one protein, an antibiotic, a neurotrophic peptide, and mucin. In some embodiments, a tear-like fluid is or comprises an aqueous solution including at least one lipid (e.g., phosphatidylcholine and/or phosphatidylethanolamine), at least one antibiotic, and at least one neurotrophic peptide. In some embodiments, a tear-like fluid is or comprises at least one lipid (e.g., phosphatidylcholine and/or phosphatidylethanolamine), at least one aqueous layer comprising water and at least one protein, and mucin. In some embodiments, the aqueous solution is or comprises saline. In some embodiments, a tear-like fluid comprises one or more of Von Ebner's gland protein, serum albumin, transferrin, serotransferrin precursor, lysozyme, IgA, IgG, IgM, lactoferrin, epidermal growth factor, aquaporin 5, an α-defensin, mammaglobin B, phospholipase A, extracellular glycoprotein lacritin precursor, oxygen-regulated protein 1, clusterin precursor, mesothelin precursor, lipophilin A precursor, antileukoproteinase 1 precursor, aspartyl aminopeptidase, 60S ribosomal protein L18a, phospholipid transfer protein precursor, chloride intracellular channel protein 2, and KFLA590.

According to various embodiments, a tear-like fluid may be applied to provided compositions in any of a variety of ways. In some embodiments, a tear-like fluid is applied dropwise. In some embodiments, a tear-like fluid is applied as a mist or spray. In some embodiments, a tear-like fluid may be applied perpendicularly to one or more silk scaffolds, for example, a first silk scaffold comprising epithelial cells (e.g., directly at a surface of a scaffold or composition). In some embodiments, a tear-like fluid may be applied across one or more silk scaffolds, for example, a first silk scaffold comprising epithelial cells (e.g., traversing the surface of the scaffold or composition generally parallel to the surface of the scaffold or composition).

Porosity

In accordance with various embodiments, some provided methods and compositions include one or more porous components. As used herein, the term "porous" refers to the property of at least one silk scaffold described herein to permit the passage of materials therethrough (in contrast to their passage along a silk scaffold). Silk scaffolds and compositions described herein may encompass a range of porosities, from those that do not substantially permit the passage of cells or proteins, to those that substantially permit the passage of proteins, but not cells, to those that permit the passage of both. Without wishing to be held to a particular theory, it is contemplated that the presence of particular levels of porosity may be advantageous in facilitating cellular ingrowth, nutrient diffusion, and/or waste removal. In some embodiments, one or more of the silk scaffolds is porous. In some embodiments, one or more silk scaffold has a porosity of at least 10% (e.g., at least 20%, 30%, 40%, 50%, 60%, 70% 80%, 90% or more). In some embodiments, at least one silk scaffold has a porosity of at least 30%. In some embodiments, at least one silk scaffold has a porosity of at least 50%. In some embodiments, at least one silk scaffold has a porosity of at least 70%. In some embodiments, at least one silk scaffold has a porosity of at least 90%. In some embodiments, provided scaffolds or compositions exhibit homogenous or substantially homogenous pore distribution. In some embodiments, provided scaffolds or compositions exhibit heterogeneous pore distribution, for example, as a gradient of porosity within a particular scaffold or composition.

In some embodiments, provided silk scaffolds and/or compositions may be made porous through the use of one or more porogens. It is contemplated that any known porogen may be suitable for use according to various embodiments. In some embodiments, a porogen may be or comprise crystals (e.g., sodium chloride crystals, sugar crystals), micro- and/or nano-spheres, polymers (such as polyethylene oxide, or PEO), ice crystals, sulfates, phosphates, alkali metals, alkali earth metal halides, polysaccharides, wax particles, synthetic polymer particles, and/or a laser. In some embodiments a porogen may comprise mechanical introduction of pores (e.g., using a needle or other article or device to pierce a silk scaffold or composition one or more times, or using stress to introduce one or more tears in the silk scaffold or composition).

According to various embodiments, any of a variety of pore sizes in particular silk scaffolds or compositions is contemplated. Various embodiments comprise a silk matrix with pores of any of a variety of sizes. In some embodiments, the pores of a silk scaffold or composition have a diameter between about 1 μm and 1,000 μm, inclusive. In some embodiments, the pores of a silk scaffold or composition may have a diameter of between about 5 μm and 1,000 μm (e.g., 5 to 900, 5 to 800, 5 to 700, 5 to 600, 5 to 500, 5 to 400, 5 to 300, 5 to 200, 5 to 100 μm). In some embodiments the pores of a silk scaffold or composition have a diameter of between about 400 and 700 μm, inclusive. In some embodiments the pores of a silk scaffold or composition have a diameter of between about 500 and 600 μm, inclusive. In some embodiments the pores of a silk scaffold or composition have a diameter of between about 5 and 50 μm, inclusive. In some embodiments, provided silk scaffolds and compositions comprise pores having a diameter of at least 1 μm. In some embodiments, provided silk scaffolds and compositions comprise pores having a diameter of at least 5 μm. In some embodiments, the pores of a silk scaffold or composition have diameters that are substantially similar in size across the scaffold of composition. In some embodiments, the pores of a silk scaffold or composition have diameters that vary significantly across the scaffold or composition.

Air-Liquid Interface (ALIC)

As is described herein, some provided methods and compositions include an air-liquid interface. While it is known that an air-liquid interface is important to encourage epithelial development and maintain corneal epithelial function, previously known corneal models have not been able to implement an air-liquid interface (also referred to herein as an ALIC) in a satisfactory manner. In some embodiments, at least some of the epithelial cells in (or on) a silk scaffold are exposed to an air-liquid interface. In some embodiments, all or substantially all of the epithelial cells in (or on) a silk scaffold are exposed to an air-liquid interface. Without wishing to be held to a particular theory, it is contemplated that exposure of provided compositions to simulated IOP and/or tear-like fluids in combination with an air-liquid interface provides significant advantages over previously known model systems.

Active Agents

In some embodiments, provided composition may include/incorporate any of a variety of active and/or labile agents. In some embodiments, such active agents may be useful in encouraging cellular growth and/or differentiation (e.g., as a supplement and/or replacement of one or more growth factors). In some embodiments, active agents may be added in order to modify a provided composition to serve as a model of corneal disease and/or injury.

In some embodiments, an active agent may be or comprise at least one of: a protein, a peptide (e.g., a peptide comprising at least one RGD (arginine-glycine-aspartic acid) motif), an antibiotic, a steroid, a vitamin, a chemotherapeutic agent, a nucleic acid (e.g., DNA or RNA), an antibody or fragment thereof, an aptamer, a sugar, a saccharide (e.g., a monosaccharide and/or a polysaccharide), a cytokine, a cell adhesion molecule (e.g., an integrin, a cadherin, an immunoglobulin, selectin), and/or a stressor or toxin (e.g., capsaicin).

In general, for incorporating one or more active agents in a provided silk scaffold or composition, the active agent can be included in a silk fibroin solution used for producing the silk scaffold or composition. Alternatively, or in addition, a preformed silk scaffold or composition can be added to a solution comprising one or more active agents and letting the active agent(s) absorb in/on the silk scaffold or composition.

In some embodiments, the active agent(s) can be distributed, homogenously or non-homogenously (e.g., in a gradient) in a silk scaffold or composition. In some embodiments, one or more active agents can be encapsulated or entrapped by silk fibroin in the silk scaffold(s) or composition. In some embodiments, one or more active agents can be mixed or blended with silk fibroin in the silk scaffold(s) or composition. In some embodiments, provided compositions comprise two or more active agents (3, 4, 5, 6, 7, 8, 9, 10 or more).

Physical and/or Mechanical Properties

In accordance with various embodiments, provided compositions may exhibit one or more physical and/or mechanical properties that approximate that of a native human cornea. For example, in some embodiments, provided compositions exhibit a stiffness of between 10-100 kPa, inclusive. In some embodiments, provided compositions exhibit a stiffness of between 30-70 kPa, inclusive. In some embodiments, provided compositions exhibit a stiffness of between 40-60 kPa, inclusive.

By way of additional example, in some embodiments, provided compositions exhibit an elastic moduli of between 50 and 80 kPa, inclusive. In some embodiments, provided compositions exhibit an elastic moduli of between 60 and 70 kPa, inclusive.

Methods of Making Provided Compositions

In accordance with various embodiments, the present invention also provides methods of making a tissue composition including the steps of providing a first silk scaffold comprising a plurality of epithelial cells, associating a second silk scaffold comprising a plurality of stromal cells with the first silk scaffold to form a silk scaffold stack, and introducing a plurality of nerve cells to the silk scaffold stack to form a tissue composition, wherein at least some of the plurality of neurons innervate at least one of: a portion of the epithelial cells, and a portion of the stromal cells. The aspects and components described above and in the examples below also apply to provided methods with equal force, with certain exemplary aspects additionally described below.

Associating

As provided herein, including in the illustrative examples below, provided silk scaffolds may be associated in any of a variety of ways. In some embodiments, provided silk scaffolds are associated by simply stacking them, either vertically or horizontally relative to a reference surface. In some embodiments, at least two silk scaffolds are linked, either directly (e.g., through covalent or non-covalent bonding), or functionally (e.g., through use of a supporting bioreactor apparatus, as exemplified in the examples below). In some embodiments, at least two silk scaffolds are linked chemically. In some embodiments at least two silk scaffolds are linked mechanically. In some embodiments at least two silk scaffolds are linked via a combination of chemical and physical means.

In some embodiments, one or more silk scaffolds may formed in the presence or in association with at least one other silk scaffold. By way of non-limiting example, in some embodiments, a silk scaffold will be at least partially immersed in a silk solution and then a second silk scaffold will be formed form the silk solution on or in close proximity to the previously formed silk scaffold. Alternatively or additionally, in some embodiments, a silk scaffold (e.g., a silk sponge, porous silk sponge, etc) may be 3D printed around a silk scaffold (e.g., a silk film, a stack of multiple silk films, etc).

Addition of Cells and/or Growth Factors

As described herein, and in accordance with various embodiments, provided compositions are made using a plurality of epithelial cells, stromal cells, and nerve cells. In some embodiments, one or more of these cell types may be seeded on a silk scaffold prior to assembling the final composition (e.g., cells are cultured on a silk scaffold for a period of time prior to assembly of the full composition). In some embodiments, one or more of these cell types may be seeded on a silk scaffold after assembly of the composition. In some embodiments, cells are added to a liquid phase surrounding and/or permeating a silk scaffold or composition and migrate into and/or onto the silk scaffold and/or composition. In some embodiments, one or more of these cells types will be present in a particular silk scaffold or surrounding substrate or fluid, and then develop such that at least some of the cells are present in two or more distinct portions of a provided composition. For example, in some embodiments, at least some of the nerve cells will initially be present in a silk scaffold (e.g., a silk sponge) and over time will extend processes into one or more other portions (e.g., silk scaffolds) of a composition. The illustrative examples below provide additional exemplary detail in this regard.

As described above and in the examples herein, addition of at least one growth factor to provided compositions may occur in any application-appropriate manner. For example, in some embodiments, one or more growth factors may be deposited on the surface of a silk scaffold or composition (e.g., via printing or other direct deposition). In some embodiments, growth factors depositing on a silk scaffold or composition may be bound to the silk scaffold or composition (e.g., by chemical, mechanical, or other means). In some embodiments, at least one growth factor may be added to an aqueous solution (e.g., growth or differentiation media) surrounding some or all of a provided silk scaffold or composition. In some embodiments, at least one growth factor is added prior to the introduction of cells to a particular silk scaffold or composition. In some embodiments, at least one growth factor is added substantially concurrently with the introduction of cells to a particular silk scaffold or composition.

In some embodiments, provided methods further include a step of maintaining the tissue composition at an elevated pressure. As described herein, in some embodiments, an elevated pressure is between about 10-30 mmHg. In some embodiments, the elevated pressure is between about 15-20 mmHg. In some embodiments, the elevated pressure is greater than 0 mmHg. In some embodiments, the elevated pressure is less than 30 mmHg. In some embodiments, the elevated pressure is between 0-30 mmHg. In some embodiments, provided compositions are maintained under elevated pressure continuously. In some embodiments, maintaining comprises exposing silk scaffolds or compositions to elevated pressures cyclically or intermittently.

In some embodiments, provided methods further comprise introducing a tear-like fluid to the issue composition (e.g., to at least one silk scaffold of a provided composition). As discussed elsewhere herein, and in accordance with various embodiments, a tear-like fluid may be applied to provided compositions in any of a variety of ways. In some embodiments, a tear-like fluid is applied dropwise. In some embodiments, a tear-like fluid is applied as a mist or spray. In some embodiments, a tear-like fluid may be applied perpendicularly to one or more silk scaffolds, for example, a first silk scaffold comprising epithelial cells (e.g., directly at a surface of a scaffold or composition). In some embodiments, a tear-like fluid may be applied across one or more silk scaffolds, for example, a first silk scaffold comprising epithelial cells (e.g., traversing the surface of the scaffold or composition generally parallel to the surface of the scaffold or composition). Exemplary tear-like fluids are described above.

In some embodiments, provided methods may be further comprise a step of introducing pores to at least one silk scaffold in a provided composition. As described elsewhere herein, in some embodiments, provided silk scaffolds and/or compositions may be made porous through the use of one or more porogens. It is contemplated that any known porogen may be suitable for use according to various embodiments. In some embodiments, a porogen may be or comprise crystals (e.g., sodium chloride crystals, sugar crystals), micro- and/or nano-spheres, polymers (such as polyethylene oxide, or PEO), ice crystals, sulfates, phosphates, alkali metals, alkali earth metal halides, polysaccharides, wax particles, synthetic polymer particles, and/or a laser. In some embodiments a porogen may comprise mechanical introduction of pores (e.g., using a needle or other article or device to pierce a silk scaffold or composition one or more times, or using stress to introduce one or more tears in the silk scaffold or composition).

Maintenance for Extended Periods of Time

In some embodiments, provided compositions can be maintained for longer periods of time as compared to previously known corneal models which are known to last for one 1-2 weeks. For example, in some embodiments, provided compositions may be maintained for at least two weeks (e.g., three, four, five, six, seven weeks or more). In some embodiments, provided compositions may be maintained for at least one month (e.g., two, three, four, five, six, seven, eight, nine, ten, eleven months or more). In some embodiments, provided compositions may be maintained for at least one year.

EXAMPLES

Example 1—Artificial Silk-Based Innervated Cornea

Unless otherwise stated, the materials and methods used in this example are as described below. For convenience, E, S, D and N will at times be used to represent hCECs, hCSSCs, DRG neurons and human neuron respectively.

Material and Methods

Preparation of Silk Solution

Silk solution was prepared from cocoons of *Bombyx mori* silkworm based on the previously known methods. Briefly, silk cocoons were purchased from Tajima Shoji Co. (Yokohama, Japan) and boiled for 30 min in 0.02 M $Na_2CO_3$ solution (Sigma-Aldrich. St Louis, Mo.). The boiled silk was rinsed with deionized water 6 times and dried overnight. The extracted silk was then dissolved in a 9.3 M LiBr solution and dialyzed against distilled water for 2 days to obtain a silk aqueous solution (5-7% w/v).

Preparation for Growth Factor Stamped Flat Silk Films

Flat, optically clear, porous silk films were prepared by casting 120 μL of 1% w/v silk solution with 0.05% w/v of polyethylene oxide (PEO) on a 12 mm diameter glass coverslip (Electron Microscopy Science. Hatfield, Pa.). The films were then dried overnight. High and low concentration NGF inks were used for stamping the silk films. The inks were composed of 100 μl (4 mg/mL) acetic acid-type I collagen solution (rat-tail tendon, BD, Franklin Lake, N.J.) containing 100 ng/ml keratinocyte growth factor (KGF) (Sigma), 100 ng/ml hepatic growth factor (HGF) (Sigma), 200 ng/ml epithelium growth factor (EGF) (Thermo Fisher. Waltham Mass.), and either a high concentration of NGF (400 ng/ml) or a low concentration NGF (200 ng/ml) (R&D Systems Minneapolis, Minn.). Multi-circular, radial and uniform stamp patterns were employed (FIG. 1). The multi-circular stamps were formed by dipping a 12 mm outside diameter and a 6 mm inside diameter donut shape polydimethylsiloxane (PDMS) (Fisher Scientific Co. Fair Lawn, N.J.) stamp in the low NGF ink and pressing onto the dried silk film. The center was stamped with a 6 mm PDMS cylinder carrying the high concentration NGF ink. The radial pattern was stamped with the high NGF ink with its shape indicated in Supplement FIG. 2. The whole surface of the uniformly stamped silk film was covered with high NGF ink. The silk films were annealed in water filled desiccators at −25 mmHg for 2.5 h for physical cross-linking. Before use, the silk films were soaked in DI water for 48 h to extract any residual PEO to form the pores.

Preparation of Patterned Silk Films

Patterned silk films were also prepared based on previously known procedures. Briefly, 1% w/v silk solution with 0.05% w/v of PEO was cast onto patterned PDMS molds with 600 lines/mm grating. The PDMS molds were prepared using our previously reported methods (Gil, E. S., S. H. Park, J. Marchant, F. Omenetto and D. L. Kaplan, *Response of human corneal fibroblasts on silk film surface patterns*. Macromolecular bioscience, 2010. 10(6): p. 664-673). The silk films were dried at room temperature overnight and water annealed with the same methods used with the stamped silk films. The patterned silk films were then peeled off from the mold using established methods. Id. The silk films were immersed in DI water for 2 days to extract the PEO to generate pores.

Preparation of Silk Sponges

Salt leach silk scaffolds with 500-600 μm pores were prepared using our previously reported procedure (Yao, D., S. Dong, Q. Lu, X. Hu, D. L. Kaplan, B. Zhang and H. Zhu, *Salt-leached silk scaffolds with tunable mechanical properties*. Biomacromolecules, 2012. 13(11): p. 3723-3729). The scaffolds were mounted in a custom designed well fabricated to be 1 mm depth depressed into a Delrin sheet (McMaster-Carr, Robbinsville, N.J.). The scaffold was sliced into 1 mm thick layers using microtome blade and cut into donut shapes (15 mm outer diameter, 12 mm inner diameter) with a biopsy punch (McMaster-Carr, Robbinsville, N.J.).

RGD and PDL Surface Modification

Glycine-Arginine-Glycine-Aspartic acid-Serine (GRGDS) peptide (Bachem, Torrance, Calif.) functionalized patterned silk films were prepared using methods from our previous work (Gil, E. S., B. B. Mandal, S.-H. Park, J. K. Marchant, F. G. Omenetto and D. L. Kaplan, *Helicoidal multi-lamellar features of RGD-functionalized silk biomaterials for corneal tissue engineering*. Biomaterials, 2010. 31(34): p. 8953-8963). Stamped flat silk films and salt leached silk scaffolds were soaked in 1 ml of 10 ug/ml poly-L-lysine solution overnight at 4° C.

Preparation of Collagen Hydrogels

Collagen gels were prepared by adding 100 ul of 10×DMEM (Sigma) to 900 μl (4 mg/mL) acetic acid-type I collagen solution (rat-tail tendon, Corning, Corning N.Y.) collagen solution, followed by neutralization with 20 μl 1M NaOH (Sigma).

Human Corneal Stromal Stem Cell (hCSSCs) Culture

HCSSCs isolated from collagenase digestion of limbal stromal tissue of human corneas unsuitable for transplant were obtained from the Center for Organ Recovery and Education (Pittsburgh, Pa.). HCSSCs were passaged 4 times before seeding. Cells were detached with 0.25% trypsin (GIBCO) solution and seeded on the surface of the sterilized patterned porous silk film at a concentration of 15,000 cells/cm$^2$. Cell seeding was accomplished by adding the cell suspension dropwise on top of the films. The films were incubated for 30 min to allow time for cell attachment. Seeded silk films were cultured in proliferation medium containing DMEM/MCDB-201 in the ratio of 3 to 2 (v/v) with 2% fetal bovine serum, 10 ng/mL platelet-derived growth factor, 1 mg/mL lipid-rich bovine serum albumin (Albumax, Life Technologies, Grand Island, N.Y.), 10 ng/mL epidermal growth factor, 5 mg/mL transferrin, 5 ng/mL selenous acid (ITS), 0.1 mM ascorbic acid-2-phosphate, 1028 M dexamethasone, 100 IU/mL penicillin, 100 mg/mL streptomycin, 50 mg/mL gentamicin, and 100 ng/mL cholera toxin until confluent (2 days). After cells reach confluency, hCSSCs were differentiated on the silk films into keratocytes (hCSCs) with differentiation medium composed of advanced DMEM (Life Technologies), containing 1.0 mM L-ascorbic acid-2-phosphate (Sigma-Aldrich, St Louis, Mo.), 50 μg/mL gentamicin (Life Technologies), 2 mM L-alanyl-L-glutamine (Life Technologies), 100 μg/mL penicillin, 100 μg/mL streptomycin (Mediatech, Manassas, Va.) 0.1 ng/mL transforming growth factor-beta3 (TGF-B3, Sigma-Aldrich), and 10 ng/mL basic fibroblast growth factor (FGF-2 Sigma).

Human Corneal Epithelial Cell (hCECs) Culture

Primary hCECs (C0185C, Thermo Fisher) and passaged 5 times before seeding. Cells were detached with 0.25% trypsin (GIBCO) and seeded on top of sterilized stamped silk films at a density of 150,000/cm$^2$. The films were then incubated for 4 hours to allow time for cell attachment and then cultured in keratinocyte SFM medium for 2 days to reach confluency.

Chicken Dorsal Root Ganglion (DRG) Cell Culture

DRG explants were dissected from day 8 chicken embryos following protocols developed in our prior study (Leclere, P. G., E. Norman, F. Groutsi, R. Coffin, U. Mayer, J. Pizzeyand D. Tonge, *Impaired axonal regeneration by isolectin B4-binding dorsal root ganglion neurons in vitro*. The Journal of neuroscience, 2007. 27(5): p. 1190-1199). The explants were then carefully placed on the surface of the salt leached silk scaffolds with forceps and incubated for 2 hours to allow time for cell attachment. The scaffolds were then flipped over and cultured in DMEM containing 20% FBS and 50 ng/ml NGF.

Co-Culture of hCSCs hCECs and DRG Neurons

Figure 2:
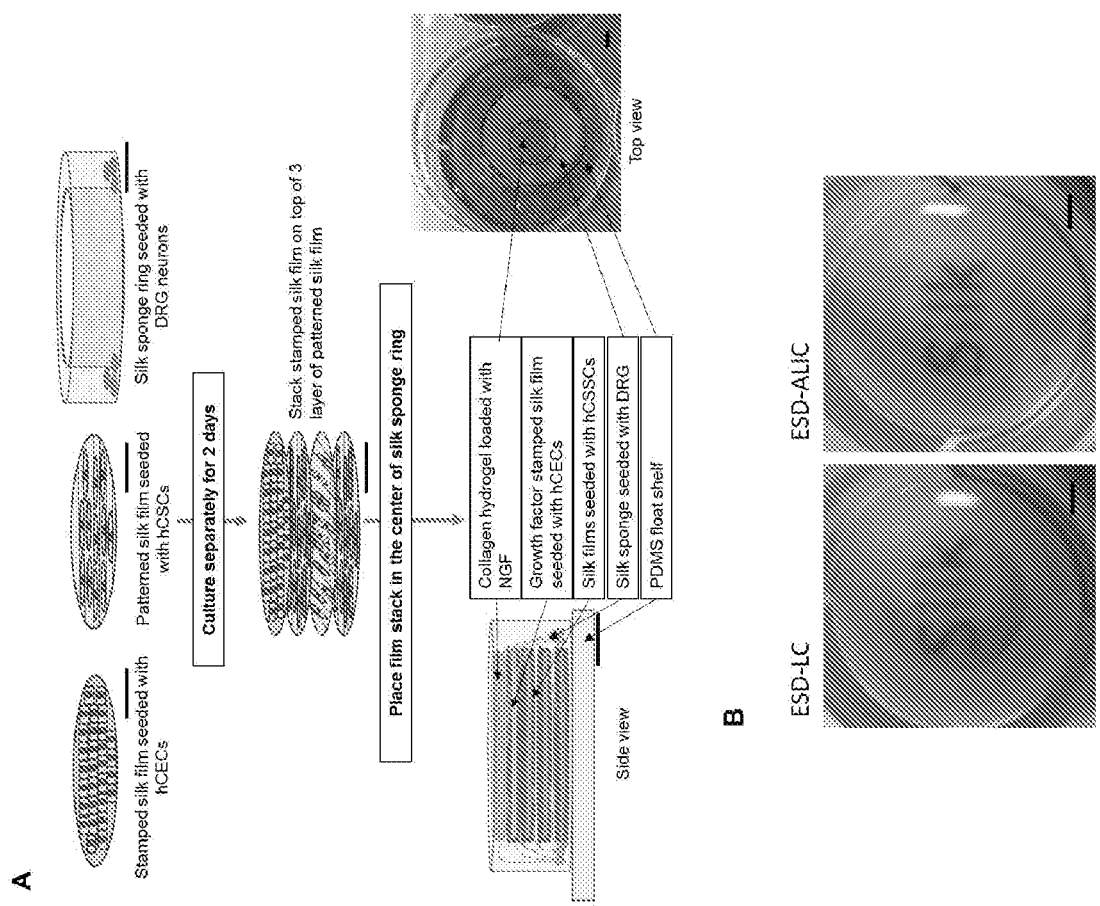
FIG. 2. A) The methodology of co-culture: hCECs, hCSCs, and DRGs were seeded on growth factor stamped silk films, RGD functionalized patterned silk films, and donut shape silk salt leach scaffolds, respectively, and cultured separately for 2 days. The stamped film was then stacked on top of 3 patterned silk films with their patterns crisscrossed with each other. B) The silk film stacks were then cut into 12 mm diameter circles and placed in the middle of donut shape silk salt leach scaffolds. The cells were co-cultured for 2 days in the liquid phase before moved to an air-liquid interface culture. The co-culture at the ALI remained for 28 days. Scale bars=3 mm.

The scaffolds for co-culture were designed to mimic corneal anatomy (FIG. 2). For convenience, E, S and D will be used to represent hCECs, hCSCs and DRG neurons, respectively. To prepare the co-culture scaffolds, 3 layers of patterned silk films seeded with S were stacked with their patterns in a criss-cross pattern. Then, the silk stacks were cut to 12 mm diameter with a biopsy punch (McMaster-Carr) and transferred to the center of the silk sponges. The flat silk films seeded with E were then transferred with forceps and gently placed on top of the film stacks. To achieve integrity of the scaffold, 500 μl type I rat tail collagen was cast on top and absorbed into the scaffold. In order to guide axons toward the top of the scaffolds, 50 μl of collagen hydrogel containing 400 ng/ml of NGF was cast on top of the film stack. The scaffolds were then incubated at 37° C. for 30 min to complete the crosslinking. After this, the whole scaffold was immersed in hCSSCs differentiation medium and cultivated for 2 days. A customized designed waffle shape PDMS floating shelf (5 mm thick, 5 cm diameter, with 16×1 mm$^2$ holes) was prepared by casting PDMS on top of Delrin® molds (McMaster-Carr). This PDMS shelf allowed the top of the scaffold to remain at the air-liquid interface (ALIC) while the bottom was immersed in hCSSCs differentiation medium. The cultivation in liquid (LC) and air-liquid interface (ALIC) lasted 1 month. The co-cultures of E and D (ED-LC and ED-ALIC), S and D (SD-LC and SD-ALIC), and single cultures (E-LC, E-ALIC, S-LC, S-ALIC, D-LC, D-ALIC), were also processed as comparisons for the three cell types in tri-culture (ESD-LC, ESD-ALIC). The scaffolds for two types of cells co-cultures and single cultures were prepared with the same methods with the ESD tri-cultures but only contained the respective cellular components.

Immunohistochemistry

The single cultures and co-cultured samples were fixed at day 14 and 20. Samples were fixed in 4% paraformaldehyde in PBS (Affymetrix, Cleveland, Ohio) for 45 min and then treated with 5% BSA FOR 30 min. Cellular morphology was revealed with anti β tubulin III staining. Keratocan was stained to reveal hCSCs ECM secretion while involucrin was stained to reflect the maturity of hCECs. The dilution of antibodies is indicated in Table 1. The samples were treated with primary antibodies for 12 h at 4° C. and then washed with PBS 3 times, 15 min each. The samples were stained with secondary antibodies for 8 h at 4° C. and washed with PBS 3 times, 15 min each. DAPI was diluted 1:1000 in 5% BSA solution at the same time as the primary antibodies. Images were taken on a BZX-700 microscope (Keyence Corporation, Itasca, Ill.) at 10× and 4×.

TABLE 1

The primary antibody and secondary antibody used in immunostaining and their dilutions.

| | Samples | Primary antibody dilution | Secondary antibody dilution |
|---|---|---|---|
| B tubulin III | ED, SD, ESD, E, S, D | Anti-β-tubulin III rabbit antibody( ) 1:500 diluted in 5% BSA | Anti-rabbit IgG-FITC antibody produced in goat (Sigma). 1:200 diluted in 5% BSA. Use Donkey Anti-Rabbit IgG (FITC) (Abcam) when co-stain with keratocan 1:200 diluted in 5% BSA |
| Keratocan | SD, ESD, S | Anti-keratocan Goat antibody 1:100 diluted in 5% BSA | Donkey anti-Goat IgG, Alexa Fluor® 568 (Sigma), 1:200 diluted in 5% BSA |
| Involucrin | ED, ESD, E | Anti-involucrin mouse antibody( ) 1:500 diluted in 5% BSA | Goat Anti-Mouse IgG H&L (TRITC) (Abcam), 1:200 diluted in 5% BSA |

Quantitative Reverse Transcript PCR (qPCR)

Gene expression levels for keratocan, lumican, α-actin, aldehyde dehydrogenases, involucrin, gap junction, as well as keratin was quantified by RT-PCR (qPCR) as described in previous studies. In brief, total RNA extracted from the scaffolds was reverse transcribed to cDNA in a 20 ul reaction using high-capacity cDNA reverse transcription kit (Thermo Fisher). Quantitative RT-PCR of cDNA (~30 ng/µl) was performed using assays containing fluorescent hybridization probes (Taq Man: Thermo Fisher). Reactions were incubated at 95° C. for 10 min and amplification was carried out on samples with 2 min incubation at 50° C., followed by 50 cycles of 15 seconds at 95° C. and 1 min at 60° C. The reaction for RT-PCR was processed in a 15 µl solution containing 1× Universal PCR Master Mix (Thermo Fisher) with 6 µl cDNA samples. RNA expression at day 28 was calculated using ΔΔ Ct method, compared to day 0 samples.

Neuronal Extension Measurement

Positive staining of β tubulin III was determined at 4× magnification. The images were collected from n=3 samples from 3 independent experiments. All the stitched images were then converted into 8-bit tiff files using Image J (NIH). The neuron J routine (see Meijering, E., M. Jacob, J. C. Sarria, P. Steiner, H. Hirlingand M. Unser, *Design and validation of a tool for neurite tracing and analysis in fluorescence microscopy images*. Cytometry Part A, 2004. 58(2): p. 167-176) was then applied to measure axon length. The density of axon on 4× images was counted using Image J cell counter.

Statistical Analysis

Data analysis was performed with one-way ANOVA with Dunnett post hoc test. The significance level was set at $p<0.05$. All experiments were run in at least triplicates for two independent experiments.

Results

Guidance of Neuronal Innervation

After 14 days of cultivation, the uniformly stamped silk films provided higher axonal innervation area (FIG. 1) than multi-circular and radial stamped films. Thus, this strategy was selected to guide neuronal innervation towards the center of the scaffolds in the remaining studies. After 28 days of cultivation the axons were mostly located on the top surface of the scaffolds (FIG. 3 panels A, B) indicating successful guidance of innervation. This guidance was also studied at the ALIC (FIG. 3C) where the top surface of scaffold had twice the density of axons than in the LC. The length and density of axons reached an average of 3 mm and 55 termini/mm$^2$ in the LC versus 4 mm and 99 termini/mm$^2$ in the ALIC. Thus, the combination of stamped silk films and NGF loaded collagen supported the effective guidance of neuronal innervation towards the top center of the scaffolds.

Co-Culture and Single Cultures in the Liquid Phase

Figure 4:
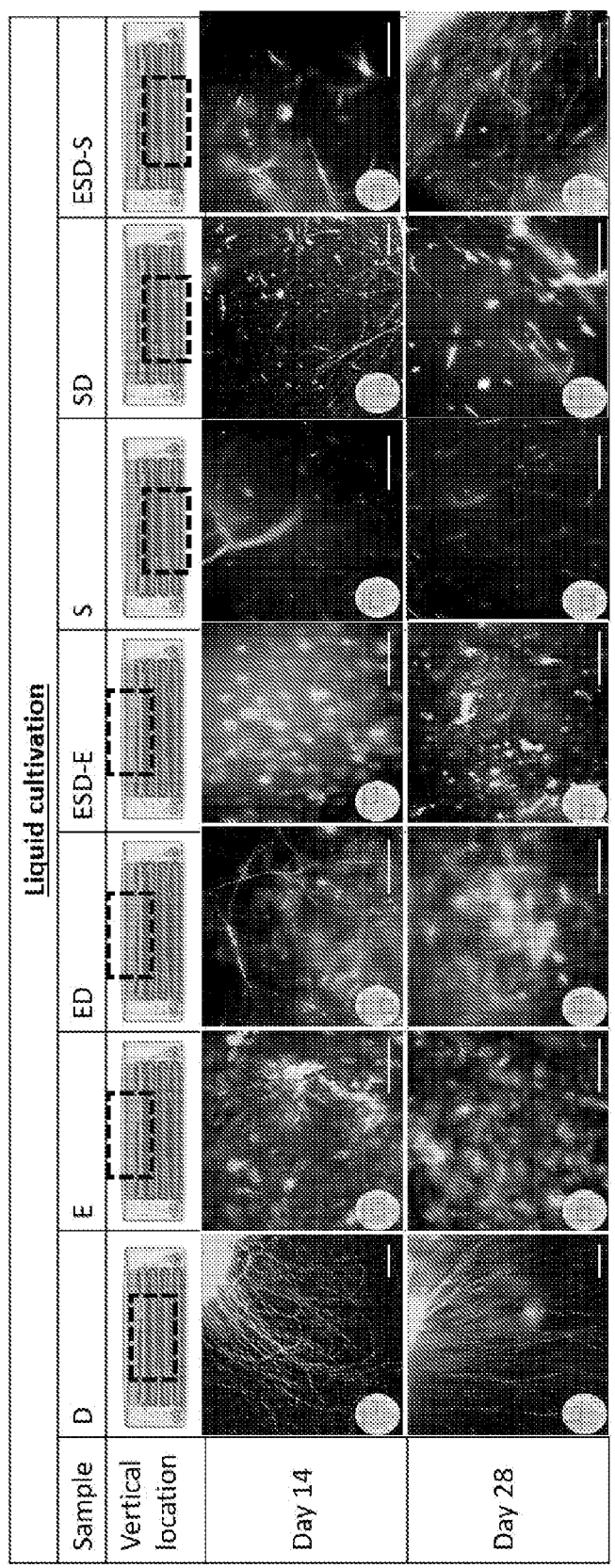
FIG. 4. Immunocytochemistry staining of DRGs, hCECs, and hCSCs cultured alone (D, E, S); hCECs DRG co-culture (ED); hCSCs, DRG coculture (SD); hCECs, hCSCs, DRG tri-culture (ESD-E and ESD-S) in liquid phase. β III tubulin was stained green in all the sample. Involucrin was stained red in E, ED, ESD-E groups. Keratocan was stained red in S, SD, ESD-S groups. The dashed boxes indicate the location of images. Scale bars=100 μm FIG. 5. Quantification of length (panel A) and density (panel B) of axons in day 28 DRG single cultures in liquid phase(D-LC) and at air-liquid interface (D-ALI); DRG and hCSCs co-culture in liquid phase(SD-LC) and at air-liquid interface (SD-ALIC); DRG co-culture with hCECs in liquid phase (ED-LC) and at air-liquid interfaces (ED-ALIC); DRG neuron, hCSCs and hCECstri-culture in liquid phase (ESD-LC) and at air-liquid interfaces (ESD-ALIC). The air-liquid interface culture supported significantly longer axons compared to the liquid cultures. D-ALIC and ESD-ALIC groups provided the densest axons among the groups reaching an average of ~100 termini/$cm^2$. Data was collected from n>3 from three independent experiments. *$P<0.0001$; $P<0.001$.
Figure 5:
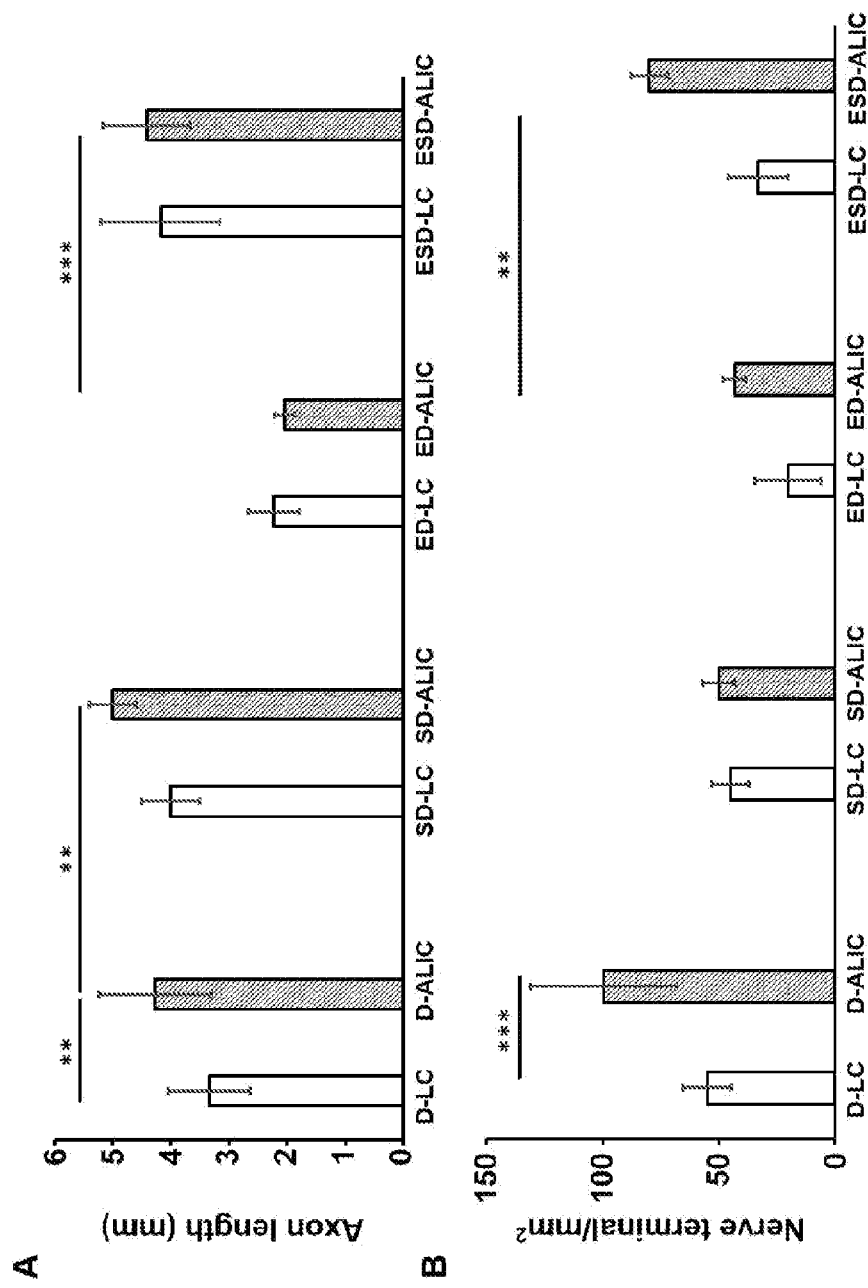

DRG, hCSCs and hCECs survived in the co-cultures and single culture systems over the 28 days of cultivation, while remaining intact and transparent (FIG. 2B). Immunostaining (FIG. 4) showed the expression of involucrin from innervated epithelium increased over time (ED-LC and ESD-LC groups) appeared to be at a higher level than in non-innervated groups (E-LC). When hCECs were innervated in the ESD-LC and ED-LC groups, the morphology of the hCECs adopted a healthy polygonal epithelial cell morphology whereas in the E-LC group the cells were elongated. HCECs aggregation was observed in the liquid phase single cultures and co-cultures. The hCSCs retained alignment and expressed keratocan in all groups through the cultivation time. Innervation was developed in all the co-culture groups, with the SD-LC group resulting in axons that were ~2 times longer than in the ED-LC group (FIG. 5). The innervation was located on the top surface of scaffolds and between each layer of silk films. Direct contact between axons and hCECs was also observed (FIG. 4 ESD-E, ED). There was no significant difference in length and density of axons between the SD-LC and ESD-LC (FIG. 5).

Co-Culture and Single Cultures at the Air-Liquid Interface

Figure 3:
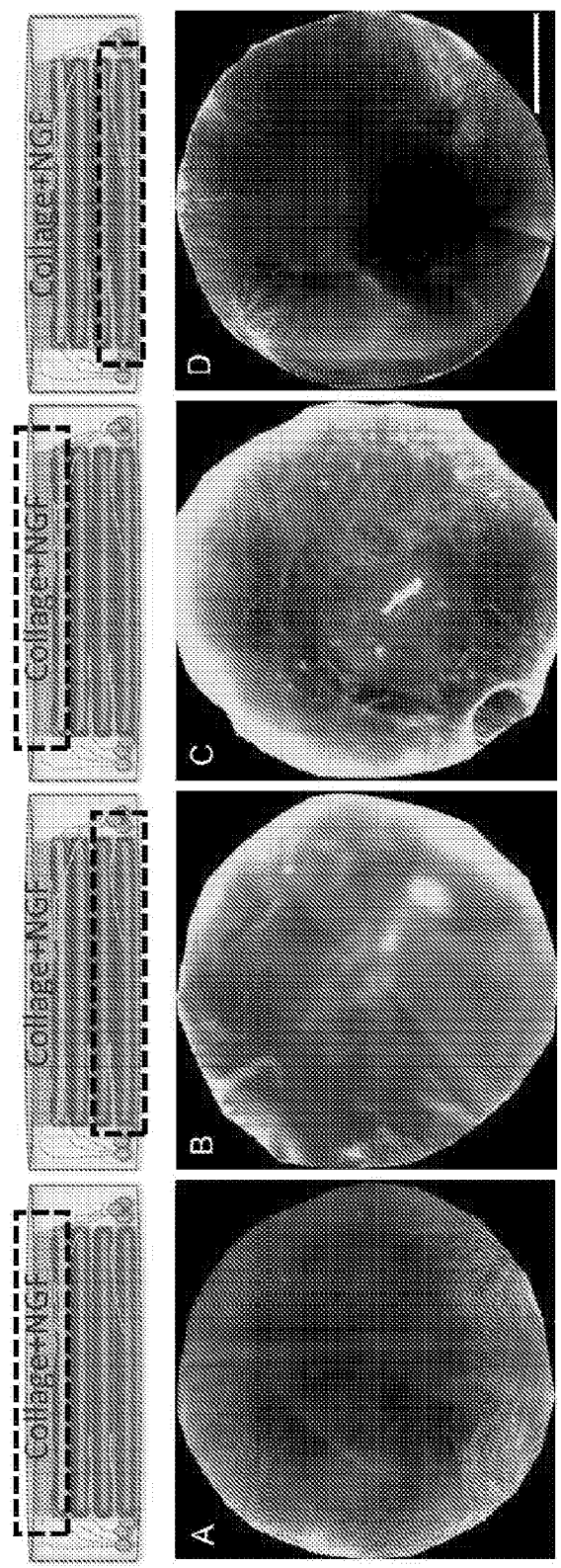
FIG. 3. Immunocytochemistry staining of β III tubulin (green) showed axons being guided towards the top center of the scaffolds in the LCs and ALICs. A) The top surface of day 28 D-LC sample. B) The bottom surface of day 28 D-LC sample. C) The top surface of day 28 D-ALIC sample. D) The bottom surface of day 28 D-ALIC sample. Scale bars=6 mm.
Figure 6:
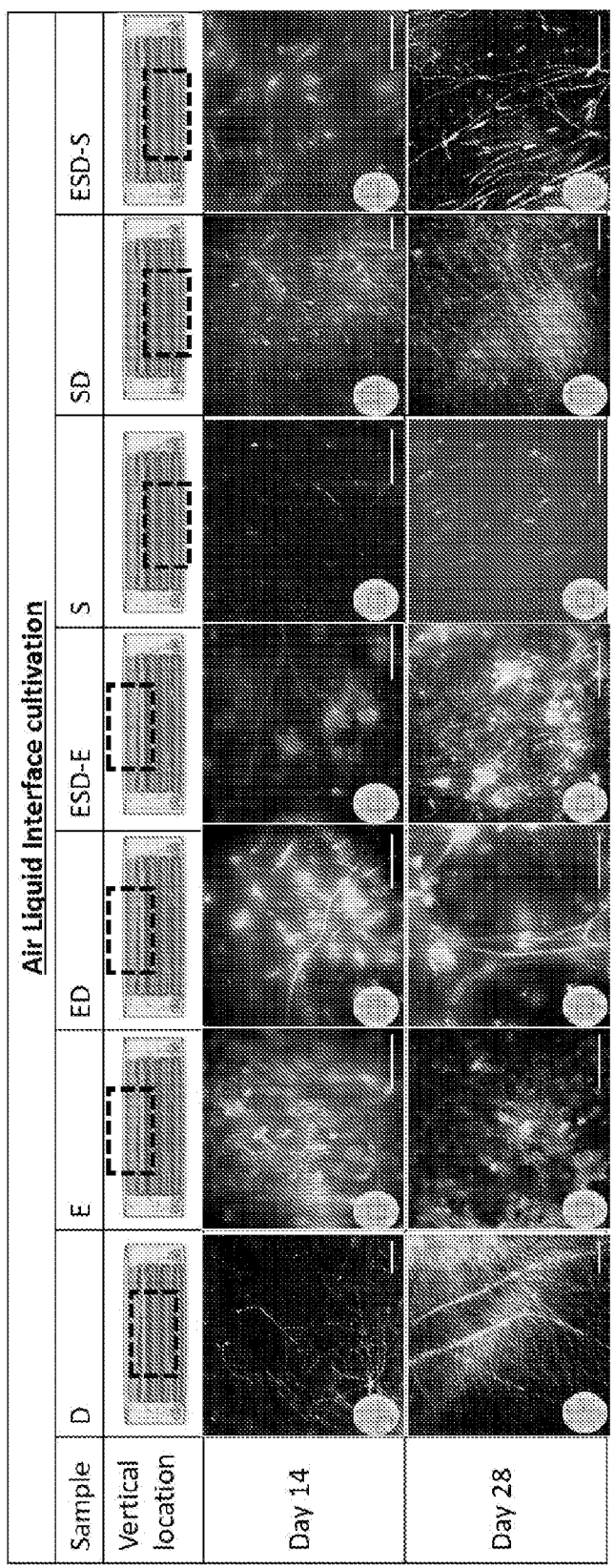
FIG. 6. Immunohistochemistry staining of DRGs, hCECs, and hCSCs cultured alone (D, E, S); hCECs, DRG co-culture (ED); hCSCs, DRG coculture (SD); hCECs, hCSCs, DRG tri-culture (ESD-E and ESD-S) at air-liquid interface. β III tubulin was stained green in all the sample. Involucrin was stained red in E, ED, ESD-E groups. Keratocan was stained red in S, SD, ESD-S groups. The dashed boxes indicate the location of images. Scale bars=100 μm FIG. 7. Immunohistochemistry staining of day 28 E-ALIC and ESD-ALIC samples. βIII tubulin stained green, nuclei stained blue. More cellular layers (white arrows) were observed in ESD-ALIC than in E-ALIC sample. Images were collected from n>3 from three independent experiments.
Figure 7:
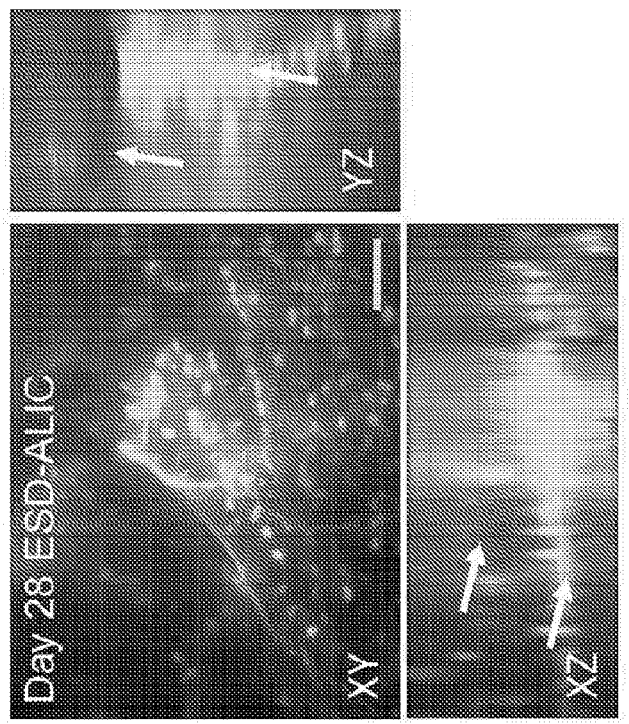
Figure 7:
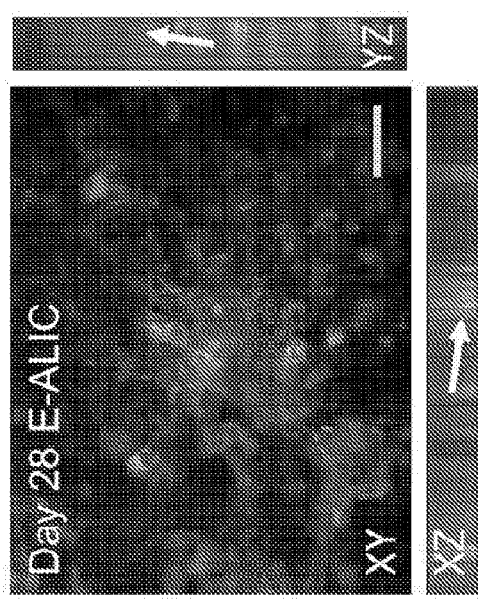

DRG, hCSCs and hCECs all survived co-culturing at the ALIC. The integrity of the scaffold and the transparency of the stacked films was maintained through 28 days of cultivation (FIG. 2B). Immunostaining (FIG. 6) showed that the hCECs formed polygonal epithelial cell morphology and developed into multicellular layers in the ESD-ALIC group (FIG. 7). The secretion of involucrin in the ESD-ALIC group appeared to be highest among the different conditions. The alignment of hCSCs remained through the cultures in the S-ALIC, SD-ALIC and ESD-ALIC systems. The secretion of keratocan was also observed in the hCSCs single culture and co-cultures. The DRGs cultured alone at the ALIC had an axon density that was approximately two-fold higher than in the LC (FIGS. 3, 6). Innervation was observed at the top surface and between the silk film layers in the scaffolds with axons directly contacting corneal cells (FIG. 6 SD, ED, ESD-S, ESD-E). The densest innervation appeared in the ESD-ALIC group (80 terminal/mm$^2$), which is 3 and 2 times higher than the ESD-LC and D-LC group respectively.

Q-PCR Analysis

Figure 8:
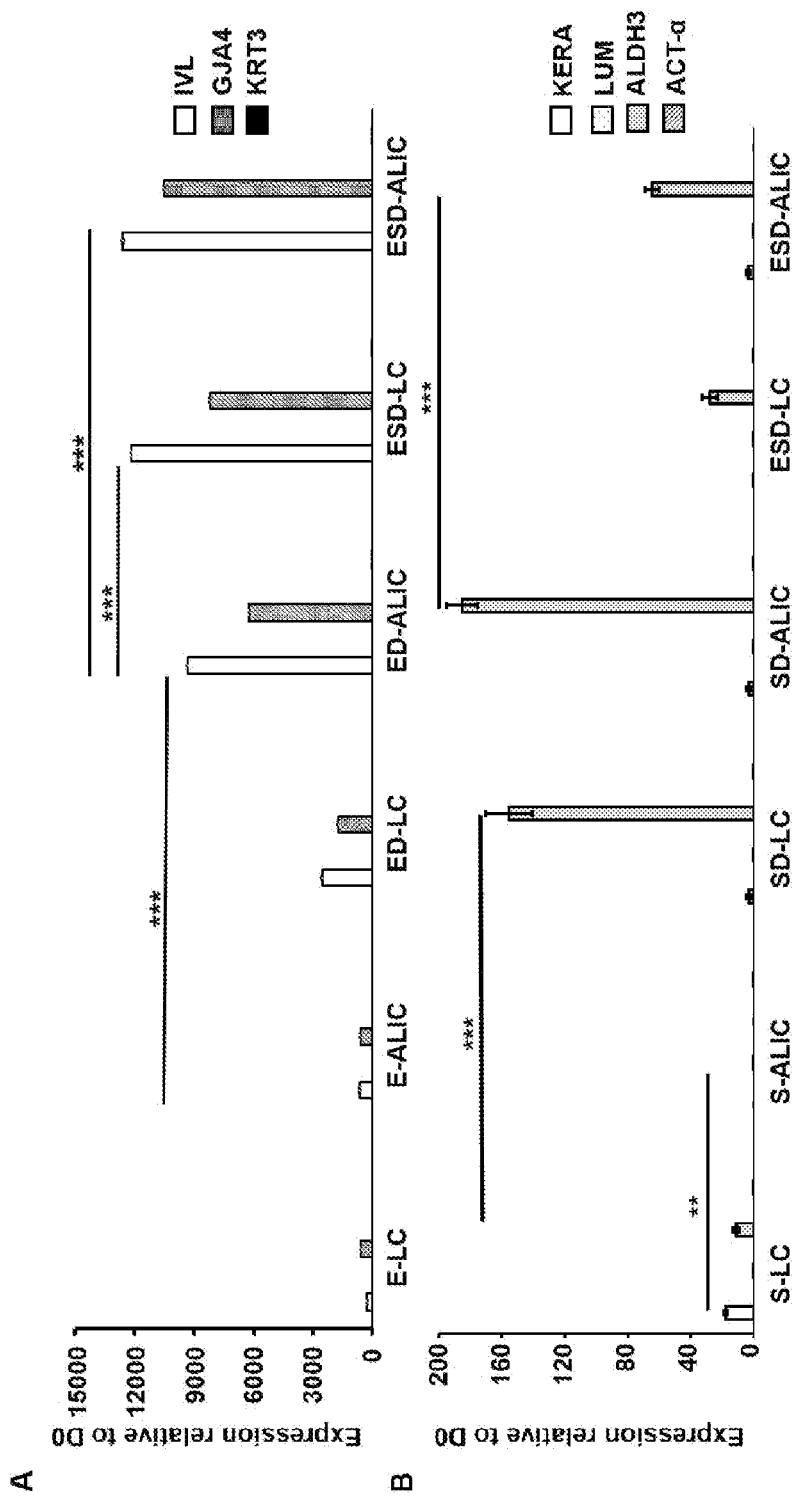
FIG. 8. Gene expression of hCSCs (A) and hCECs (B). The expression of involucrin (IVL), gap junction (GJA) and keratin (KRT3) was quantified through Q-PCR and normalized with day 0 samples of hCECs using ΔΔ Ct methods. The expression of keratocan (KERA), lumican (LUM), aldehyde dehydrogenase 3(ALDH3) and α-actin (ACT-α) was quantified through Q-PCR and normalized with day 0 samples of hCSCs using ΔΔ Ct methods. The expression level of IVL, GJA were significantly higher in ED and ESD co-cultures compared to hCECs single cultures. hCSCs expressed the most keratocan when cultured in the liquid phase. SD-ALIC groups had significantly higher keratocan expression compared to the S-ALIC groups. The data was collected from n>3 from three independent experiments. *P<0.0001; P<0.001.

In order to investigate the impact of innervation on the hCECs, expression of involucrin (IVL), gap junction (GJA), and keratin (KRT3) was quantified by qPCR. IVL is a marker for maturity whereas GJA is a barrier function marker for hCECs. IVL and GJA were expressed in all groups, whereas KRT3 was only expressed when the epithelium was innervated (FIG. 8). ED-ALIC had significantly higher expression of IVL and GJA compared to ED-LC. Also, the ESD-LC and ESD-ALIC groups had significantly higher IVL and GJA expression compared to ED-LC and ED-ALIC. The expression of keratocan (KERA) lumican (LUM) aldehyde dehydrogenase (ALDH) and actin α (ACT-α) was quantified to analyze the functional state of the hCSCs. KERA and LUM are corneal stroma specified ECM proteins and were previously shown to be expressed by hCSCs differentiated from hCSSCs (see Wu et al., 2013). ALDH is a critical enzyme for maintenance of corneal transparency. ACT-α is a smooth muscle cell marker previously expressed when hCSSCs were not differentiated towards hCSCs. The expression of ACT-α was not detected in all the culture groups (FIG. 8). The S-LC group had the highest KERA and LUM expression compared to all the other groups, whereas the expression of all three markers in S-ALIC was not significant. When hCSCs were innervated (SD-ALIC and ESD-ALIC groups), the expression of KERA and LUM were not different from the SD-LC and were significantly higher than the S-ALIC. The expression of ALDH was significantly greater in ALIC and groups with innervation compare to in LC and non-innervated samples.

Discussion

Compared to collagen-based corneal tissue models with innervation, provided systems and compositions including silk protein provided tunable materials to match the mechanical properties of human cornea. Further, provided films and sponges prepared from silk supported aligned hCSCs growth and improved neuronal extensions. In collagen-based tissue models, NGF was loaded into hydrogels to create a concentration gradient to guide neuronal growth. However, the density and length of innervation were not quantified, and collagen undergoes consistent contraction over time that impacts cell functions. In contrast, provided corneal tissue models, including NGF loaded collagen gels, were combined with NGF stamped silk films to guide the axons towards the top center of the scaffolds. Dorsal root ganglion neurons were used to mimic corneal innervation, due to its roles as a critical component as sensory neurons. As shown herein, in the Examples provided, the average terminal density and axon length reached 100 termini/mm$^2$ and 4 mm in the ALICs. The guided, dense, and long axons establish an essential foundation to for innervated corneal tissue models. Further, these systems remained functional for at least one month in culture, supporting sustained cultivation to allow both acute and chronic studies with these new corneal tissues.

Previously, an air-liquid interface was achieved by culturing tissue constructs in trans-wells. However, HCSC survival in trans-wells was not robust in some preliminary experiments. Thus, PDMS shelves were designed to maintain a fluid environment for the stroma while the epithelium was positioned at the ALIC. As a result, the hCSCs survived well in these systems. This new design and implementation allowed, at least in part, the superior results described herein.

As described herein, after the exemplified scaffold designs for neuronal innervation guidance and air-liquid cultivation were completed, hCSCs and hCECs were included in the cultures. In contrast to previously known methods, and in order to include the epithelium, an important barrier layer for the cornea, HGF, KGF and EGF were stamped on the top silk film layer and hCECs survived through 28 days of cultivation in the LC and ALIC. Multilayer growth of hCECs was achieved in the ALIC systems, reflecting the importance of the air-liquid environment to generate suitable outcomes for these cornea tissues.

The expression of IVL, GJA and the number of epithelium cellular layers in the innervated and air-liquid interface cultured samples were significantly higher than in the non-innervated samples cultivated in liquid phase, suggesting innervation and the air liquid interface contributes towards achieving cell and tissue maturity and barrier functions of the corneal epithelium.

During the sustained cultivation in LC, the survival of hCSCs appeared to decrease when hCECs were included in the system. This outcome was likely due to the hCECs remaining proliferative throughout the cultivation which created competition for nutrients. This issue did not appear in the ALICs, which again supported the key role of this environment maintaining a healthy epithelium and stroma. However, when hCSCs were cultured alone, the LC provided better KERA expression compared to the ALIC, indicating the liquid environment enhanced the secretion of ECM in the stroma.

The high expression of ALDH and KERA in the innervated stroma showed the essential role of innervation on corneal stromal transparency and function. In humans, it was observed that the impairment of corneal innervation can cause corneal ulcers (neurotrophic keratitis). Patients with neurotrophic keratitis present decreased corneal sensitivity with alterations in corneal epithelium, nerve, keratocyte, and endothelium. The findings described herein corroborate the hypothesis that corneal sensory nerves play a critical role in maintaining the vitality, metabolism, and replenishment of corneal cells. The data shown for the exemplified embodiments herein suggest that this new corneal 3D tissue model has potential to help to explore and address these types of corneal diseases.

Example 2—Addition of Simulated Intraocular Pressure and/or Tear Flow

In this example, a silk protein biomaterial-based in vitro tissue model that includes human corneal epithelium (hCECs), stromal (hCSCs) and neurons (hNCs) cultured in a bioreactor to assess corneal ECM formation, mimics of physiological tear washing and the application of simulated intraocular ocular pressure (IOP) was designed and tested to study impact on cellular phenotypes in static and dynamic (IOP±tear washing) environments.

The in vitro corneal tissue model in this example was formed by co-culturing hCECs, hCSCs and hNCs in silk scaffolds to mimic corneal architecture. A bioreactor composed of an artificial anterior chamber creating ocular pressure (10-20 mmHg), and an artificial tear outlet on the lid with 15-30 drops/min flow rate was used to house the 3D corneal tissue systems and sustain the culture for 2 months. Several measures were used assess the exemplary system of this example including live and dead assay, immunohistochemistry, RT-PCR, and mechanical properties were investigated to assess cellular phenotype, ECM formation, tight junction (TJ) formation, and neuronal function. Data were compared between innervated and non-innervated, static and dynamic cultivated tissue systems using statistical analysis.

Significantly higher TJ formation and keratocytic ECM protein expression were observed in the innervated models compared to the non-innervated controls. During dynamic cultivation, the scaffold gained curvature and increased stiffness when compared to static cultivation conditions. Tear washing increased the cell layers and tight junction formation in the epithelium, while the stimulation of pressure significantly increased the synthesis of ECM protein in the stroma. A summary of the results may be found in FIG. 9-13.

Figure 9:
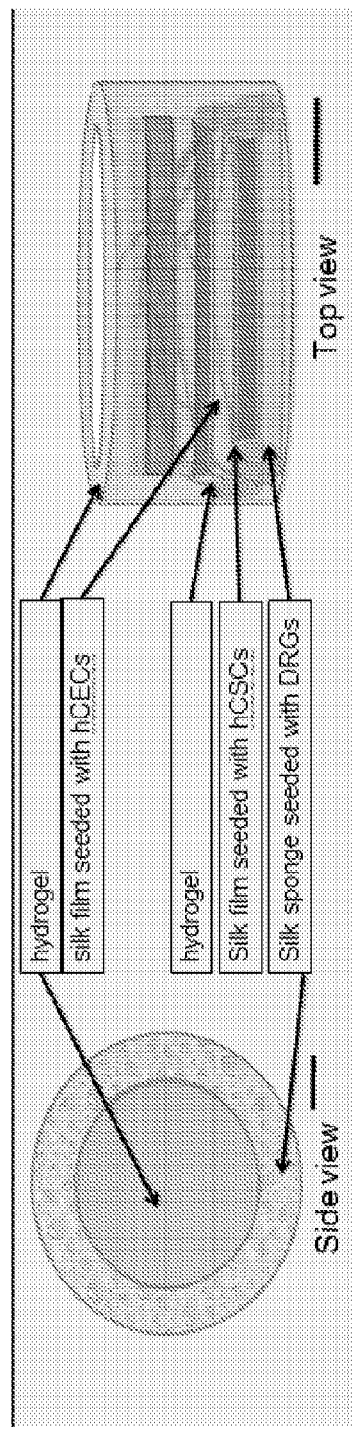
FIG. 9—shows a schematic of an exemplary silk film stack seeded with hCECs and hCSCs that was placed in the center of a silk sponge ring containing DRG neurons. Scale bars are 3 mm.
Figure 10:
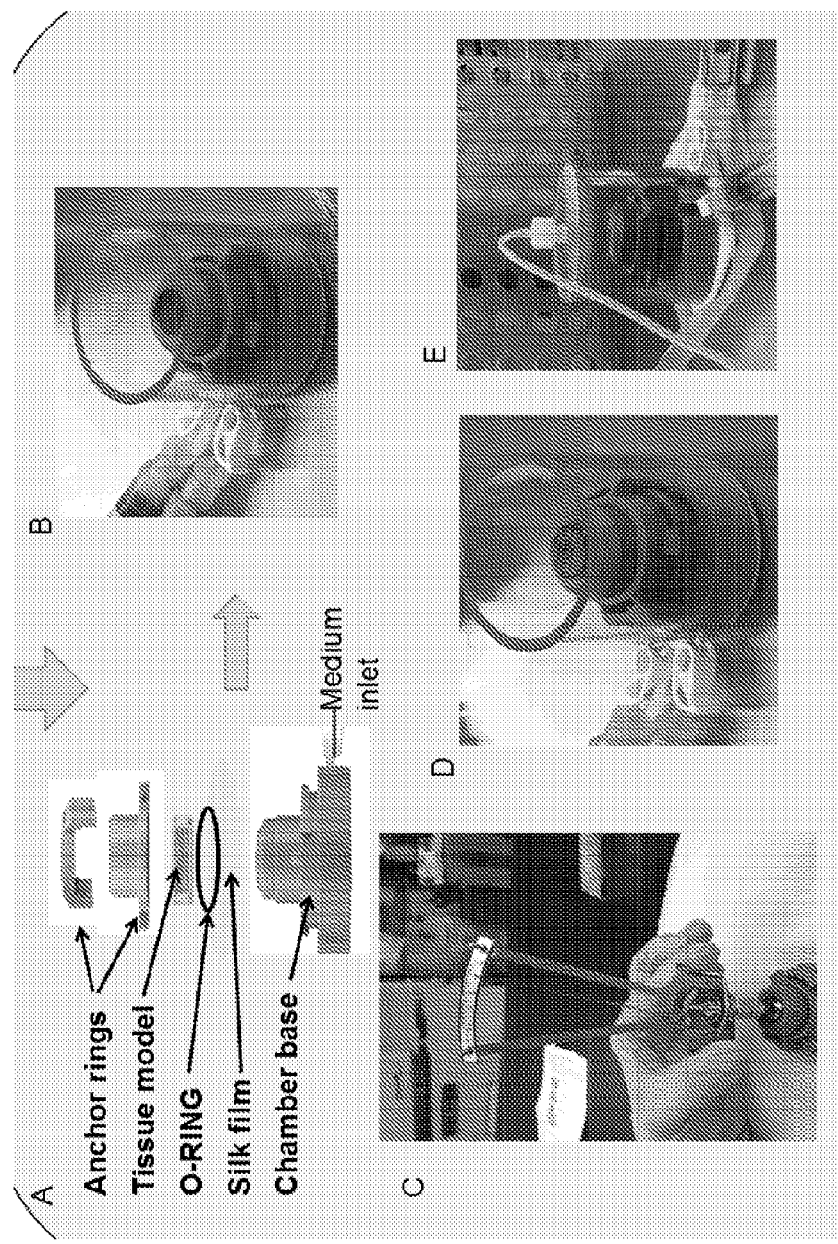
FIG. 10—shows a schematic diagram and several photographs of an exemplary apparatus for supporting dynamic cultivation of provided compositions. Panel A shows a schematic diagram of the apparatus. Panel B shows a photograph of an exemplary provided composition under pressure to simulate intra-ocular pressure. Panel C shows a photograph of the apparatus in panel B under a pressure of 15 mmHg as shown with a tonometer. Panel D shows a photograph of silk sponges soaked with media being used to moisturize the surface of the exemplary provided composition. Panel E shows a photograph of an exemplary apparatus including a tear wash setup, which provides tear-like fluid to provided compositions.

FIG. 9 shows a schematic of the composition used in this example. Briefly, two silk films were seeded with hCECs and hCSCs, respectively, and placed in a stacked configuration, which was in turn surrounded by a silk sponge ring seeded with dorsal root ganglion cells. FIG. 10 shows a schematic and several photographs of the apparatus used to support the composition as well as to apply simulated intraocular pressure (IOP) and simulated tear film.

Figure 11:
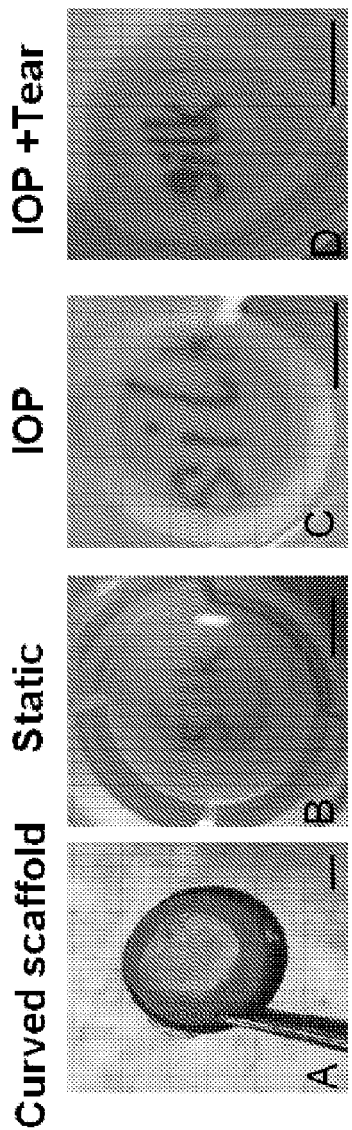
FIG. 11—shows photographs of exemplary provided conditions. Panel A shows a photograph of a provided composition which gained curvature after dynamic cultivation for 28 days. Panel B shows a silk film stack that remained transparent after 28 days of static culture. Panel C shows a photograph of a silk film stack after 28 days of dynamic culture under intraocular pressure (IOP). Panel D shows a photograph of a silk film stack after 28 days of dynamic culture under intraocular pressure and with tear wash.

After 28 days in culture under dynamic conditions, provided compositions took on a significant degree of curvature (see FIG. 11, panel A). Also after 28 days, provided compositions remained optically transparent under conditions of static culture (see FIG. 11, panel B), under dynamic culture conditions with simulated IOP (see FIG. 11, panel C), and under dynamic culture conditions with simulated IOP and simulated tear film (see FIG. 11, panel D).

Figure 12:
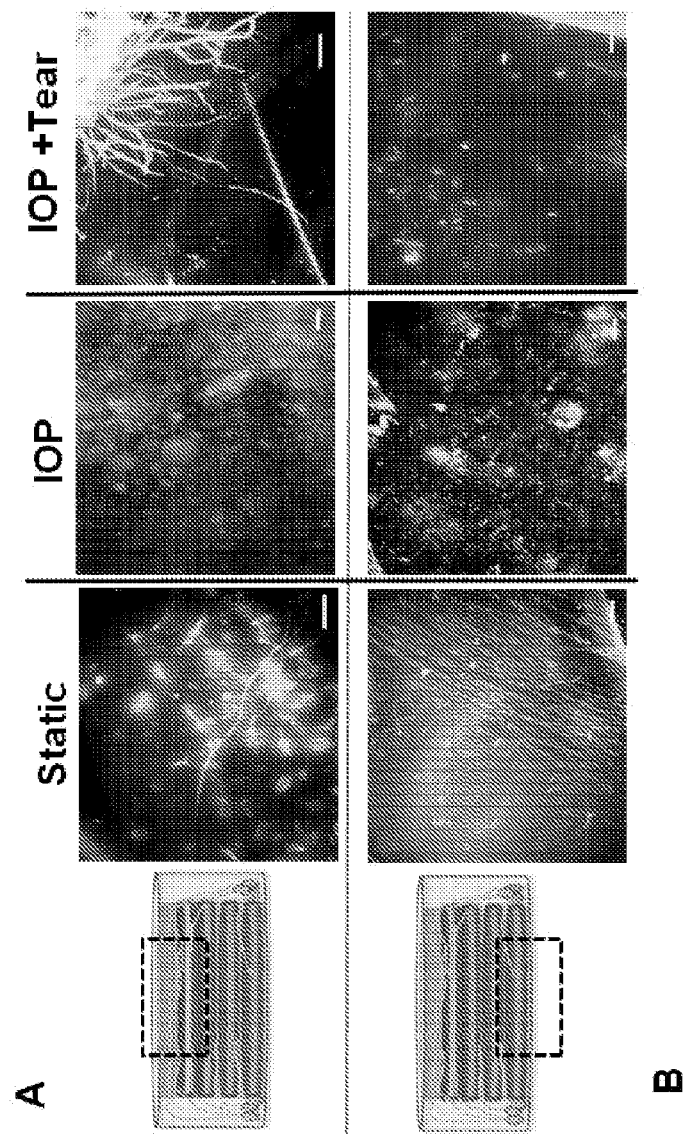
FIG. 12—Panel A shows III tubulin (green) and DAPI (blue) staining for 28 days under static or dynamic culture, with or without simulated intraocular pressure and/or tear wash. Panel B shows the length and density of axons under the conditions listed in panel A. Axon length in dynamic cultivation was shorter with similar nerve density compared to static cultivation (nerve density and axon length under static conditions=100±20/mm$^2$ and 4±2.1 mm, respectively; and 120±35/mm$^2$ and 0.29±0.08 mm, respectively, when exposed to simulated IOP and tear wash).

In order to assess the status of cells on provided compositions, an assessment of both neuronal marker expression (here βIII tubulin) and live/dead status (DAPI staining) were used. FIG. 12 shows, in panel A, βIII tubulin (green) and DAPI (blue) staining of provided compositions after 28 days of static culture or dynamic culture (with simulated IOP and/or simulated tear film). In panel B, FIG. 12 shows the length and density of axons in provided compositions after 28 days of static culture or dynamic culture (with simulated IOP and/or simulated tear film). As described herein, axon length in dynamic cultivation was shorter with similar nerve density compared to static cultivation (nerve density and axon length under static conditions=100±20/mm$^2$ and 4±2.1 mm, respectively; and 120±35/mm$^2$ and 0.29±0.08 mm, respectively, when exposed to simulated IOP and tear wash).

Figure 13:
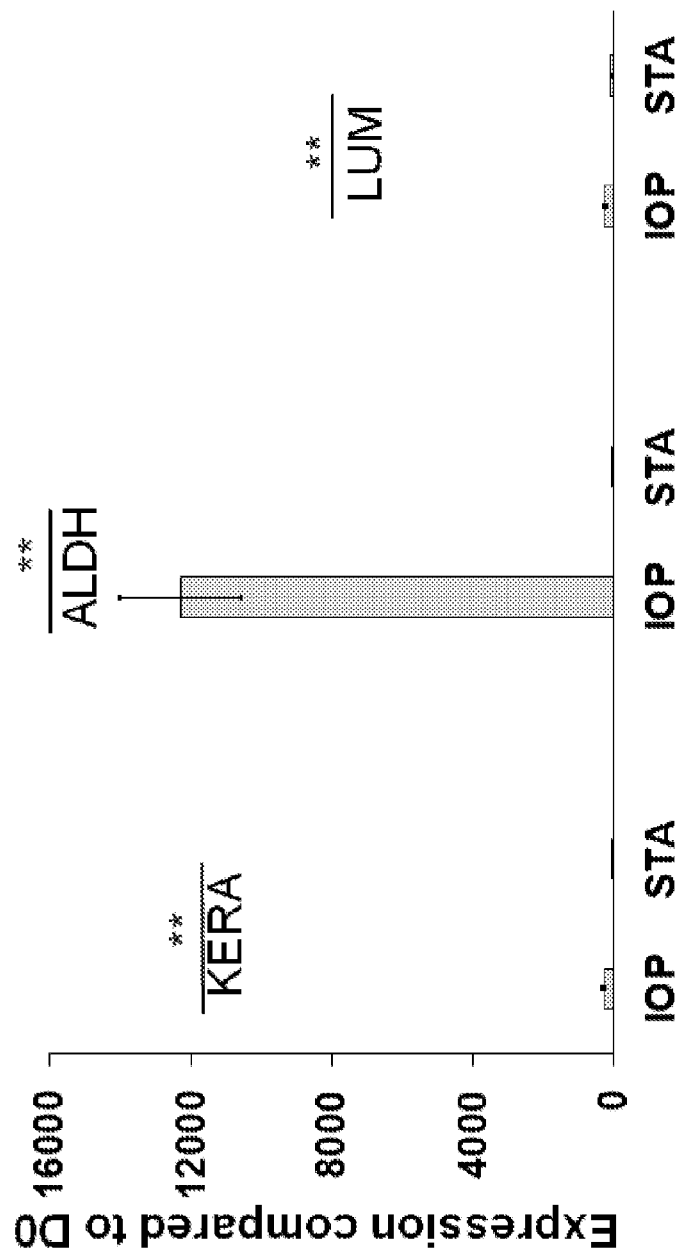
FIG. 13—shows an exemplary graph of keratocan, ALDH, and Lumican expression levels under conditions of dynamic cultivation as compared to static cultivation (STA). **p<0.001

The expression level of keratocan, aldehyde dehydrogenase (ALDH), and Lumican are known to be markers for healthy functional corneal development. As shown in FIG. 13, the expression level of keratocan, ALDH, and Lumican under dynamic culture conditions is significantly higher than static cultivation. **$p<0.001$.

In this example, the provided innervated corneal epithelium and stroma tissue model cultivated in a dynamic environment provides a useful system for studying long term interactions between neuronal innervation and corneal tissue, and the impact of IOP and tear washing on corneal tissue.

Example 3—Effects of Simulated Intraocular Pressure and/or Tear Flow on Silk-Based Cornea Innervated with Human Sensory Neurons In this example, unless otherwise specified the materials and methods used were as follows.
Materials & Methods:
Human Sensory Neuron Cell Culture Human sensory neurons (hNs) were differentiated from human neuronal stem cells reprogrammed from human fibroblasts. Subsequently, neuronal stem cells were differentiated for 10 days on a gelatin-coated plate into sensory neurons, using 3 inhibitors and 3 growth factors supplemented in neurobasal medium (Thermofisher) containing 2% B-27 (Sigma), 10% antibiotic-antimycotic (Thermofisher), 10% glutamax (Thermofisher), 3 growth factors (25 ng/ml NGF, 25 ng/ml BDNF, 25 ng/ml GDNF), and 3 inhibitors (3 μM CHIR99021, 10 μM SU5402, and 10 μM DAPT) (Thermofisher). Silk sponges were immersed in 0.1 mg/ml (poly-D-lysine) PDL solution at 4° C. overnight before use. The PDL solution was aspirated prior to cell seeding. Then 5 ml TrypL-select solution (Thermo Fisher Scientific) was added per dish of neurons and incubated at 37° C. for 1 min. The solution was subsequently neutralized with neurobasal medium to inactive the enzyme and detach neurons from the dishes. The cell solution was then collected and centrifuged at 1200 RPM for 5 min and suspended with the neurobasal medium at a concentration of 100,000,000 cells/ml. A 100 μl of cell solution was then added to 300 μl of neutralized collagen hydrogel and applied onto the silk sponge using 133 μl per scaffold. The sponges were then incubated for 1 hour to allow time for crosslinking before beginning culture in 3I+3G neurobasal medium.

Tri-Cultivation of hCSSCs, hCECs, and hNs

To prepare the co-culture scaffolds, 3 layers of patterned silk films seeded with hCSSCs were stacked with their patterns in a crisscross pattern. Then, the silk film stacks were cut to 12 mm diameter with a biopsy punch (McMaster-Carr) and transferred to the center of the silk sponge donuts. The flat silk films seeded with hCECs were then transferred with forceps and gently placed on top of the film stacks. To achieve integrity of the scaffold, 500 μl type I rat tail collagen was casted on top and absorbed into the scaffold. In order to guide axons toward the top of the scaffolds, 50 μl of collagen hydrogel containing 400 ng/ml of NGF was cast on top of the film stack. The scaffolds were then incubated at 37° C. for 30 min to complete the crosslinking. After this, the whole scaffold was immersed in hCSSCs differentiation medium and cultivated for 2 days. A customized designed waffle-shaped PDMS floating shelf (5 mm thick, 5 cm diameter, with 16×1 mm$^2$ holes) was prepared by casting PDMS on top of Delrin® molds (Mc-Master-Carr). This PDMS shelf allowed the top of the scaffold to remain at the air-liquid interface (ALIC) while the bottom was immersed in hCSSCs differentiation medium. The cultivation in liquid (LC) and air-liquid interface (ALIC) lasted 28 days. The co-cultures of hCECs and human sensory neurons, and hCSSCs and human sensory neurons, and single, were also processed as comparisons for the three cell types in tri-cultures.

Preparation of Artificial Anterior Chamber

Figure 14:
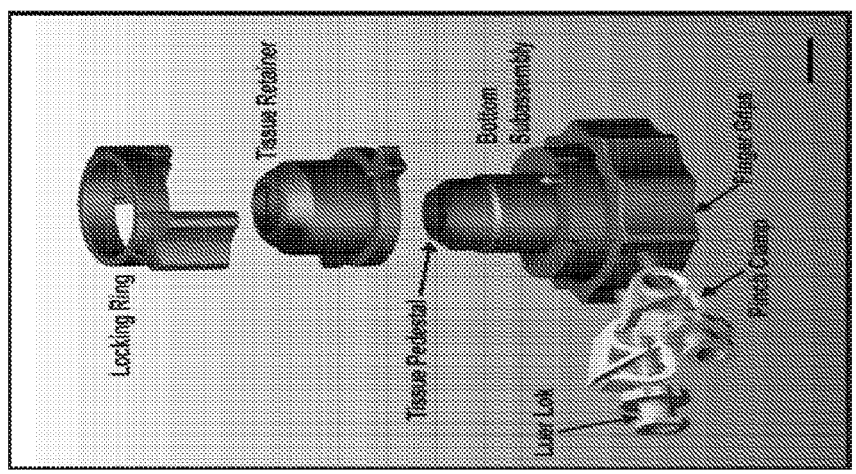
FIG. 14. The structure of exemplary artificial anterior chamber. The base of chamber is connected to luer lock which can be closed by tightening the pinch clamp. The tissue retainer and locking ring are used to seal the system. Scale bar=6 mm FIG. 15. Representative picture and schematic for exemplary bioreactor. A) The tissue model was pressurized and formed a dome shape under artificial IOP. A tear wash device was added with dropwise tear, to bathe the surface of tissue model. B) Schematic of the inner structure of bioreactor. C) The cellular component in the tissue model in bioreactor with dash line indicating the intraocular pressure. Scale bars=6 mm FIG. 16. Q-PCR result of day 14 differentiated neuronal stem cell reprogrammed from human fibroblasts. Compared to control groups cultivated without inhibitors and growth factors, the 3I+3G differentiated group had higher expression of pain mediators (CRCP, BDNF, TAC1), temperature and capsaicin sensor (TRPV1), and neurotrophic factor receptor (NTRK1). The data were collected from n>3 from three independent experiments. *P<0.0001; P<0.001.
Figure 15:
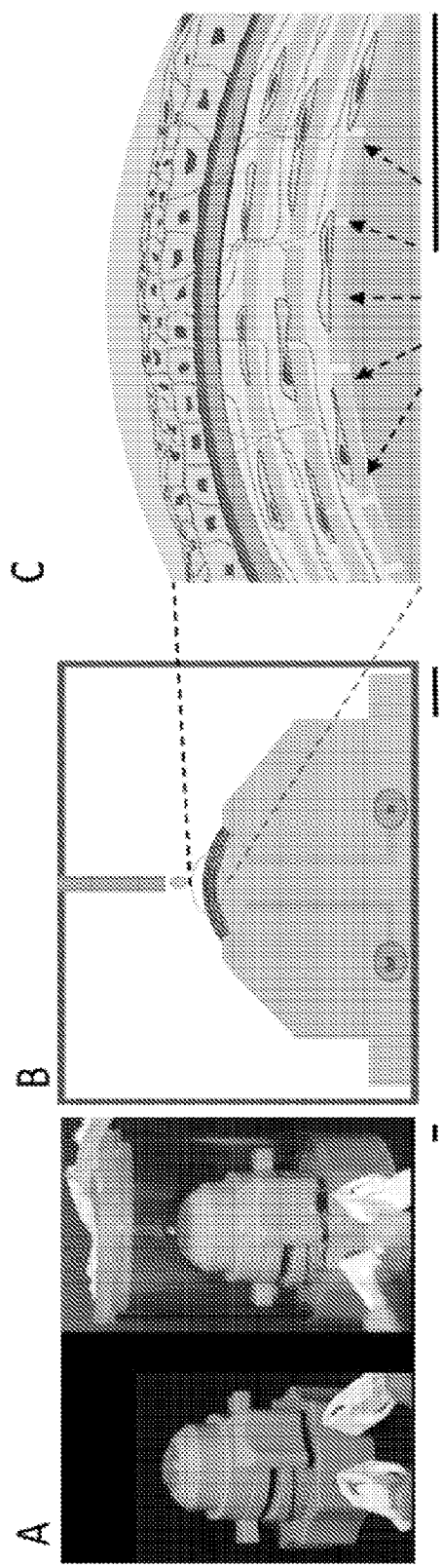

The artificial anterior chambers were purchased from Barron®. As can be seen in FIGS. 14 and 15, the chamber is composed of a base, a tissue retainer, and a locking ring. A porous silk film was made and applied on top of the base to serve as a bottom membrane. Following application, a 15 mm inner diameter and 17 mm outer diameter rubber o-ring (McMaster) was placed on top of the film to improve sealing and decrease stress on the scaffold. The corneal tissue model, described in Example 1 above, was cultured for 14 days was then placed gently on top of the silk film and was anchored down by the tissue retainer. Sealing of the anterior chamber was achieved by fastening the locking ring. The co-culture medium was then pushed into the system through a luer lock connector. The pinch clamps were clipped once the pressure reached the range of 15-20 mmHg. This pressure was maintained and measured by a tonometer (Medical Device Depot, Ellicott City, Md.) every 3 days throughout the duration of culture. Culture medium was changed every 2 days by complete aspiration and refilling the chamber.

Preparation of Tear Dropping Device

A custom designed lid was made of polycarbonate with a 3 mm medium inlet (FIG. 15, panels A and B) and was fitted with a silicone pipe to provide tear flow (TF) on the surface of the scaffold (FIG. 15, panel A). The pipe was anchored to have 1 mm of distance from the top surface of the scaffold. The bioreactor was then placed on top of an absorbing gauze pad to collect tear flow run off from the top surface of the scaffold. The tear pipe was connected to a 50 ml syringe containing TF fluid (hCSSCs differentiation medium supplemented with 25 ng/ml EGF) (Sigma). To provide tear flow, 50 ml syringes were then loaded in a syringe pump (Harvard Apparatus, Holliston, Mass.) programmed for a 50 ul/min flow rate.

Immunohistochemistry

Figure 16:
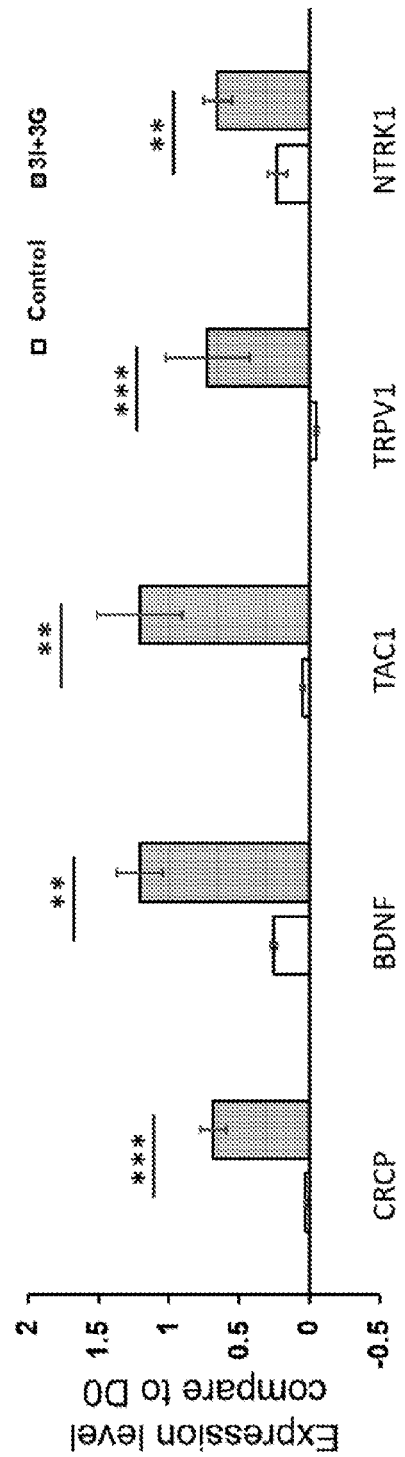

Dynamic and static cultivated tissue models were fixed on day 28 and day 40 by soaking samples in 10% formalin PBS solution overnight. The samples were then rinsed with PBS to remove residual formalin before dehydration with ethanol, xylene and paraffin (Table 2). The samples were cut into 3 pieces, embedded and hardened in fresh paraffin (VWR). The samples were then sectioned into 8 μm thick slices and rehydrated following the steps in Table 3 Antigen retrieval was completed using unmasking solution (Vector Laboratory, Burlingame, Calif.) and heated for 20 min with a vegetable steamer. The primary antibodies were then added onto the slides, incubated at 4° C. overnight and washed with PBS 3 times before application of the secondary antibody. Following 1 hour incubation at room temperature, the unbound secondary antibody was rinsed off the slides by washing with PBS 3 times prior imaging. The dilution ratio used for primary and secondary antibody preparation is included in Table 2.

medium, the expression of pain mediators (CRCP, BDNF, TAC1), temperature and capsaicin nociceptor (TRPV1), and neurotrophic factor receptor (NTRK1) were upregulated compared to the group cultured with neurobasal medium alone (FIG. 16). These data provide baseline information on relevance of these cells for the study of sensory/pain-related outcomes.

Neurons Responded to Dynamic Cultivation

Figure 17:
FIG. 17. HCSSCs, hCECs and neuron marker expression after IOP+TW dynamic cultivation. Q-PCR result for expression of CRCP, BDNF, SCN from neuron; KERA, LUM, ALDH from hCSSCs and IVL, GJA from hCECs in day 28 static and IOP+Tear wash samples. The dynamic cultivation appeared to improve the expression of CRCP, SCN, KERA, LUM, and ALDH. No significant difference was observed between static and dynamic cultivation in IVL and GJA4 expression level. The data were collected from n>3 from three independent experiments. *P<0.0001; P<0.001.
Figure 18:
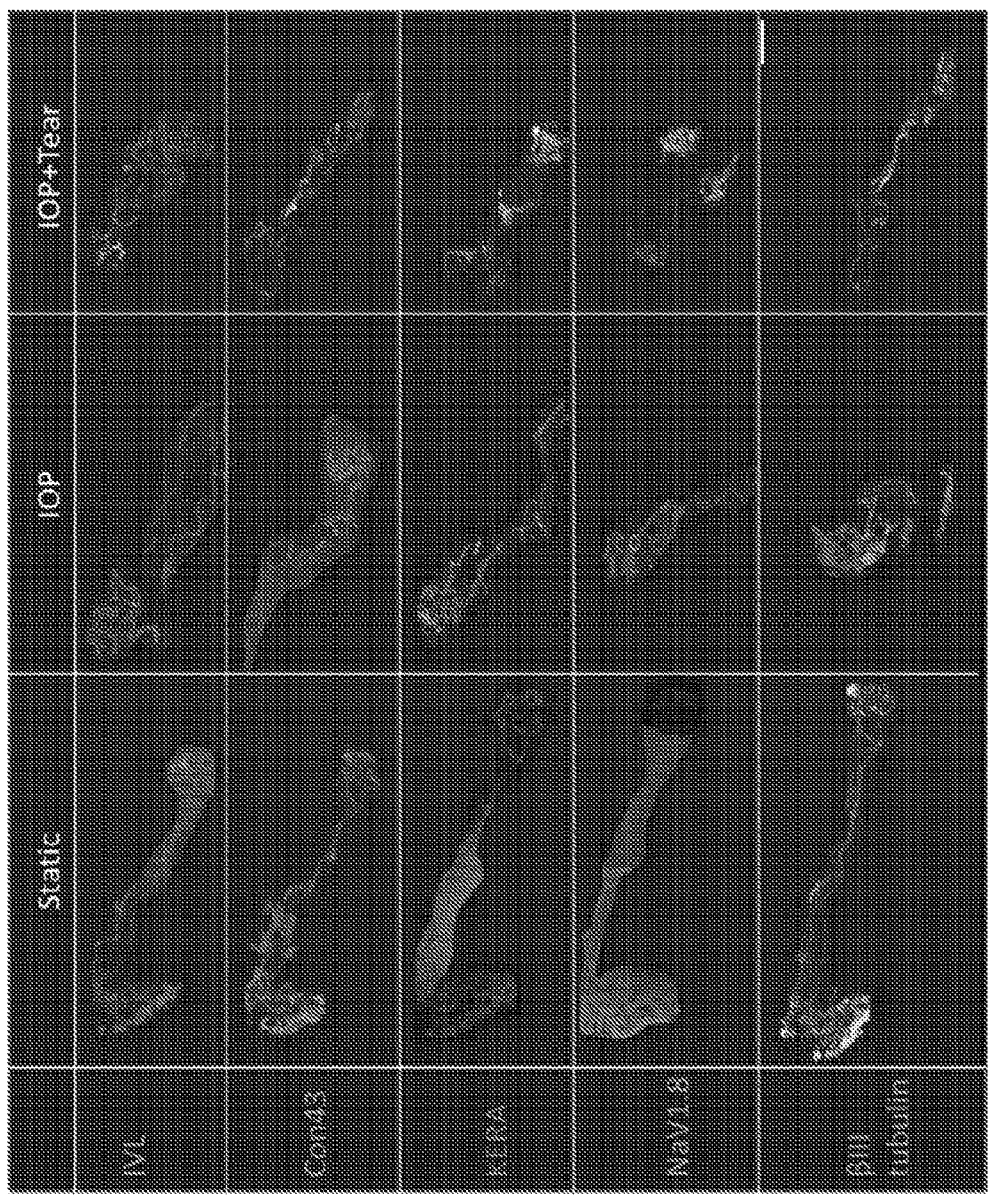
FIG. 18. Immunohistochemistry of corneal tissue models cultivated in static, IOP alone, and IOP+ tear wash bioreactors. Involucrin (IVL), connexin 43 (con 43), NaV 1.8 and III tubulin were stained green while keratocan was stained red. IOP+ tear wash group had most IVL, connexin 43, NaV 1.8. Whereas IOP and IOP+ tear wash groups both had higher keratocan expression than static cultivation. Scale bar=3 mm FIG. 19. Gene expression of hCSSCs and hCECs cultured in medium containing EGF and FBS. Q-PCR of IVL, GJA, KRT-3 expression from hCECs and KERA, LUM, ALDH and ACT expression from hCSSCs under stimulation of 5% 10% FBS, 25, and 50 ng/ml EGF. The hCECs appeared to have higher IVL, GJA and KRT-3 marker expression in 25 ng/ml and 10% FBS group than other groups. Whereas hCSSCs expressed most KERA, LUM, and ALDH in 5% FBS group. The data were collected from n>3 from three independent experiments. *P<0.0001; P<0.001.

Based on the preliminary data, no neuronal extensions were observed in the IOP alone group. However, with TF, neuronal extensions were observed on day 28 samples undergoing dynamic culture. Q-PCR data indicated (FIG. 17) that combined IOP+TF cultivation increased the expression of CRCP and SCN compared to static cultivation. Through IHC, higher β III tubulin expression was observed in the static culture samples than the IOP+TF culture, while NaV 1.8 expression was improved by IOP+TF cultivation (FIG. 18).

hCECs Responded to Dynamic Cultivation

In the IOP group, the mature corneal epithelium markers (IVL and connexin 43) were not expressed. However, in the IOP+TF group, IVL and connexin immunostain signals were observed and were statistically upregulated when compared to the IOP group and static cultivated samples (FIG. 18). In q-PCR result (FIG. 17), greater expression of IVL, and GJA4 was detected in IOP+TF group compared to static cultivation, suggesting tears improved the maturity of the epithelium.

TABLE 2

Primary and Secondary Antibodies for Immunostaining

| | Samples | Primary antibody dilution | Secondary antibody dilution |
|---|---|---|---|
| β tubulin III | ED, SD, ESD, E, S, D | Anti-β-tubulin III rabbit antibody 1:500 diluted in 5% BSA | Goat anti-rabbit IgG-FITC antibody (Sigma). 1:200 diluted in 5% BSA. Used donkey anti-rabbit IgG (FITC) (Abcam) when co-stained with keratocan 1:200 diluted in 5% BSA |
| Keratocan | SD, ESD, S | Anti-keratocan goat antibody 1:100 diluted in 5% BSA | Donkey anti-goat IgG, Alexa Fluor ® 568 (Sigma), 1:200 diluted in 5% BSA |
| Involucrin | ED, ESD, E | Anti-involucrin mouse antibody 1:500 diluted in 5% BSA | Goat anti-mouse IgG H&L (TRITC) (Abcam), 1:200 diluted in 5% BSA |

TABLE 3

Steps of Tissue Processing

| Dehydration | | Xylene exchange | | Paraffin | |
|---|---|---|---|---|---|
| Solution | time | Solution | Time | Solution | Time |
| 50% Ethanol | 10 min | 2:1 Ethanol:Xylene | 15 min | 2:1 Xylene:Paraffin | 30 min |
| 70% Ethanol | 10 min | 1:1 Ethanol:Xylene | 15 min | 1:1 Xylene:Paraffin | 30 min |
| 80% Ethanol | 10 min | 1:2 Ethanol:Xylene | 15 min | 1:2 Xylene:Paraffin | 30 min |
| 95% Ethanol | 10 min | 100% Xylene | 15 min | 100% Paraffin | 1 hr |
| 100% Ethanol | 10 min | 100% Xylene | 15 min | 100% Paraffin | 1 hr |
| 100% Ethanol | 10 min | 100% Xylene | 15 min | | |
| 100% Ethanol | 10 min | | | | |

Results:

Neuronal Stem Cell Differentiation

The expression level of CRCP, BDNF, TAC1, TRPV1 and NTRK1 at day 14 by the hNs was quantified by q-PCR to assess the effectiveness of differentiation of human iPS neurons. For neurons cultivated with 3I+3G neurobasal hCSSCs Responded to Dynamic Cultivation Higher KERA, LUM, and ALDH expression in the IOP+TF cultivation group was detected relative to the static cultured group in terms of both IHC (FIG. 18) and q-PCR (FIG. 17). These results indicated that IOP and TF improved the secretion of ECM components by hCSSCs.

To date, the impact of mechanical forces on corneal cells have been mainly studied in single cell type cultures. In order to further mimic the cellular component of human cornea we innervated the multicellular corneal tissue model with hNs differentiated from neuronal stem cells (hNSCs) derived from reprogrammed human dermal fibroblasts. Previously, 3I+3G neurobasal medium was shown to be effective for iPS cells differentiating towards sensory neurons. Here we adopted this method to differentiate the hNSCs. To evaluate the differentiation efficacy, the expression level of sensory neuron markers Tac1, BDNF, CRCP, TRPV1 and NTRK1 were evaluated. Tac1, BDNF and CRCP genes encode important peripheral pain mediators. TRPV1 is linked to nociceptive nerve firing following temperature and capsaicin stimulation. NTRK encodes neurotrophic factor receptors necessary for nerve cornea cross talk. Here, all human sensory neuronal markers were significantly upregulated in the differentiation experimental conditions using the 3I+3G neurobasal medium, indicating the effectiveness of the differentiation protocol.

To mimic the IOP, we applied the artificial anterior chamber used in corneal transplantation to inflate the scaffold with culture medium. The IOP was maintained in the range of 15-20 mmHg mimicking human cornea pressure. Maintaining pressure also served as an indicator that the bioreactor system remained sealed during the cultivation. In the human eye, the tear fluid is spread on the ocular surface by eye blink movement, with average rate of 10 times/min. To mimic these features, we designed the lid with a medium outlet to drip artificial tears on the scaffold surface with rate of 10 drops (5 µl/drop)/min. In our preliminary experiments, the tear fluid was dropped from a 2-3 cm height onto the tissue model. In these samples, no hCECs or hCSSCs were observed due to the forces imposed by the tear dropping. To solve this problem, we lowered the medium outlet to a 1 mm height from the scaffold surface and gained improved cell growth. On the native ocular surface, the tear fluid is drained through the tear duct and into the lacrimal sac by the nose. In our bioreactor, the tear fluid flowed off the surface due to the curvature of the pressurized tissue model. Thus, we placed a sterilized gauze pad underneath the anterior chamber to collect the tears.

The tissue model gained curvature and significantly increased secretion of stromal ECM (KERA, LUM) under stimulation of IOP, demonstrating the contribution of mechanical tension to corneal integrity. This result agreed with the contribution of IOP in corneal curvature and thickness during mice corneal development, demonstrating the promise of this bioreactor as an effective tissue model for future studies.

A custom designed lid was used to protect the artificial anterior chamber, however, contamination still occurred in some of the IOP alone samples. In the IOP+TF group, however, no contamination was observed during the culture period, suggesting medium flushing on the scaffold surface was effective washing out potential contaminants or pathogens in a similar manner to a human tear flow. In addition to preventing contamination, TF also improved the functionality of the corneal epithelium and innervation in the tissue model. As shown in IHC and Q-PCR results, TF enhanced the expression of IVL and connexin which indicated improvement of epithelial maturity. The higher expression of nociceptor NaV 1.8 in the IOP+TF group compared to the IOP alone group revealed the importance of TF to functional corneal innervation.

In vivo, aqueous humour generated IOP and air-liquid interface environment contribute to a healthy cornea. The aforementioned air-driven flex cell cannot fully replicate these physiological features. Currently, there is no bioreactor that combines the air-liquid interface environment, IOP and TF. Making use of our design, fluid generated IOP and ALIC provided a representative, physiologically relevant model. Additional tear flow elements provide the chance of studying tear function within an in vitro environment. By tunning the IOP, tear and aqueous humour components, diseases like glaucoma, dry eye syndrome, and ocular surface infection can be mimicked in vitro using this new system.

In this Example, a bioreactor was developed to mimic the mechanical and biochemical properties of IOP and TF. As described herein, IOP improved stromal ECM secretion while TF promoted the maturity of the epithelium and neuronal extensions, as well as reducing contamination. Such responses match the functioning of native cornea, demonstrating the utility of this corneal tissue model and bioreactor system in studying corneal reactions to mechanical stimulation. The bioreactor allows adjustment of IOP pressure, tear formulation and aqueous humour components, and can serve as a platform of mimicking the dynamic environment of healthy and diseased cornea.

Example 4—Response to Nociceptive Stimulation

In this example, unless otherwise specified the materials and methods used were as follows.
Materials & Methods:
Q-PCR of hCSSCs and hCECs Cultured in Media Containing EGF and FBS In order to encourage epithelial and stromal recovery following capsaicin stimulation, 4 types of medium (5% or 10% FBS, 25 or 50 ng/ml EGF supplemented hCSSCs differentiation medium) were added to hCSSCs and hCECs monocultures. RNA was processed (extraction, reverse transcribed) on day 14 (D14) according to previously known methods. Briefly, total RNA was extracted using Trizol with single step acid-phenol guanidinium method, adsorbed onto a silica-gel membrane using the Qiagen RNeasy Kit protocol (Qiagen, Valencia, Calif.), eluted, and quantified. The RNA extracted from the scaffolds was reverse transcribed to cDNA in a 20 µl reaction using high-capacity cDNA reverse transcription kit (Thermo Fisher). Quantitative RT-PCR of cDNA (~30 ng/µl) was performed using assays containing fluorescent hybridization probes (Taq Man: Thermo Fisher). Reactions were incubated at 95° C. for 10 min and amplification was carried out on samples with 2 min incubation at 50° C., followed by 50 cycles of 15 seconds at 95° C. and 1 min at 60° C. The reaction for RT-PCR was processed in a 15 µl solution containing 1× Universal PCR Master Mix (Thermo Fisher) with 6 µl cDNA samples. RNA expression at day 14 was compared to day 0 samples using 18s as a reference gene.

Expression of lumical (LUM), keratocan (KERA), aldehyde dehydrogenase 3 family member A1(ALDH3A1), actin alpha 2 (ACTA2), involucrin (IVL), gap junction protein alpha 4 (GJA4) and keratin 3 (KRT3) was evaluated through q-PCR to evaluate cellular response as previously described.

Capsaicin Stimulation and Serum Treatment on Corneal Model Compositions

Following 28 days of culture of the tissue model at the air-liquid interface, 10 µl DMEM containing 0.5%, 0.05%. 0.005%, 0.0005% capsaicin was pipetted on top of the scaffolds. Capsaicin supplemented DMEM was rinsed off with PBS following a 10 min incubation period. The scaffolds were then placed back on the floating shelf to continue cultivation. For convenience, day 28 co-culture is defined as day 0 after capsaicin stimulation in this Chapter (DO cap). Three days after initial capsaicin stimulation, hCSSCs differentiation medium containing 10% FBS was added for 24 h to improve the healing of corneal cells and neurons. Following the serum treatment, the samples were cultured in hCSSCs differentiation medium with 50 ng/ml NGF until day 9. The serum treated (STSR), non-serum treated (ST), and non-stimulated (no ST) samples were collected on day 9 after capsaicin stimulation, for q-PCR and IHC analysis.

DiI and DiO Labeling of Cells

To observe cellular response to different concentrations of capsaicin, neurons were labelled with DiO and corneal cells with DiI (ThermoFisher) by diluting the dye at a ratio of 1:500 (v/v) in a 1,000,000 cells/ml solution prior to seeding on the scaffolds. Images were collected every two days from 1 day before capsaicin stimulation (day−1) to day 9.

ELISA of SP and CGRP

Substance P (SP) and calcitonin gene related peptide (CGRP) are mediators used to assess the pain reactions. Supernatant culture media samples were collected every 2 days after capsaicin stimulation and stored at −80° C. The frozen medium samples were lyophilized overnight and dissolved in 1 ml of deionized water. ELISAs for SP and CGRP were processed using an SP parameter assay kit (R&D system) and human CGRP EIA kit (Cayman Chemistry, Ann Arbor, Mich.).

Immunohistochemistry and q-PCR

The immunohistochemistry (IHC) and q-PCR data were processed following the same or similar procedures described above. SP8 CARS confocal microscopy (Leica) was used for 3D image acquisition.

Results:

hCECs and hCSSCs Reaction to FBS and EGF

Figure 19:
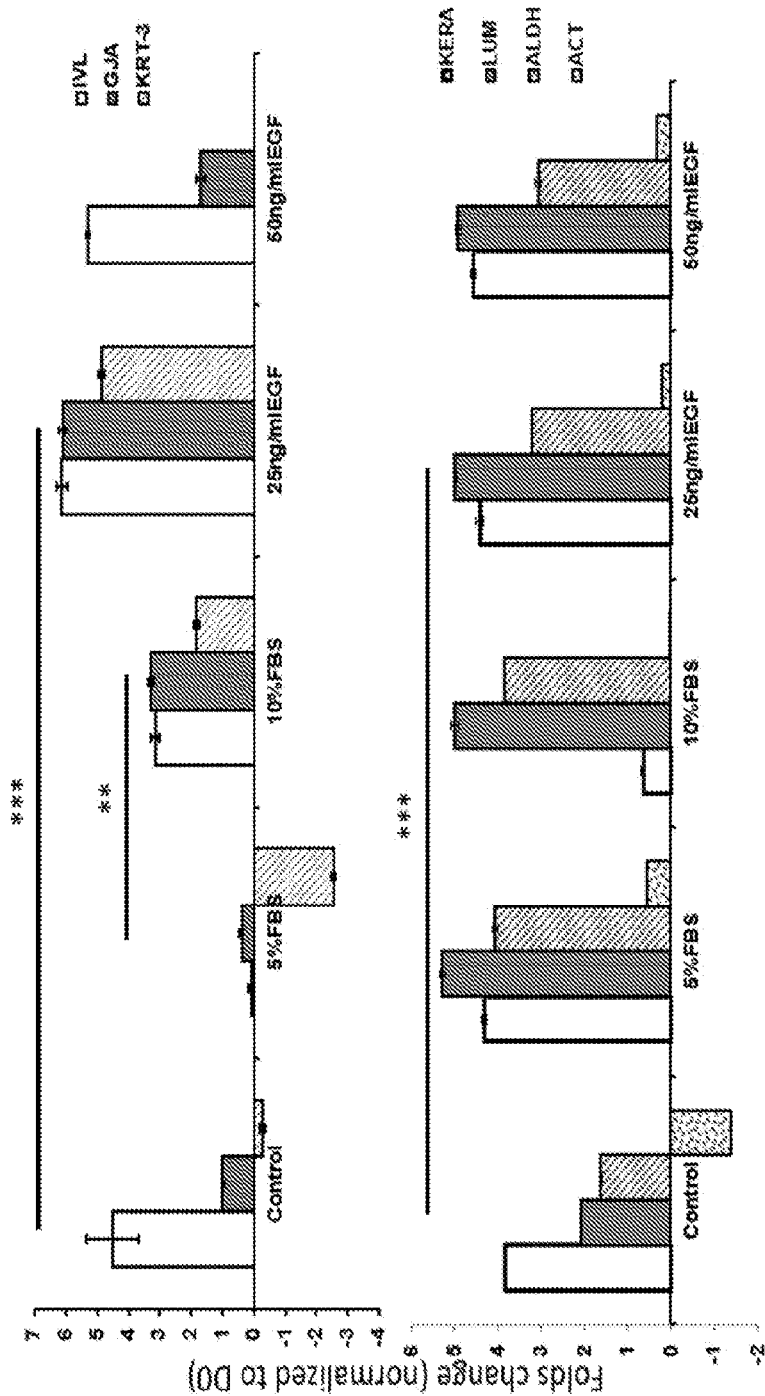

To optimize the concentration of FBS and EGF in the regrowth improving medium, 10 and 5% FBS, 25 and 50 ng/ml EGF supplemented hCSSCs differentiation medium were tested with D14 hCSSCs and hCECs mono-cultures grown on TCP. The q-PCR results showed hCECs maturity marker (IVL, GJA4 and KRT-3) expression improved in the 10% FBS and 25 ng/ml EGF groups. HCSSCs ECM marker expression (KERA, LUM, ALDH) was increased by all 4 types of media, with the lowest amount of non-stromal differentiation marker (ACT) expression observed in the 10% FBS group. Thus, 10% FBS supplemented medium was chosen as the healing medium for the tissue model after capsaicin stimulation (FIG. 19).

DiI Labeled Corneal Cells Response to Capsaicin Stimulation

Figure 20:
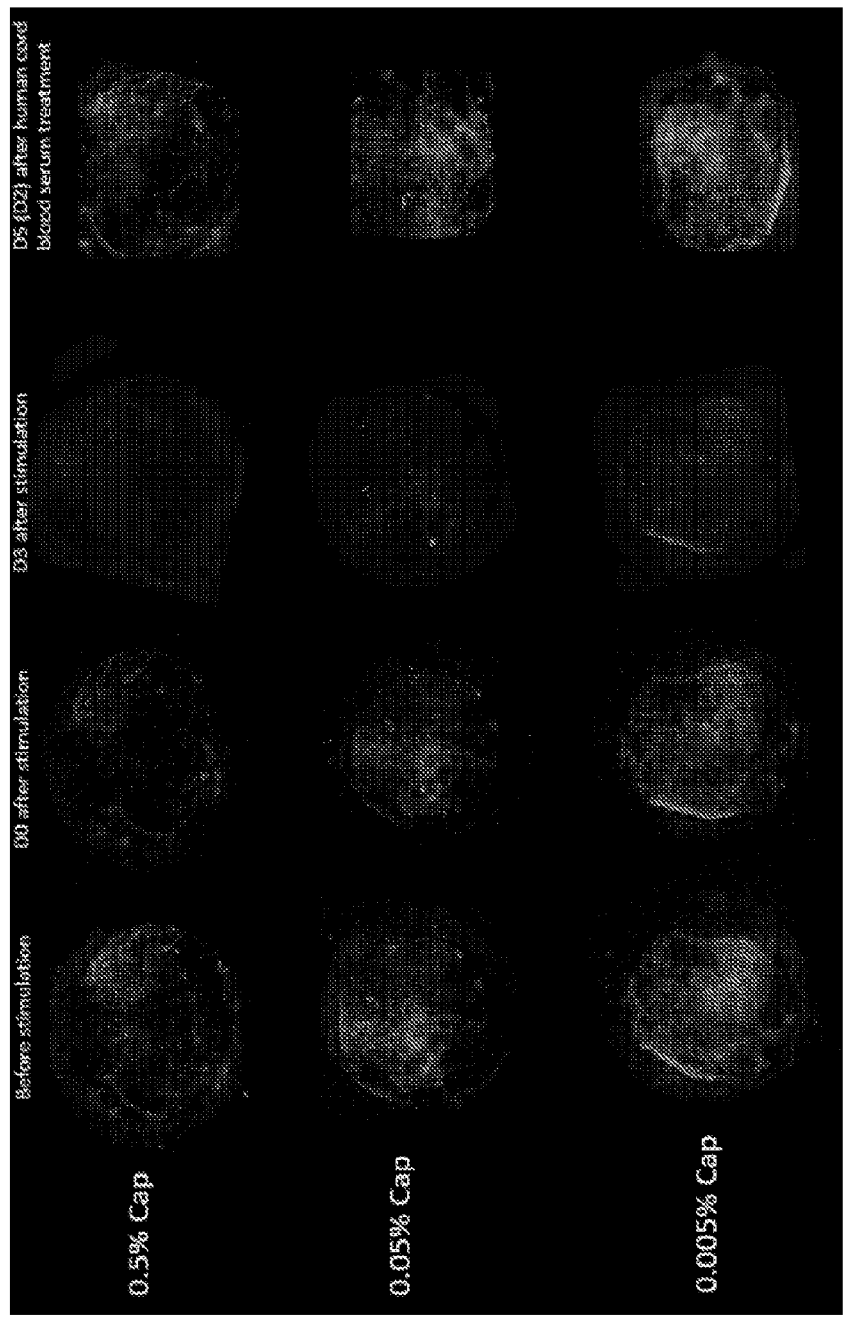
FIG. 20. Live cell image of corneal cell response to different concentration of capsaicin. DiI (red) labeled hCSSCs and hCECs reacted to 10 min exposure to 10 μL capsaicin (0.5, 0.05, 0.005%), day 3 after stimulation and after serum treatment. The 0.005% capsaicin appeared to provide decrease of cell coverage after exposure while recovered after the serum treatment.
Figure 21:
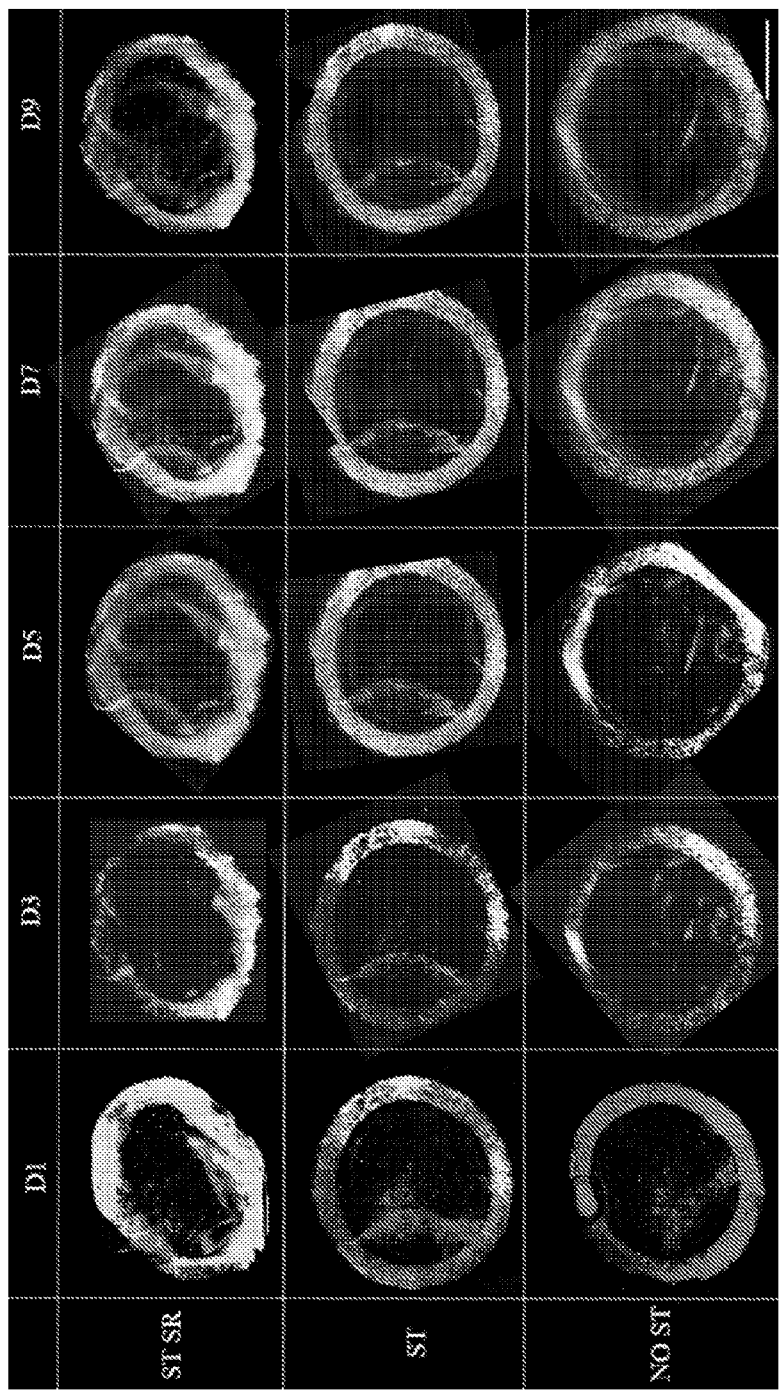
FIG. 21. Confluency change observed through live cell imaging. Stitched fluorescence images captured from stimulated (ST), stimulated and serum treated (STSR), and non-stimulated (NO ST) samples. The corneal cells were labeled red with DiI while neurons were labeled green with DiO. Scale bar=6 mm FIG. 22. Immunohistochemistry of corneal tissue model regions (E: epithelium, S: stroma, N: neuron) on day 14 after exposure to 0.005% capsaicin in ST(stimulated), NOST (non-stimulated) and STSR (serum treated) groups. β III tubulin was stained as green, red represent the auto fluorescence of silk scaffolds. Neuronal extension disappeared at samples at 3 days after capsaicin stimulation with change of cellular morphology in epithelium and stroma observed as well. The serum treatment improved the density axons and epithelial cells compared to the control group. While the D14 control has the elongated stromal cells. Scale bar=50 µm.

To seek the optimal stimulation concentration, tissue models containing DiI labeled corneal cells and DiO labeled hNs were stimulated by 0.5, 0.05, 0.005% capsaicin in DMEM. FIG. 20 shows the stitched images of corneal tissue model on D2 before stimulation, D0 (immediately after stimulation), and D3 and D5 after stimulation. As shown in FIG. 20, 0.5 and 0.05% capsaicin decreased the cell density upon stimulation. Reduction of cell coverage was observed 5 days after 0.005% capsaicin stimulation. Recovery of cell confluency was observed after serum treatment in all groups with the 0.005% group demonstrating the best regrowth (FIG. 21). Thus 0.005% capsaicin was selected for all remaining experiments.

To study serum treatment, neurons were labeled green with DiO while corneal cells were labeled red with DiI. After the capsaicin exposure, a decrease of cellular confluency was found on day 3. The non-serum treated (ST) group showed continuous decrease of cellular confluency after the capsaicin stimulation. For the serum treated group (STSR) we saw an increase of cell confluence on day 7 and 9 indicating the serum treatment improved regrowth of corneal cells.

Figure 22:
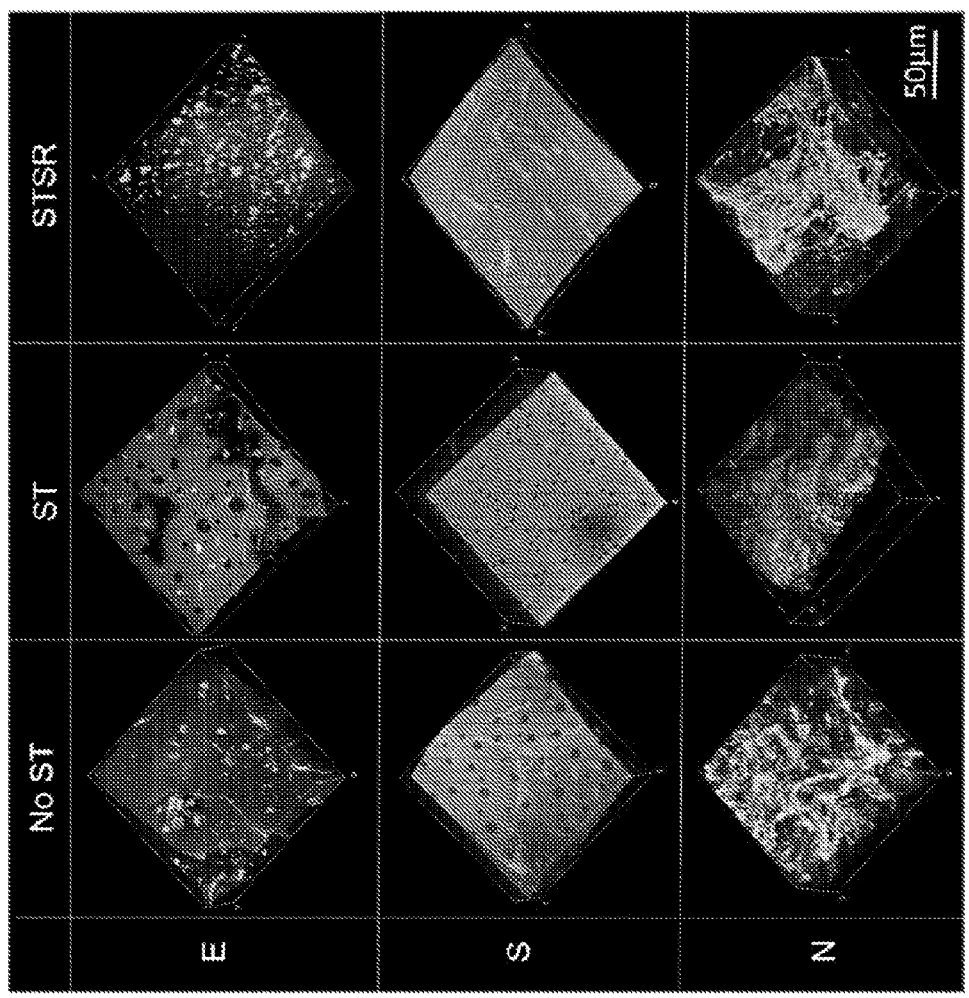

Confocal Microscopy of Tissue Model after Capsaicin Stimulation and Serum Treatment Confocal microscopy was utilized to assess cellular morphology in the scaffolds, with results shown in FIG. 22. No neuronal extensions were observed in the ST group. HCECs and hCSSCs showed altered cell morphology and decreased cell number compared to the non-stimulated group (NO ST). After serum treatment (STSR), longer and denser axons were observed in the capsaicin stimulated group than the No ST and STSR samples. The STSR samples also had multi-layer epithelium. However, the recovery of morphology and density of hCSSCs were not achieved in serum treated samples.

Substance P and CGRP Release

Figure 23:
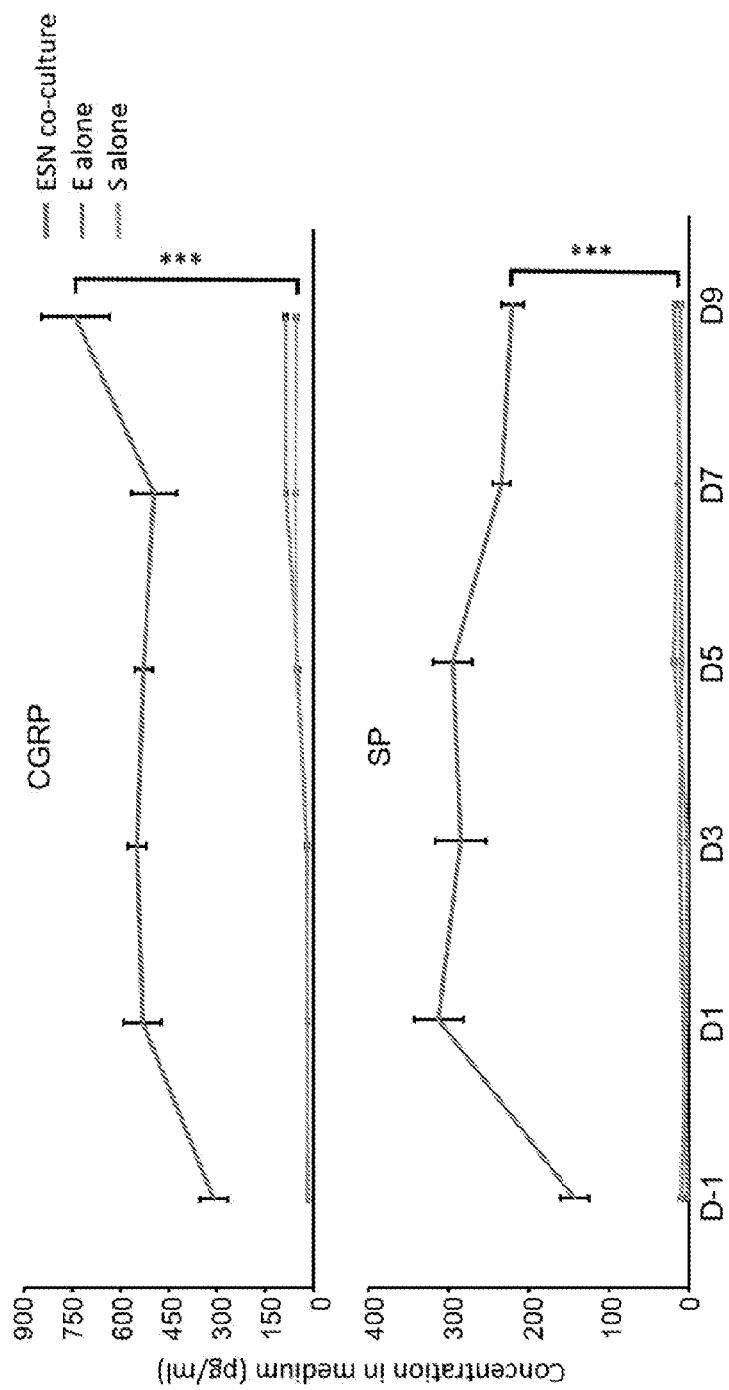
FIG. 23. ELISA of substance P and CGRP secretion from capsaicin stimulated samples. The concentration of substance P and CGRP both increased after stimulation and was higher than in the control group. The data were collected from n>3 from three independent experiments. ***P<0.0001.

SP and CGRP in the medium was evaluated by ELISA. The SP and CGRP concentration increased following capsaicin treatment, and decreased on the day of serum treatment (FIG. 23). Then SP was maintained at a lower level (~220 pg/ml), whereas CGRP appeared to be increased 4 days after serum treatment. There was no significant secretion of SP and CGRP in the monoculture control group (FIG. 23).

HCECs, hCSSCs and hNs Marker Expression after Capsaicin Stimulation

Figure 24:
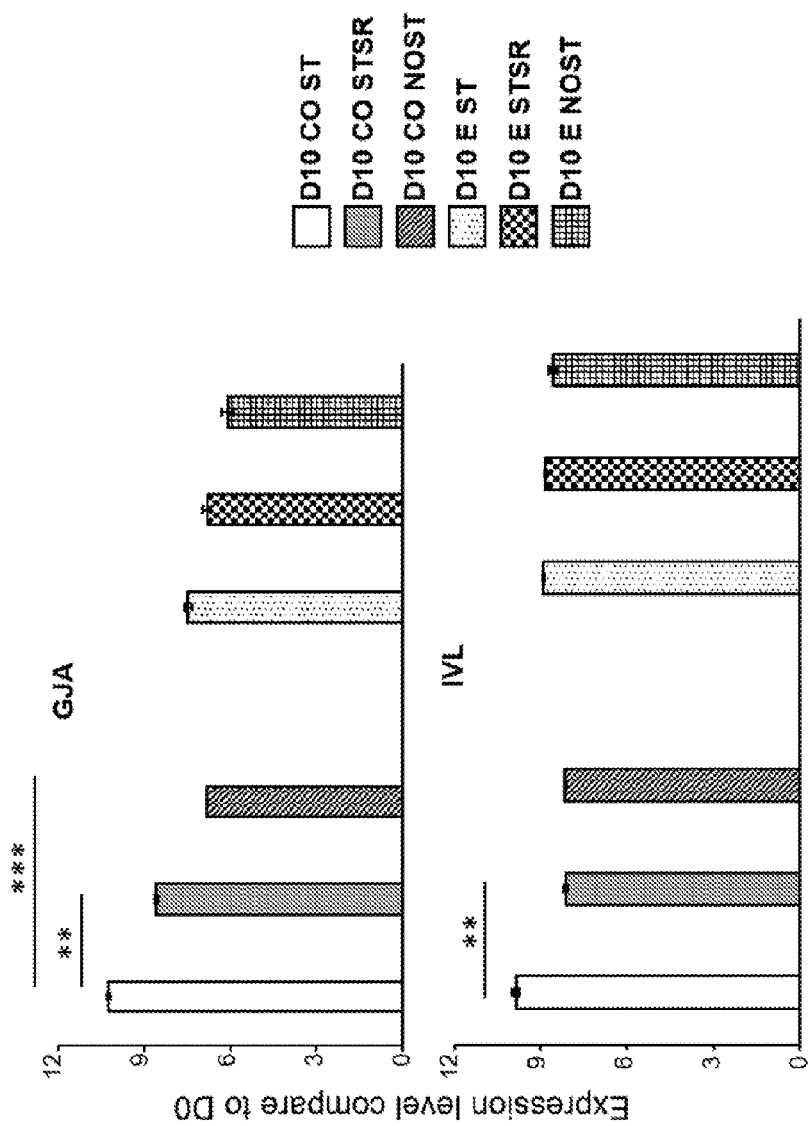
FIG. 24. Q-PCR result for GJA and IVL expression from hCECs after capsaicin stimulation. Samples are collected on day 10 after stimulation from co-cultures (D10 CO ST, D10 CO STSR, D10 CO NOST), and mono-cultures (D10 E ST, D10 E STSR, D10 E NOST). ST stand for stimulated but not treated with serum. The STSR group was treated with serum and NOST means non-stimulated group. GJA and IVL were upregulated in ST monoculture and co-culture groups. Serum treated samples had higher GJA expression than monoculture and non-stimulated groups. The data was collected from n>2 experiments. *P<0.0001; P<0.001.
Figure 25:
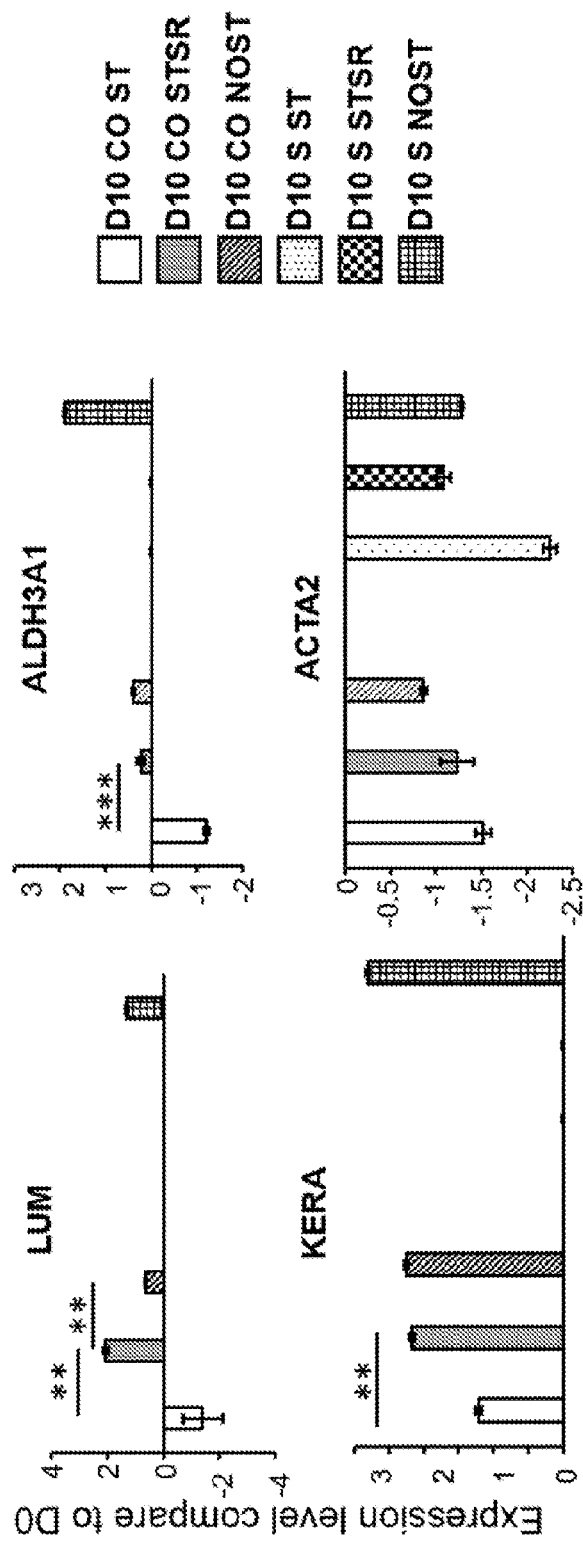
FIG. 25. Q-PCR results for LUM, ALDH3A1 KERA and ACTA2 expression from hCSSCs after capsaicin stimulation. Samples are collected on day 10 after stimulation from co-cultures (D10 CO ST, D10 CO STSR, D10 CO NOST), and mono-cultures (D10 S ST, D10 S STSR, D10 S NOST). ST stand for stimulated but not treated with serum. STSR group was treated with serum and NOST means non-stimulated group. LUM, ALDH3A1, KERA expression in ST groups were less than STSR group and NOST group. Expression of ACTA2 was down regulated in all the groups. No significant LUM, ALDH3A1 and KERA expression was detected in S, ST and S STSR groups. The data was collected from n>2 experiments. *P<0.0001; P<0.001.
Figure 26:
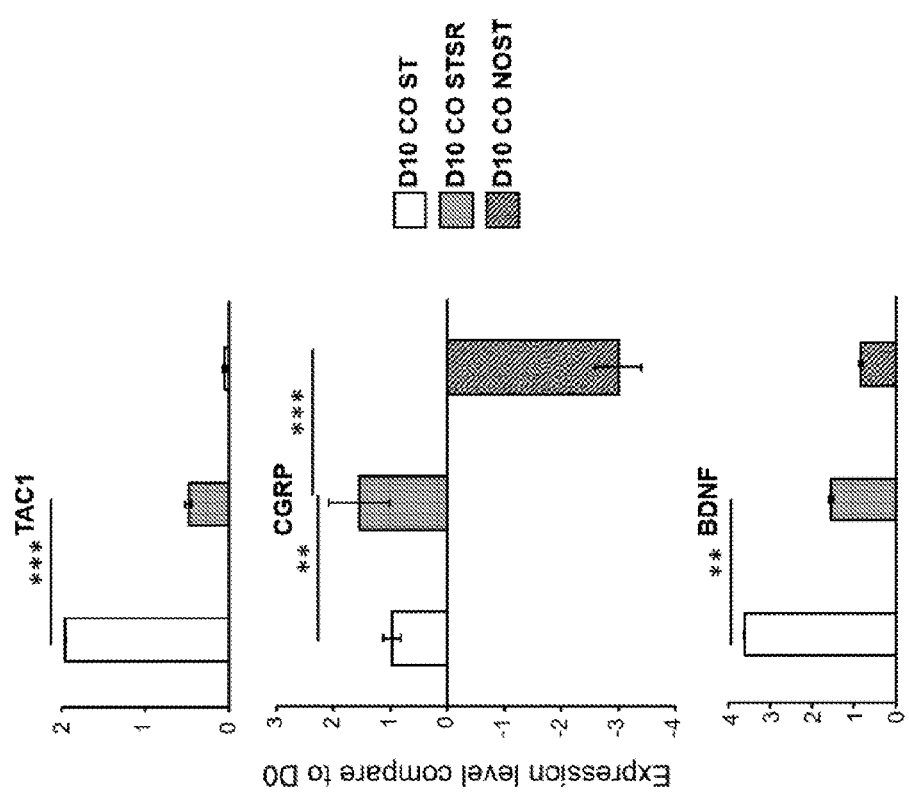
FIG. 26. Q-PCR result for TAC1, CGRP and BDNF from neuron after capsaicin stimulation. Samples are collected on day 10 after stimulation from co-cultures (D10 CO ST, D10 CO STSR, D10 CO NOST). ST stand for stimulated but not treated with serum. STSR group was treated with serum and NOST means non-stimulated group. TAC1, CGRP and BDNF expression was upregulate in ST groups. Serum treated group have lower BDNF, TAC1 and higher CGRP expression than ST group. The data was collected from n>2 experiments.

In FIG. 24, both GJA and IVL had the highest expression in the capsaicin stimulated co-cultures (D10 CO ST). In FIG. 25, LUM, ALDH3A1 and KERA expression were decreased for D10 CO ST samples. The serum treated group (D10 CO STSR) had comparable LUM, KERA and ALDH3A1 expression with non-stimulated co-cultures (D10 CO NOST). In hCSSCs mono-cultures, the LUM, KERA and ALDH3A1 expression were only detected in the non-stimulated group (D10 S NOST), while ACTA2 was down regulated in all the groups. The expression of TAC1 and BDNF was highest D10 ST group, while CGRP expressed highest in serum treated group D10 STSR (FIG. 26).

In this Example, certain provided compositions were exposed to a known environmental stressor, capsaicin, and the response was characterized. Capsaicin is known to cause pain upon application, and cause ulceration of the epithelium and nerve degeneration after longer term exposure. To treat corneal epithelial and corneal nerve defects, a cocktail of growth factors including EGF, TGF-β, fibronectin, IGF-1 and NGF is considered as one of the most effective treatments. In this example, 10% FBS was used to mimic administration of such a cocktail and allow for observation of healing in certain provided compositions.

As described herein, for example, through confocal images, a decrease of axonal density, hCECs and hCSSCs confluency were observed in ST group indicating capsaicin caused in vitro tissue damage. Interestingly we observed increased GJA and IVL expression from hCECs in both co-cultured and monocultured ST groups, showing the capsaicin stimulation improved the maturity of the epithelium. In human cornea, epithelial cells respond to trauma by proliferating and migrating towards the injured site. Thus, it is likely the hCECs increased the synthesis of its functional marker to perform its protective function. For hCSSCs, in confocal images, cell confluency was decreased in ST group compared to NOST group. This is consistent with keratocytes apoptosis after epithelium injury observed in clinic. In q-PCR results, the D10 S ST group showed no ECM marker expression. However, ECM markers were expressed in the D10 CO ST group. These results indicated the importance of neuronal innervation in maintaining the functionality of corneal stroma.

Also as described herein, the healing medium containing 10% FBS improved the cell confluency of hCECs, hCSSCs, and the density of innervation after capsaicin exposure. The comparable ECM marker expression from hCSSCs in D10 CO STSR and D10 CO NOST groups showed the serum treatment is effective in restoring corneal stromal cell functionality. This matches the healing effect observed through the recovery of corneal epithelium and innervation in human patients that used serum eye drops.

SP and CGRP are found in tears during corneal pain cause by dry eye syndrome and after capsaicin stimulation. These pain mediators are secreted by mature and functional human sensory neurons. Both SP and CGRP can regulate stratification of corneal epithelial cells, restoring epithelial barrier function, and improving wound healing in animal models. Thus SP and CGRP are measured assessing the pain response on corneal tissue model. In this Example, it was found that the SP and CGRP concentration in culture medium increased after capsaicin stimulation and decreased after serum treatment. The SP and CGRP are secreted from hNs in the scaffold as no significant release was detected from the hCECs and hCSSCs monocultures. Q-PCR results demonstrated cellular expression of TAC1, CRCP which agreed with ELISA data. This Example shows the first method able to to detect SP, CGRP release from capsaicin stimulated human sensory neurons in an in vitro environment. This demonstrates the maturity and functionality of innervation of several provided compositions and further indicates that a pain-like response in an innervated corneal tissue model is achievable.

In the provided examples, the interaction between corneal epithelial and/or stromal cells and innervation was also observed through morphological analyses. The axons developed from the bottom of, for example, a silk sponge, and grew towards the top of the scaffold in single culture and co-culture groups. In tri-culture examples, the axons branched at the edge of scaffold and sprouted thin and long axons that grew in between stromal layers and on the epithelial layer. Epithelial innervation that was developed through cultivation formed close connections with hCECs in the ALIC. In stromal layers of certein provided examples, axons were guided by the pattern on the silk film and grew parallel with hCSCs. Through the longer and denser axons in the ESD-ALIC compared to the ED-ALIC, a synergistic effect by the hCSCs was revealed. This finding is in agreement with our previous study which illustrated the importance of collagen type I and BDNF secreted by hCSCs in improving neuronal extensions. Interestingly, we observed longer axons in all the ALIC groups. A similar effect was shown in other DRG neuron single cultures and co-cultures with skin tissue at the air-liquid interface. The results indicate the importance of the ALIC in supporting long and dense neuronal innervation at in vitro environment.

Cultivation time for previously known cornea tissue models was limited to 1-2 weeks. In contrast, native corneal development takes 2 months in the human embryo. As such, prior model systems were unable to provide conditions suitable for the development of a system capable of replicating the native developmental process and thus its function. Though the cells in these examples were not embryonic, as shown herein, hCSCs can be cultured up to 6 weeks and sustain ECM secretion (unpublished data) when used in accordance with provided compositions, systems, and methods. The ability to study and manipulate interactions between innervation and corneal tissue in longer term cultures provides important new paradigms in the treatment of corneal dysfunction and/or disease.

As exemplified herein, innervated silk-based corneal tissue models were developed which supported long and dense neuronal innervation with multi-layer hCEC for the epithelium and aligned hCSCs for the stromal layers. Among the advantages provided by various embodiments, the impact of functional innervation on the corneal stroma and epithelium in sustained culture is demonstrated by the present examples, and represents a significant new advance in providing physiologically relevant tissue systems for study and/or the development of drugs or other therapeutics to treat, inter alia, corneal dysfunction and/or disease.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A tissue composition comprising
a first silk scaffold comprising a plurality of epithelial cells;
a second silk scaffold comprising a plurality of stromal cells;
and a plurality of neurons;
wherein one or more silk scaffold has a porosity of at least 10%.

2. The composition of claim 1, wherein the plurality of neurons are present in a third silk scaffold.

3. The composition of claim 2, wherein the third silk scaffold at least partially surrounds the first and second silk scaffolds.

4. The tissue compostion of claim 1, further comprising a third silk scaffold.

5. The composition of claim 1, wherein the neurons are human neurons.

6. The composition of claim 1, wherein the stromal cells comprise keratocytes and/or corneal stromal fibroblast cells.

7. The composition of claim 1, wherein at least one silk scaffold is selected from a silk film, a silk sponge, silk hydrogel and a silk-collagen mix hydrogel.

8. The tissue composition of claim 1, wherein the first silk scaffold and/or the second silk scaffold is optically clear.

9. A method of making a tissue composition comprising
providing a first silk scaffold comprising a plurality of epithelial cells;
associating a second silk scaffold comprising a plurality of stromal cells with the first silk scaffold to form a silk scaffold stack; and
introducing a plurality of neurons to the silk scaffold stack to form a tissue composition,
wherein at least some of the plurality of neurons innervate at least one of: a portion of the epithelial cells, and a portion of the stromal cells;
wherein one or more silk scaffold has a porosity of at least 10%.

10. A tissue composition comprising
a first silk scaffold comprising a plurality of epithelial cells;
a second silk scaffold comprising a plurality of stromal cells;

a plurality of neurons; and a tear-like fluid;

wherein the tear-like fluid is or comprises an aqueous solution including at least one lipid, at least one antibiotic, and at least one neurotrophic peptide.

11. The tissue composition of claim 1, wherein the first silk scaffold and the second silk scaffold are associated to form a silk scaffold stack.

12. The tissue composition of claim 10, wherein the plurality of neurons are present in a third silk scaffold.

13. The tissue composition of claim 12, wherein the third silk scaffold at least partially surrounds the first and second silk scaffolds.

14. The tissue composition of claim 10, wherein the neurons are human neurons.

15. The tissue composition of claim 10, wherein the first silk scaffold and the second silk scaffold are associated to form a silk scaffold stack.

16. The tissue composition of claim 10, wherein the first silk scaffold and/or the second silk scaffold is optically clear.

* * * * *

UNITED STATES PATENT AND TRADEMARK OFFICE
CERTIFICATE OF CORRECTION

| | | |
|---|---|---|
| PATENT NO. | : 10,864,299 B2 | Page 1 of 1 |
| APPLICATION NO. | : 16/096851 | |
| DATED | : December 15, 2020 | |
| INVENTOR(S) | : David L. Kaplan et al. | |

It is certified that error appears in the above-identified patent and that said Letters Patent is hereby corrected as shown below:

In the Specification

Column 16, Line 52, "((3-sheet" should be --(β-sheet--.

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*